(12) United States Patent
Nozawa et al.

(10) Patent No.: US 7,283,296 B2
(45) Date of Patent: Oct. 16, 2007

(54) SURGICAL MICROSCOPE

(75) Inventors: Junichi Nozawa, Sagamihara (JP);
Motokazu Nakamura, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 11/484,122

(22) Filed: Jul. 11, 2006

(65) Prior Publication Data

US 2006/0291044 A1    Dec. 28, 2006

Related U.S. Application Data

(63) Continuation of application No. PCT/JP2005/000147, filed on Jan. 7, 2005.

(30) Foreign Application Priority Data

| Jan. 13, 2004 | (JP) | ............................. 2004-005495 |
| Jan. 13, 2004 | (JP) | ............................. 2004-005496 |
| Feb. 23, 2004 | (JP) | ............................. 2004-046502 |

(51) Int. Cl.
*G02B 21/00* (2006.01)

(52) U.S. Cl. ................. 359/384; 359/382; 248/123.11; 248/585

(58) Field of Classification Search ................ 359/382, 359/384
See application file for complete search history.

(56) References Cited

U.S. PATENT DOCUMENTS

| 4,339,100 | A |   | 7/1982 | Heller et al. ............. 248/123.1 |
| 4,523,732 | A |   | 6/1985 | Biber et al. ............. 248/123.1 |
| 5,651,718 | A | * | 7/1997 | Nakamura ................ 248/123.2 |
| 5,825,536 | A |   | 10/1998 | Yasunaga et al. ........... 359/384 |
| 6,050,630 | A |   | 4/2000 | Hochet ....................... 296/187 |
| 6,105,909 | A | * | 8/2000 | Wirth et al. ............. 248/123.2 |
| 6,550,734 | B1 | * | 4/2003 | Spadea ................... 248/280.11 |

FOREIGN PATENT DOCUMENTS

| EP | 0 023 003 A1 | 1/1981 |
| EP | 0 048 404 A1 | 3/1982 |

(Continued)

OTHER PUBLICATIONS

International Search Report PCT/JP2005/000147 dated Apr. 5, 2005.

*Primary Examiner*—Stephone B. Allen
*Assistant Examiner*—Lee Fineman
(74) *Attorney, Agent, or Firm*—Ostrolenk, Faber, Gerb & Soffen, LLP

(57) ABSTRACT

There is provided a surgical microscope having a horizontal movement arm portion which moves a microscope portion in a substantially horizontal direction, and a vertical movement arm portion which moves the microscope portion in a substantially vertical direction. A first elastic force generation mechanism connected with a base bottom portion and the horizontal movement arm portion generates an elastic force which offsets a rotation moment around a first horizontal rotation axis produced when the horizontal movement arm portion revolves around the first horizontal rotation axis arranged in the base bottom portion. Further, a second elastic force generation mechanism connected with the base bottom portion and the vertical movement arm portion generates an elastic force which offsets a rotation moment around a second horizontal rotation axis produced when the vertical movement arm portion revolves around the second horizontal rotation axis arranged in the horizontal movement arm portion.

16 Claims, 51 Drawing Sheets

FOREIGN PATENT DOCUMENTS

| | | |
|---|---|---|
| EP | 0 700 665 A1 | 3/1996 |
| EP | 0 781 529 A1 | 7/1997 |
| JP | 57-86806 | 5/1982 |
| JP | 63-36481 | 7/1988 |
| JP | 7-100147 A | 4/1995 |
| JP | 8-140932 A | 6/1996 |
| JP | 8-266555 A | 10/1996 |
| JP | 9-182759 A | 7/1997 |

* cited by examiner

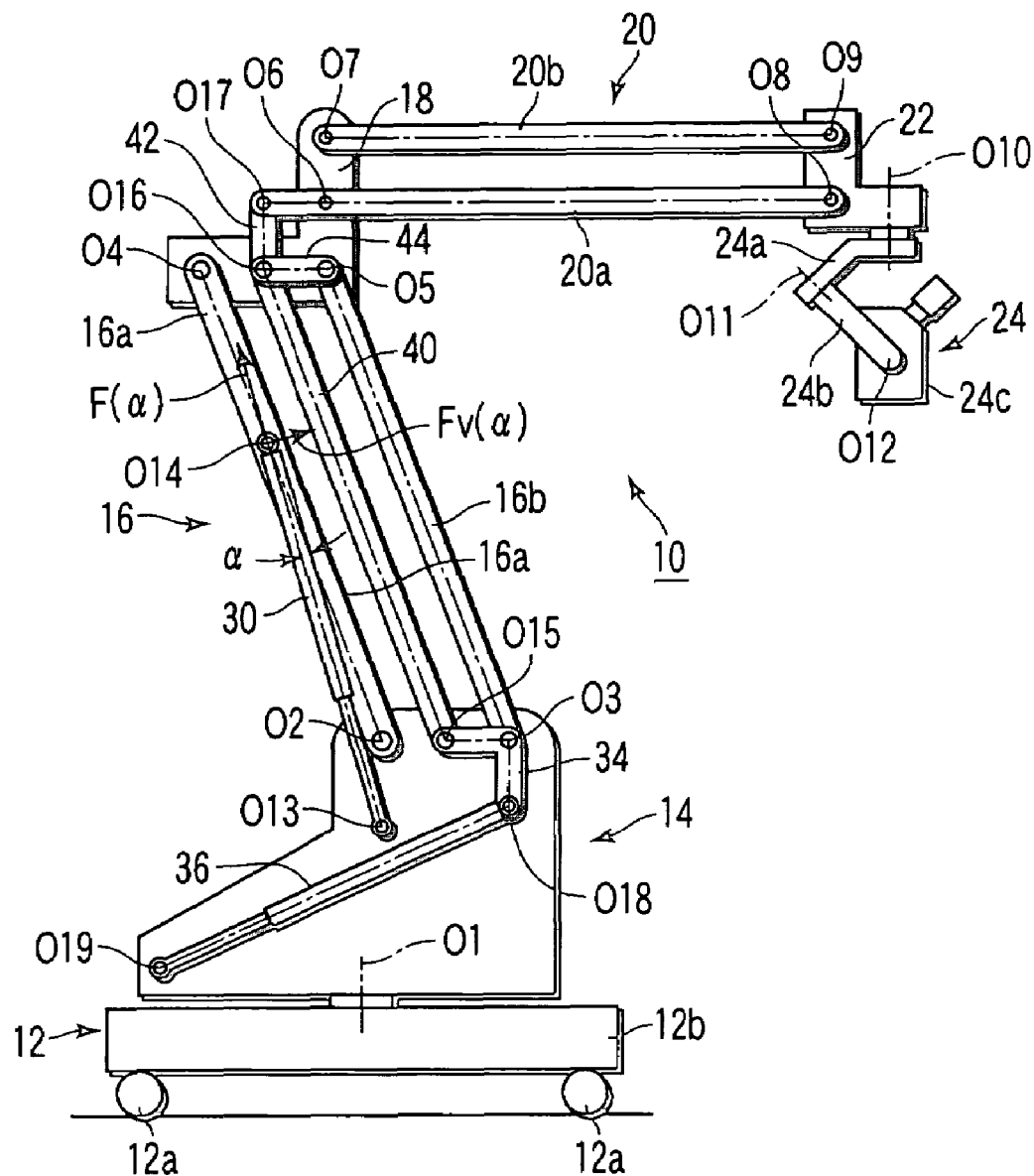
F I G. 2A

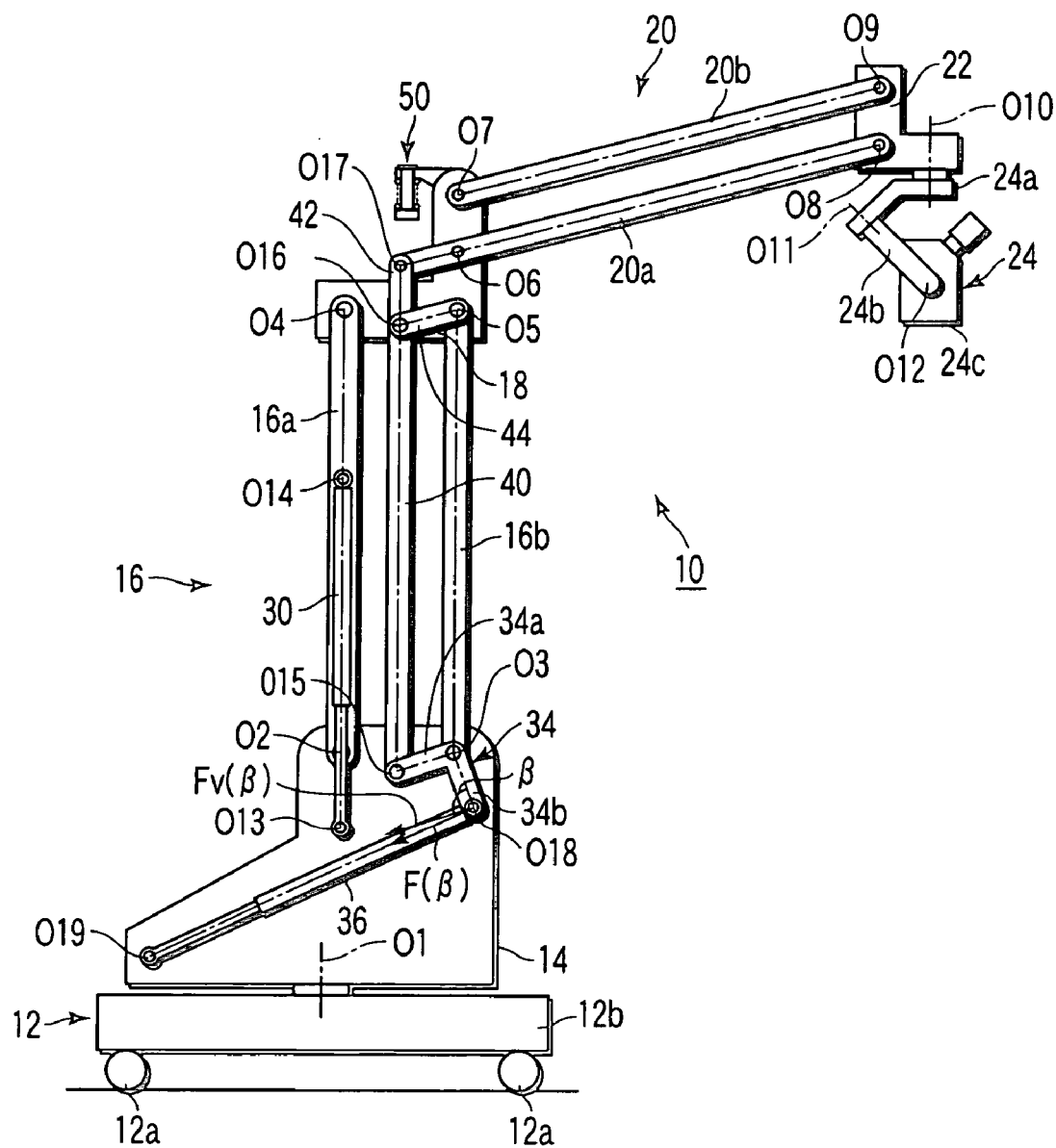
F I G. 3A

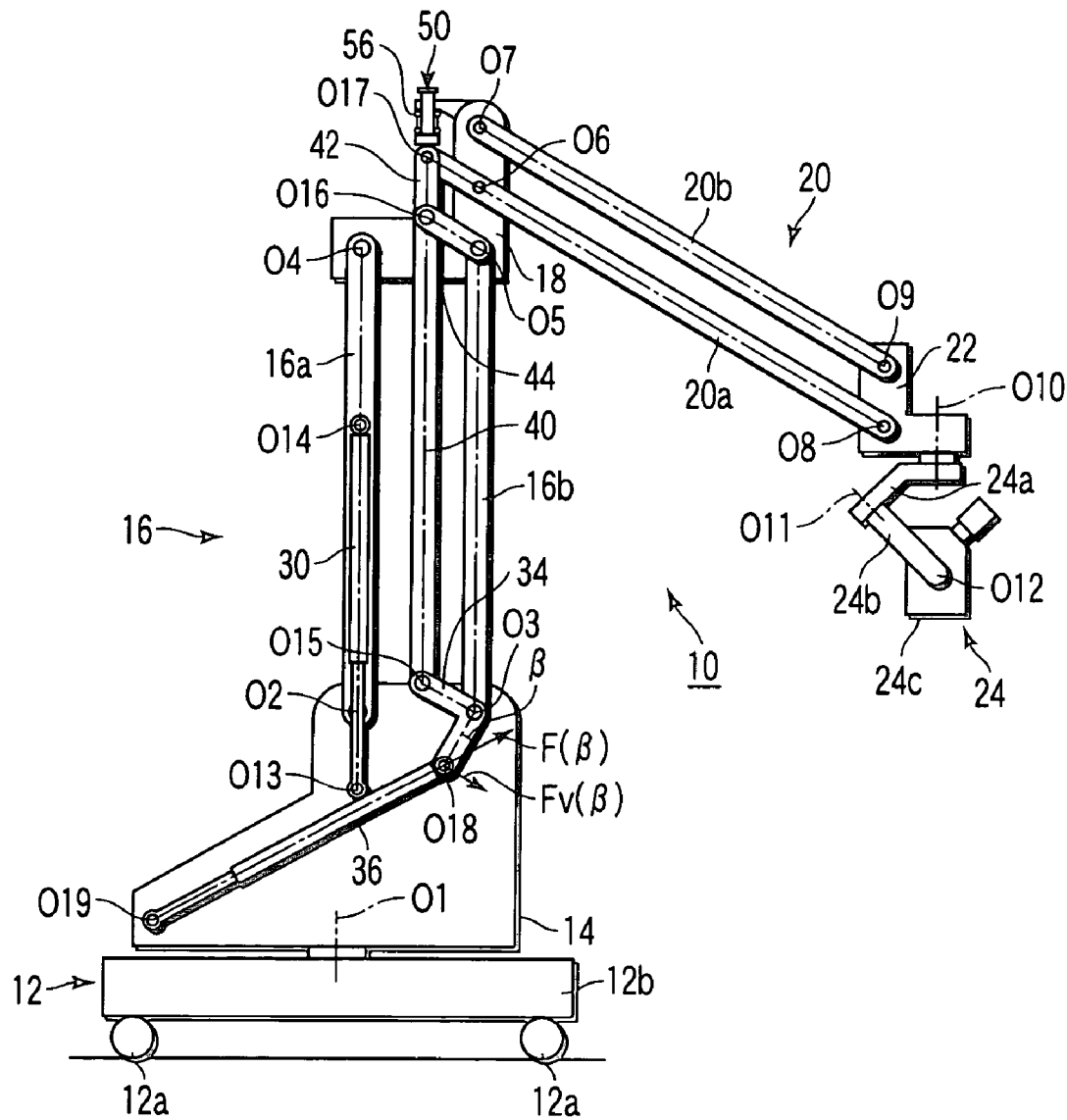
F I G. 3B

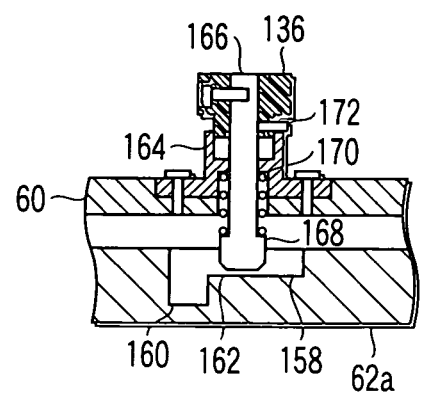
F I G. 10B
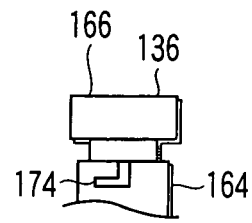
F I G. 10C
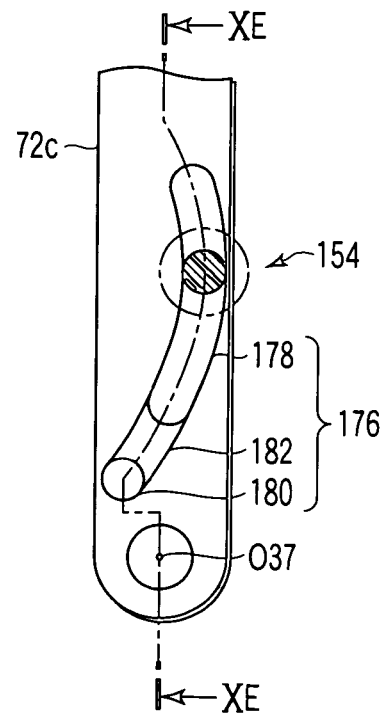
F I G. 10D

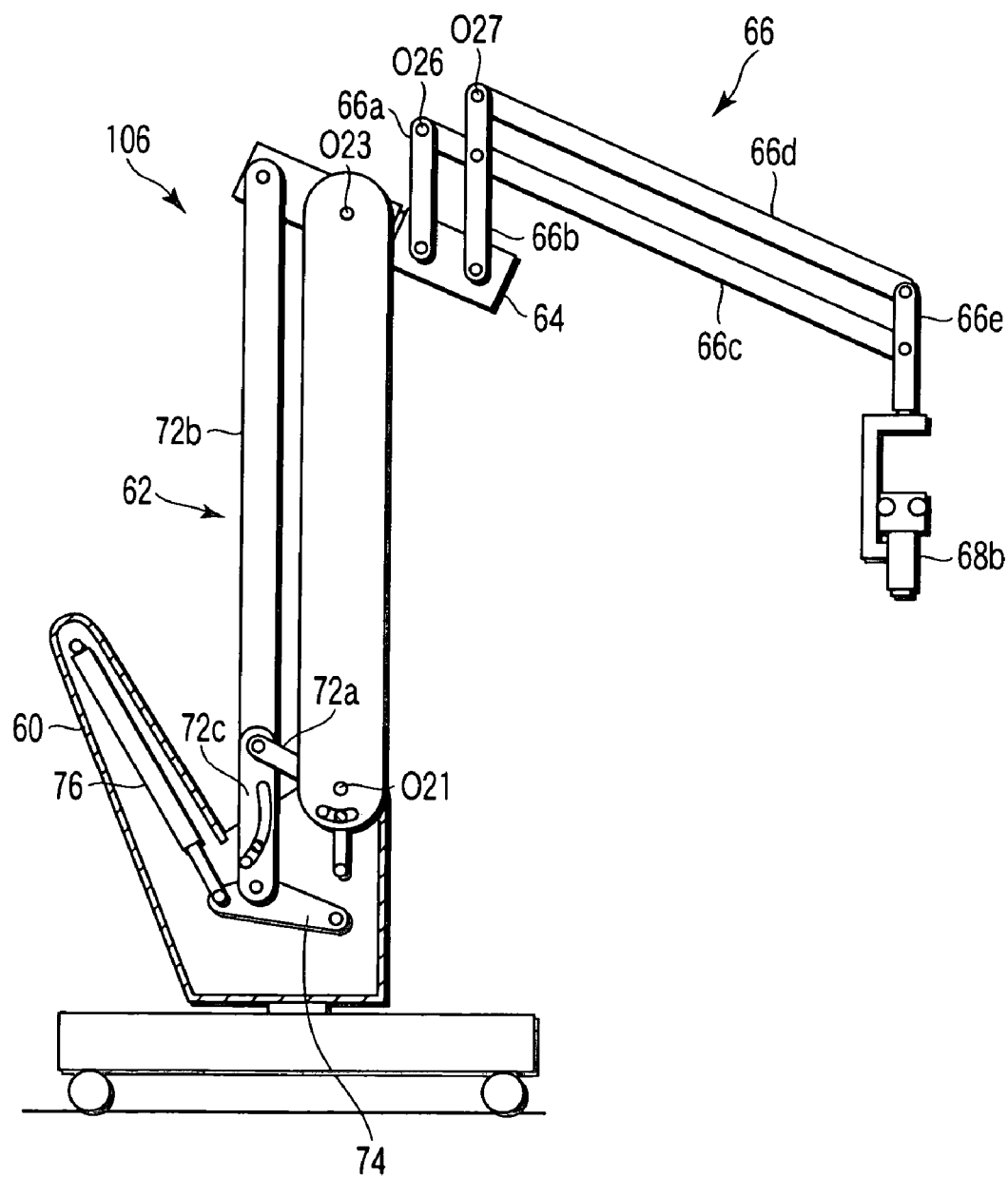
F I G. 16A

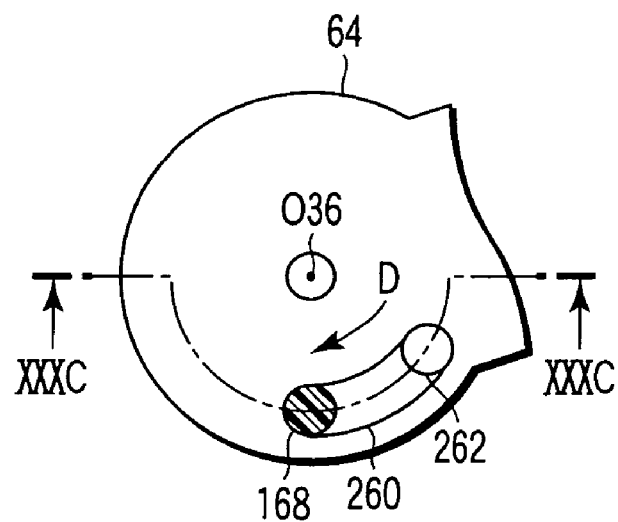
F I G. 30B
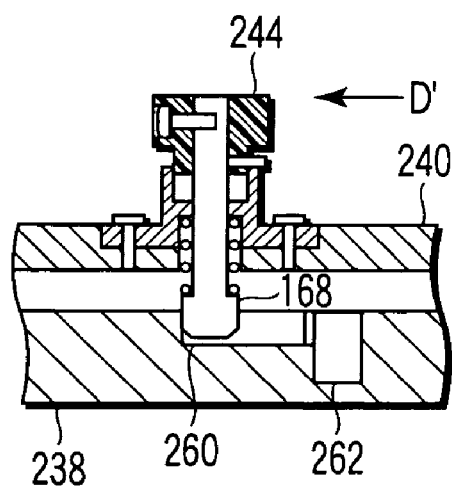
F I G. 30C

SURGICAL MICROSCOPE

CROSS-REFERENCE TO RELATED APPLICATIONS

This is a Continuation Application of PCT Application No. PCT/JP2005/000147, filed Jan. 7, 2005, which was published under PCT Article 21(2) in Japanese.

This application is based upon and claims the benefit of priority from prior Japanese Patent Applications No. 2004-005495, filed Jan. 13, 2004; No. 2004-005496, filed Jan. 13, 2004; and No. 2004-046502, filed Feb. 23, 2004, the entire contents of all of which are incorporated herein by reference.

BACKGROUND OF THE INVENTION

1. Field of the Invention

The present invention relates to a surgical microscope for use in, e.g., a surgical operation.

2. Description of the Related Art

A surgical microscope has a stand which movably supports a microscope portion having an observation mechanism. A stand of a surgical microscope disclosed in, e.g., Jpn. Pat. Appln. KOKAI Publication No. 1982-86806 has a parallelogram link mechanism which is used to move a microscope portion in a vertical direction. A spring which redresses the balance of the parallelogram link mechanism is arranged in this parallelogram link mechanism.

Further, a stand of a surgical microscope disclosed in Jpn. Pat. Appln. KOKAI Publication No. 1996-140932 has a link mechanism which moves a microscope portion in a horizontal direction and a vertical movement arm which moves the microscope portion in a vertical direction. That is, one end portion of the link mechanism is pivoted at a base bottom portion or the like, and the other end portion of the same can revolve around one end portion. The vertical movement arm is arranged at the other end portion of the link mechanism. This vertical movement arm is formed of a parallelogram link mechanism, and a spring which redresses the balance of the parallelogram link mechanism is arranged in this parallelogram link mechanism. Furthermore, the microscope portion is provided to the vertical movement arm.

Moreover, Jpn. Pat. Appln. KOKAI publication No. 1988-36481 discloses a mechanism which inclines a binocular tube of a microscope portion. An inclination arm is connected with a support portion which supports the microscope portion in such a manner that this arm can revolve around an axis extending in a horizontal direction. This inclination arm rotatably supports the binocular tube around a central axis of the binocular tube. That is, the binocular tube is moved to incline by rotation around the axis extending in the horizontal direction and rotation around the central axis of the binocular tube. Moreover, a rotation moment generated by the inclining movement of the binocular tube is canceled out by a function of a counterweight.

BRIEF SUMMARY OF THE INVENTION

According to one aspect of the present invention, there is provided a surgical microscope comprising: a microscope portion having an observation mechanism; a base bottom portion in which a first horizontal rotation axis extending in a substantially horizontal direction is arranged; a horizontal movement arm portion which is supported by the base bottom portion to be revolvable around the first horizontal rotation axis and in which a second horizontal rotation axis extending in the substantially horizontal direction is arranged and which moves the microscope portion in the substantially horizontal direction; a vertical movement arm portion which is supported by the horizontal movement arm portion to be revolvable around the second horizontal rotation axis, supports the microscope portion and moves the microscope portion in a substantially vertical direction; a first elastic force generation mechanism which is connected with the base bottom portion and the horizontal movement portion and generates an elastic force which offsets a rotation moment around the first horizontal rotation axis produced when the horizontal movement arm portion revolves around the first horizontal rotation axis; and a second elastic force generation mechanism which is connected with the base bottom portion and the vertical movement arm portion and generates an elastic force which offsets a rotation moment around the second horizontal rotation axis produced when the vertical movement arm portion revolves around the second horizontal rotation axis.

According to another aspect of the present invention, there is provided a surgical microscope comprising: a microscope portion having an observation mechanism; a support portion in which a horizontal rotation axis extending in a substantially horizontal direction is arranged; a vertical movement arm portion which is supported by the support portion to be revolvable around the horizontal rotation axis, supports the microscope portion and moves the microscope portion in a substantially vertical direction; a first balance mechanism which is connected with the support portion and the vertical movement arm portion and generates a force which offsets a rotation moment around the horizontal rotation axis generated when the vertical movement arm portion revolves around the horizontal rotation axis; and a second balance mechanism which generates a force which corrects the imbalance of a rotation movement of the vertical movement arm portion around the horizontal rotation axis and a rotation moment around the horizontal rotation axis produced by an offsetting force of the first balance mechanism.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic view showing the surgical microscope according to the first embodiment of the present invention in a state where a microscope portion is moved toward a left side in a horizontal direction in a page space;

FIG. 3A is a schematic view showing the surgical microscope according to the first embodiment of the present invention in a state where the microscope portion is moved toward an upper side in a vertical direction in the page space;

FIG. 3B is a schematic view showing the surgical microscope according to the first embodiment of the present invention in a state where the microscope portion is moved toward a lower side in the vertical direction in the page space;

FIG. 10B is a cross-sectional view showing the first restriction mechanism of the surgical microscope according to the third embodiment of the present invention taken along a line XB-XB in FIG. 10A;

FIG. 10C is a side view showing a first knob portion and a pedestal of the first restriction mechanism of the surgical microscope according to the third embodiment of the present invention;

FIG. 10D is a cross-sectional view showing a second restriction mechanism of the surgical microscope according to the third embodiment of the present invention;

FIG. 16A is a cross-sectional view showing the surgical microscope according to the third embodiment of the present invention in a state where the microscope body is set at an in-use downward movement limit;

FIG. 30B is a cross-sectional view showing the restriction mechanism of the surgical microscope according to the second reference embodiment of the present invention in a state where the microscope body is set at the in-use upward movement limit;

FIG. 30C is a cross-sectional view showing the restriction mechanism of the surgical microscope according to the second reference embodiment of the present invention in a state where the microscope body is set at the in-use upward movement limit taken along a line XXXC-XXXC in FIG. 30B;

DETAILED DESCRIPTION OF THE INVENTION

A first embodiment of the present invention will now be described hereinafter with reference to FIGS. 1A to 4. Here, a description will be given as to a surgical microscope 10 in a state where a later-described horizontal movement arm portion 16 is extended in a vertical direction and a vertical movement arm portion 20 is extended in a horizontal direction (which will be referred to as an initial state hereinafter).

Figure 1A:
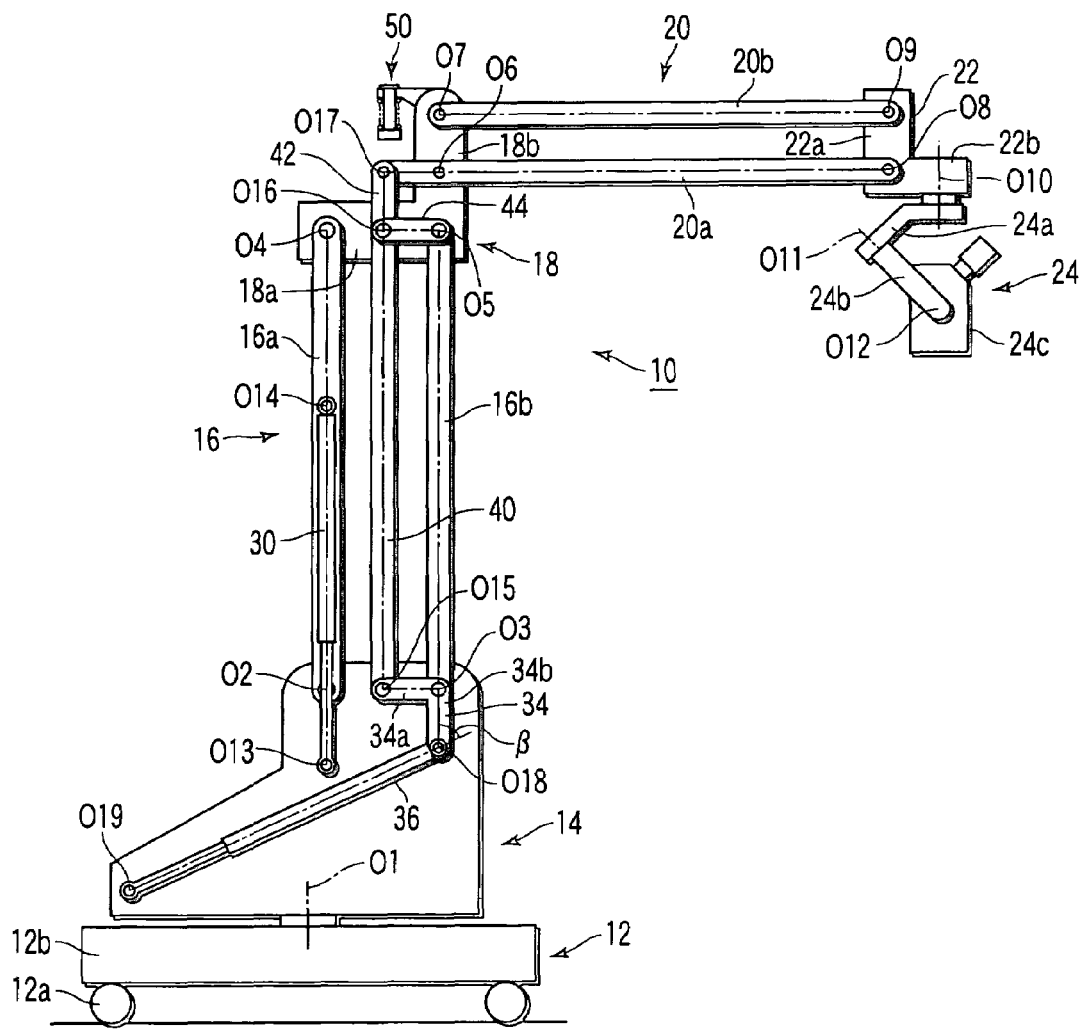
FIG. 1A is a side view showing an outline structure of a surgical microscope according to a first embodiment of the present invention.

Referring to FIG. 1A, a movement mechanism of a microscope portion 24 of the surgical microscope 10 according to this embodiment will now be briefly explained. A base 12 is arranged at a base end portion of the surgical microscope 10, and a base bottom portion 14 is arranged on this base 12. One end portion of the horizontal movement arm portion 16 which moves the microscope portion 24 in the horizontal direction is connected with this base bottom portion 14. One end portion of the vertical movement arm portion 20 which moves the microscope portion 24 in the vertical direction is connected with a joint portion 18 arranged at the other end portion of this horizontal movement arm portion 16. The microscope portion 24 having an observation mechanism is connected with an end joint portion 22 arranged at the other end portion of this vertical movement arm portion 20.

Giving a more detailed description, as shown in FIG. 1A, the base 12 has a base main body 12b, and a plurality of casters 12a each having a stopper are arranged on a lower surface of this base main body 12a. The entire surgical microscope 10 can be moved/fixed on a flat horizontal surface such as a floor by the plurality of casters 12a each having a stopper.

Further, the base bottom portion 14 is pivoted on an upper surface of the base main body 12b, and the base bottom portion 14 can rotate with respect to the base 12 around a first rotation axis O1 extending in a substantially vertical direction through a substantially central part of the base bottom portion 14. Lower end portions of first and second vertical links 16a and 16b of the horizontal movement arm portion 16 are adjacently pivoted on the upper part of this base bottom portion 14 at substantially the same heights. Further, the first and second vertical links 16a and 16b can freely revolve with respect to the base bottom portion 14 around second and third rotation axes O2 and O3 extending in a substantially horizontal direction through the lower end portions of the first and second vertical links 16a and 16b. Here, the first and second vertical links 16a and 16b have a rod-like shape and substantially the same lengths. In the initial state, the first and second vertical links 16a and 16b are extended in the vertical direction.

Upper end portions of the first and second vertical links 16a and 16b are connected with the joint portion 18. This joint portion 18 has an L-like shape, and two arms 18a and 18b are extended from a bent portion to be perpendicular to each other. The upper end part of the first vertical link 16a is pivoted at an apex portion of an end part of one arm 18a. Furthermore, the first vertical link 16a can revolve with respect to the joint portion 18 around a fourth rotation axis O4 extending in the substantially horizontal direction through the upper end portion of the first vertical link 16a.

Moreover, the upper end portion of the second vertical link 16b is pivoted at the apex portion in the middle of the bent portion. Additionally, the second vertical link 16b can revolve with respect to the join portion 18 around a fifth rotation axis O5 extending in the substantially horizontal direction through the upper end portion of the second vertical link 16b.

Here, a distance between the upper end portions of the first and second vertical links 16a and 16b is substantially equal to a distance between the lower end portions of the same. In the initial state, one arm 18a of the joint portion 18 is extended in the horizontal direction (a left direction in FIG. 1A) from the bent portion, and the other arm 18b is extended in the vertical direction (an upper direction in FIG. 1A) from the bent portion.

The second to fifth rotation axes O2, . . . , O5 are arranged at apex portions of a parallelogram in a vertical plane. Therefore, the first and second vertical links 16a and 16b can revolve while being kept parallel with each other. That is, the horizontal movement arm portion 16 can revolve around a first horizontal rotation axis (the second and third rotation axes O2 and O3) arranged in the base bottom portion 14.

First and second horizontal links 20a and 20b of the vertical movement arm portion 20 are connected with the other arm 18b of the joint portion 18. A portion of the first horizontal link 20a adjoining one end portion (a left end part in FIG. 1A) thereof is pivoted at a position adjacent to the bent portion of the other arm 18b. Further, the first horizontal link 20a can revolve with respect to the joint portion 18 around a sixth rotation axis O6 extending in the substantially horizontal direction through the portion of the first horizontal link 20a adjoining one end portion thereof.

Furthermore, one end portion (the left end part in FIG. 1A) of the second horizontal link 20b is pivoted at the end portion of the other arm 18b. Moreover, the second horizontal link 20b can revolve with respect to the joint portion 18 around a seventh rotation axis O7 extending in the substantially horizontal direction through one end portion of the second horizontal link 20b.

The first and second horizontal links 20a and 20b have a rod-like shape and are extended in the same direction (the right direction in FIG. 1A) with respect to the joint portion 18. In the initial state, the first and second horizontal links 20a and 20b are extended in the horizontal direction.

The other end portions (a right end part in FIG. 1A) of the first and second horizontal links 20a and 20b are connected with the end joint portion 22. The end joint portion 22 has an L-like shape like the joint portion 18, and two arms 22a and 22b are extended from the bent portion to be perpendicular to each other. The other end portion of the first horizontal link 20a is pivoted at the apex portion in the middle of the bent portion. Further, the first horizontal link 20a can revolve with respect to the end joint portion 22 around an eighth rotation axis O8 extending in the substantially horizontal direction through the other end portion of the first horizontal link 20a.

Furthermore, the other end portion of the second horizontal link 20b is pivoted at the apex portion at the end part of one arm 22a. Moreover, the second horizontal link 20b can revolve with respect to the end joint portion 22 around a ninth rotation axis O9 extending in the substantially horizontal direction through the other end part of the second horizontal link 20b. Here, a distance between the other end portions of the first and second horizontal links 20a and 20b is substantially equal to a distance between the portion of the first horizontal link 20a adjoining one end portion thereof and the other end part of the second horizontal link 20b. In the initial state, one arm 22a of the end joint portion 22 is extended toward an upper side in the vertical direction (the upper direction in FIG. 1A) from the bent portion, and the other arm portion 22b is extended in the horizontal direction (the right direction in FIG. 1A) from the bent portion.

The sixth, seventh, ninth and eighth rotation axes O6, O7, O9 and O8 are arranged at apex portions of a parallelogram in a vertical plane. Therefore, the first and second horizontal links 20a and 20b can revolve while being kept parallel to each other. That is, the vertical movement arm portion 20 can revolve around a second horizontal rotation axis (the sixth and seventh rotation axes O6 and O7) arranged in the horizontal movement arm portion 16. Moreover, in this embodiment, the base 12, the base bottom portion 14 and the horizontal movement arm portion 16 form a support portion which supports the vertical movement arm portion 20.

One end portion of a first inclination arm 24a of the microscope portion 24 is pivoted on a lower surface of the end portion of the arm 22b in the end joint portion 22. Additionally, the first inclination arm 24a can rotate with respect to the joint portion 22 around a 10th rotation axis O10 extending in the vertical direction through one end portion of the first inclination arm 24a. The first inclination arm 24a forms a predetermined angle with the 10th rotation axis O10, and is obliquely suspended from the end joint portion 22.

One end portion of a rod-like second inclination arm 24b is pivoted at the other end portion of the first inclination arm 24a. Further, the second inclination arm 24b can rotate with respect to the first inclination arm 24a around an 11th rotation axis O11 extending in a central axis direction of the second inclination arm 24b through one end portion of the second inclination arm 24b. This 11th rotation axis O11 extends in a direction different from the horizontal direction and the vertical direction.

A binocular tube 24c of the microscope portion 24 through which an operator observes a patient is pivoted at the other end portion of the second inclination arm 24b. This binocular tube 24c can revolve with respect to the second inclination arm 24b around a 12th rotation axis O12 extending in the horizontal direction through the other end portion of the second inclination arm 24b.

Therefore, the microscope portion 24 can be rotated around the 10th to 12th rotation axes O10, O11 and O12 to be inclined with respect to the vertical movement arm portion 20.

Accordingly, the microscope portion 24 can move in the substantially horizontal direction (a substantially left-and-right direction in FIG. 1A) by revolving of the horizontal movement arm portion 16 around the first horizontal rotation axis (the second and third rotation axes O2 and O3), and can move in the substantially vertical direction (a substantially up-and-down direction in FIG. 1A) by revolving of the vertical movement arm portion 20 around the second horizontal rotation axis (the sixth and seventh rotation axes O6 and O7). Additionally, the binocular tube 24c of the microscope portion 24 can be inclined by rotation around the 10th to 12th rotation axes O10, O11 and O12.

Referring to FIG. 1A, an outline of a balance mechanism of the surgical microscope 10 will now be described. The surgical microscope 10 has first and second elastic force generation mechanisms. The first elastic force generation mechanism generates an elastic force which offsets a moment produced around the first horizontal rotation axis (the second and third rotation axes O2 and O3) by revolving of the horizontal movement arm portion 16. Further, the second elastic force generation mechanism generates an elastic force which offsets a moment produced around the second horizontal rotation axis (the sixth and seventh rotation axes O6 and O7) by revolving of the vertical movement arm portion 20. Furthermore, the second elastic force generation mechanism also serves as a first balance mechanism. Moreover, the surgical microscope 10 has an auxiliary balance mechanism 50 as a second balance mechanism. This auxiliary balance mechanism 50 generates a force which corrects the imbalance of a rotation moment of the vertical movement arm portion 20 around the second horizontal rotation axis and a rotation moment around the second horizontal rotation axis produced by an offsetting force of the first balance mechanism.

Giving a detailed description, as shown in FIG. 1A, the first elastic force generation mechanism has a first compression spring 30 as a first elastic member connected between the base bottom portion 14 and the horizontal movement arm portion 16. This first compression spring 30 is elongated and elastically expand/contract in a central axis direction thereof. A lower end portion of the first compression spring 30 is pivoted on the base bottom portion 14. Moreover, the first compression spring 30 can revolve with respect to the base bottom portion 14 around a 13th rotation axis O13 extending in the substantially horizontal direction through the lower end portion of the first compression spring 30. That is, the lower end portion of the first compression spring is a fixed-side supporting point which does not change its position with respect to the base bottom portion 14.

On the other hand, an upper end portion of the first compression spring 30 is pivoted at an appropriate position between both end portions (the lower end portion and the upper end portion) of the first vertical link 16a. Additionally, the first compression spring 30 can revolve with respect to the first vertical link 16a around a 14th rotation axis O14 extending in the substantially horizontal direction through the upper end portion of the first compression spring 30. That is, the upper end portion of the first compression spring 30 is a moving-side supporting point which changes its position with respect to the base bottom portion 14 around the 13th rotation axis O13.

It is to be noted that the first compression spring 30 is substantially parallel to the first vertical link 16a and extended in the substantially vertical direction in the initial state.

The second elastic force generation mechanism has an L-shaped link member 34 which is built into the base bottom portion 14. An apex portion of a bent part of this link member 34 is pivoted on the base bottom portion 14 at substantially the same position as the lower end portion of the second vertical link 16b. Additionally, the link member 34 can revolve with respect to the base bottom portion 14 around the third rotation axis O3 extending in the substantially horizontal direction through the apex portion of the bent part. Two arms 34a and 34b are extended from the bent part of the link member 34. In the initial state, one arm 34a is extended in the substantially horizontal direction (the left direction in FIG. 1A).

A lower end portion of a rod-like first coupling link 40 is pivoted at an apex portion of an end part of one arm 34a. Further, the first coupling link 40 can revolve with respect to the link member 34 around a 15th rotation axis O15 extending in the substantially horizontal direction through the lower end part of the first coupling link 40. In the initial state, the first coupling link 40 is extended toward an upper side in the vertical direction (the upper direction in FIG. 1(A)) substantially parallel to the second vertical link 16b. It is to be noted that a length of the first coupling link 40 is substantially equal to a length of the second vertical link 16b.

A lower end portion of a rod-like second coupling link 42 is pivoted at an upper end portion of the first coupling link 40. Furthermore, the second coupling link 42 can revolve with respect to the first coupling link 40 around a 16th rotation axis O16 extending in the substantially horizontal direction through the lower end portion of the second coupling link 42. In the initial state, the second coupling link 42 is extended toward the upper side in the substantially vertical direction (the upper direction in FIG. 1(A)). It is to be noted that a length of the second coupling link 42 is substantially equal to a distance between the upper end portion of the second vertical link 16b (the fifth rotation axis O5) and the portion of the first horizontal link 20a adjoining one end portion thereof (the sixth rotation axis O6).

An upper end portion of the second coupling link 42 is pivoted at one end portion of the first horizontal link 20a of the vertical movement arm portion 20. Moreover, the first horizontal link 20a can revolve with respect to the second coupling link 42 around a 17th rotation axis O17 extending in the substantially horizontal direction through one end portion of the first horizontal link 20a.

Additionally, one end portion of a rod-like third coupling link 44 is pivoted at an upper end portion of the first coupling link 40. Further, the third coupling link 44 can revolve with respect to the first coupling link 40 around the 16th rotation axis O16 extending in the substantially horizontal direction through one end portion of the third coupling link 44. In the initial state, the third coupling link 44 is extended in the substantially horizontal direction (the left-and-right direction in FIG. 1(A)). It is to be noted that a length of the third coupling link 44 is substantially equal to a distance between an upper end portion of the second coupling link 42 (the 17th rotation axis O17) and the portion of the first horizontal link 20a adjoining one end portion thereof (the sixth rotation axis O6) and a distance between an apex portion of the bent portion of the link member 34 (the third rotation axis O3) and an apex portion of the end portion of one arm 34a (the 15th rotation axis O15).

The other end portion of the third coupling link 44 is pivoted at the upper end portion of the second vertical link 16b. Further, the third coupling link 44 can revolve with respect to the second vertical link 16b around the fifth rotation axis O5 extending in the substantially horizontal direction through the other end portion of the third coupling link 44.

The third, fifth, 16th and fifth rotation axes O3, O15, O16 and O5 are arranged at apex portions of a substantially parallelogram within a vertical plane, and stand a parallelogram state in an operation of the surgical microscope 10. Furthermore, this is also applied to the fifth, 16th, 17th and sixth rotation axes O5, O16, O17 and O6. Moreover, the perpendicular state of the second coupling link 42 and the third coupling link 44 is also held when the first and second vertical links 16a and 16b are respectively revolved with respect to the base bottom portion 14 around the rotation axes O2 and O3.

In this manner, the vertical movement arm portion 20 and the link member 34 are coupled through the first to third coupling links 40, 42 and 44. Additionally, a moment generated around the second horizontal rotation axis when the vertical movement arm portion 20 revolves around the second horizontal rotation axis (the sixth and seventh rotation axes O6 and O7) is transmitted to the link member 34 through the first to third coupling links 40, 42 and 44.

Here, in the initial state, the other arm 34b of the link member 34 is extended toward the lower side in the substantially vertical direction (the lower direction in FIG. 1A). One end portion (an upper end portion) of a second compression spring 36 as a second elastic member (also functioning as the first balance member) of a second elastic force generation mechanism (also serving as the first balance mechanism) is pivoted at an apex portion of the end portion of the other arm 34b. Furthermore, the second compression spring 36 can revolve with respect to the link member 34 around an 18th rotation axis O18 extending in the substantially horizontal direction through one end portion of the second compression spring 36. The other end portion (the lower end portion) of the second compression spring 36 is pivoted at the lower end portion of the base bottom portion 14. Additionally, the second compression spring 36 can revolve with respect to the base bottom portion 14 around a 19th rotation axis O19 extending in the substantially horizontal direction through the other end portion of the second compression spring 36.

The other end portion of the second compression spring 36 is a fixed-side supporting point whose position does not change with respect to the base bottom portion 14. On the other hand, one end portion of the second compression spring 36 is a moving-side supporting point which is moved with respect to the base bottom portion 14 with the other end portion of the second compression spring 36 (the 19th rotation axis O19) at the center. Further, when the link member 34 is revolved around the third rotation axis O3, one end portion of the second compression spring 36 is also revolved with respect to the base bottom portion 14 with the other end portion of the second compression spring 36 (the 19th rotation axis O19) at the center in accordance with this revolving movement.

Figure 1B:
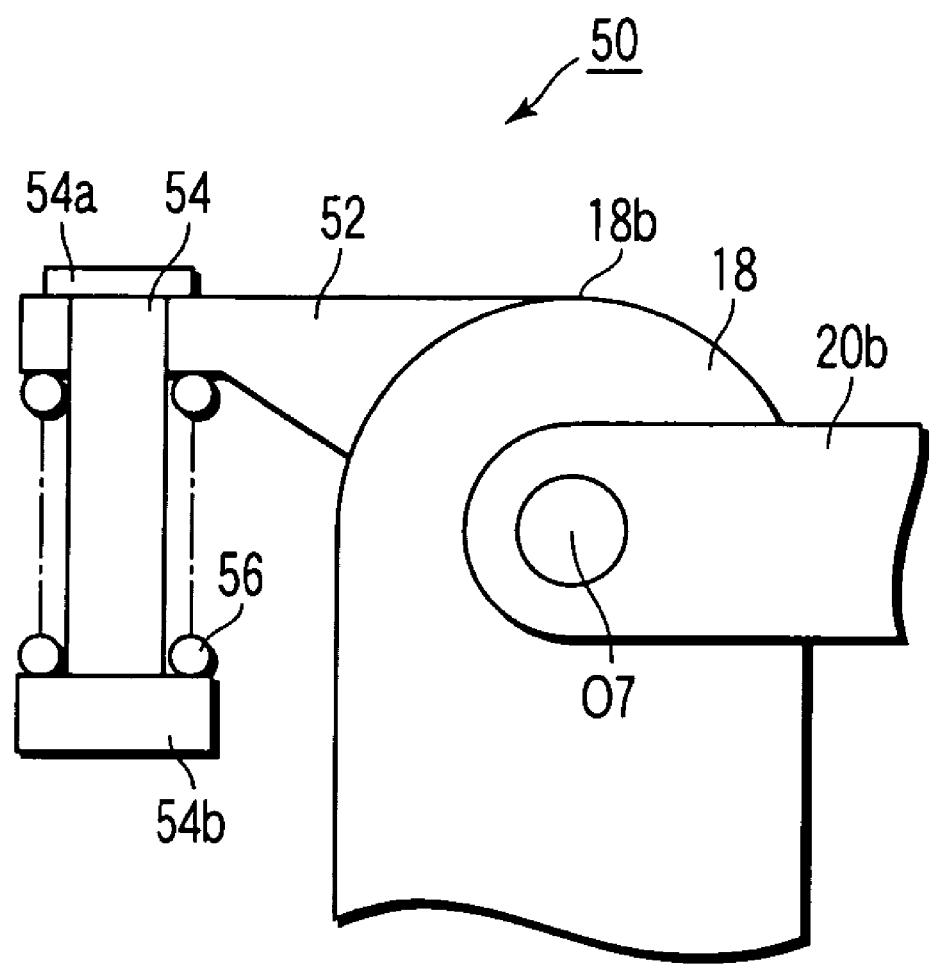
FIG. 1B is an enlarged view of an auxiliary balance mechanism of the surgical microscope according to the first embodiment of the present invention.

Furthermore, the auxiliary balance mechanism 50 is integrally formed with the joint portion 18. As shown in FIG. 1B, an extended portion 52 of the auxiliary balance mechanism 50 is extended from the upper end portion of the other arm 18b of the joint portion 18 in a direction (a left direction in FIG. 1B) opposite to the second horizontal link 20b. A shaft portion 54 is inserted into a through hole at an extended end portion of this extended portion 52. An axial direction of this shaft portion 54 substantially matches with the vertical direction, and the shaft portion 54 can slide with respect to the extended portion 52 in the axial direction (the vertical direction).

A first flange portion 54a is arranged at an upper end portion of the shaft portion 54, and the first flange portion 54a is supported by the extended portion 52, whereby the shaft portion 54 is suspended from the extended portion 52.

On the other hand, a second flange portion 54b is arranged at a lower end portion of the shaft portion 54. A third compression spring 56 as a second balance member is compressed and arranged between a lower surface of the extended portion 52 and an upper surface of the second flange portion 54a to be expandable/contractible along the axial direction (the vertical direction) of the shaft portion 54. That is, when a force advancing from the second flange portion 54b toward the first flange portion 54a along the axial direction is given to the second flange portion 54b, the third compression spring is compressed and the shaft portion 54 slides with respect to the extended portion 52 in the axial direction.

Here, referring to FIGS. 1A and 1B, the central axis of the second coupling link 42 extends in the vertical direction. An extended length of the extended portion 52 is selected in such a manner that the central axis of the shaft portion 54 substantially matches with the central axis of the second coupling link 42.

A function of the surgical microscope 10 having the above-mentioned structure according to this embodiment will now be described. First, referring to FIGS. 1A, 2A and 2B, a description will be given as to a case where the microscope portion 24 is moved in the horizontal direction (a left-and-right direction in FIGS. 1, 2A and 2B). It is to be noted that the illustration of the auxiliary balance mechanism 50 is eliminated in FIGS. 2A and 2B for the convenience's sake.

FIG. 1A shows the initial state of the surgical microscope 10 according to this embodiment. It is to be noted that the base 12 is fixed on a floor by operating stoppers of the casters 12a. The base bottom portion 14 can rotate around the first rotation axis O1 with respect to the base 12.

In the initial state of the surgical microscope 10, the first and second vertical links 16a and 16b are arranged in parallel with each other along the vertical direction. Further, the first and second horizontal links 20a and 20b are arranged parallel to each other along the horizontal direction.

Furthermore, the first and second coupling links 40 and 42 are arranged parallel to the second vertical link 16b, and the third coupling link 44 is arranged to be perpendicular to the second vertical link 16b. A straight line which is perpendicular to the third rotation axis O3 and the 15th rotation axis O15 of the link member 34 is arranged parallel to the first horizontal link 20a. Moreover, a straight line which is perpendicular to the third rotation axis O3 and the 15th rotation axis O15 of the link member 34 is arranged in parallel with the second vertical link 16b.

From this initial state, as shown in FIG. 2A, the microscope portion 24 is moved toward the left side with respect to the state shown in FIG. 1A. The vertical movement arm portion 20 is moved toward the left side in FIG. 2A while maintaining its shape in the initial state, and the joint portion 18 is also moved toward the left side in FIG. 2A. At this time, the upper end portions of the first and second vertical links 16a and 16b of the horizontal movement arm portion 16 are respectively revolved toward the left side in FIG. 2A around the second and third rotation axes O2 and O3 of the lower end portions. When the upper end portion of the second vertical link 16b is revolved toward the left side in FIG. 2A around the third rotation axis 3 with respect to the base bottom portion 14, the third coupling link 44 is also moved to the left side in FIG. 2A. Therefore, the first coupling link 40 is revolved toward the left side in FIG. 2A with respect to the link member 34 around the 15th rotation axis O15 of the lower end portion of the first coupling link 40.

When the first vertical link 16a is revolved with respect to the base bottom portion 14 around the second rotation axis O2 of the lower end portion, the first compression spring 30 whose upper end portion is pivoted on the first vertical link 16a is also revolved with respect to the base bottom portion 14 around the 13th rotation axis O13 of the lower end portion of the first compression spring 30. At this time, since the 14th rotation axis O14 of the upper end portion of the first compression spring 30 is arranged between the fourth rotation axis O4 and the second rotation axis O2 of the upper and lower end portions of the first vertical link 16a, whilst the 13th rotation axis O13 of the lower end portion of the first compression spring 30 is arranged below the second rotation axis O2 in the vertical direction, and hence the first compression spring 30 is compressed, and the central axis of the first vertical link 16a and the central axis of the first compression spring 30 form an angle $\alpha$.

Therefore, a reactive force $F(\alpha)$ which is a function of the angle $\alpha$ is generated in the first compression spring 30 along the central axis direction. A consideration will now be given on this reactive force $F(\alpha)$ by dividing it into a component in the central axis direction of the first vertical link 16a and a component force $Fv(\alpha)$ which is a component perpendicular to this central axis direction and the horizontal direction. A magnitude of this component force $Fv(\alpha)$ is determined based on a magnitude of the reactive force $F(\alpha)$ of the first compression spring 30 and the angle $\alpha$ formed between the first vertical link 16a and the first compression spring 30.

A moment around the second rotation axis O2 generated by the first compression spring 30 can be obtained by multiplying a distance between the second rotation axis O2 and the 14th rotation axis O14 on which the component force $Fv(\alpha)$ acts by the magnitude of the component force $Fv(\alpha)$. This moment is changed when the component force $Fv(\alpha)$ varies with a change in the angle $\alpha$.

On the other hand, a moment around the second rotation axis O2 functions with respect to the first vertical link 16a by weights of the microscope portion 24, the end joint portion 22, the vertical movement arm portion 20, the joint portion 18 and the horizontal movement arm portion 16, or the like. This moment is also a function of the angle $\alpha$.

Here, the moment around the second rotation axis O2 generated by the first compression spring 30 functions to offset the moment around the second rotation axis O2 generated by a weight of the microscope portion 24, or the like. Further, the spring strength of the first compression spring 30 and the arrangement of the first compression spring 30 and the first vertical link 16a are selected in such a manner that the two moments are balanced with respect to the substantially whole change in the angle $\alpha$.

Therefore, even if the microscope portion 24 is moved in the horizontal direction (the left direction in FIGS. 1A and 2A) to be revolved around the second and third rotation axes O2 and O3, the surgical microscope 10 is balanced by the rotation moment generated by the first compression spring 30. Accordingly, in case of moving the microscope portion 24 in the horizontal direction (the left direction in FIGS. 1A and 2A), the microscope portion 24 can be moved with a light force.

Figure 2B:
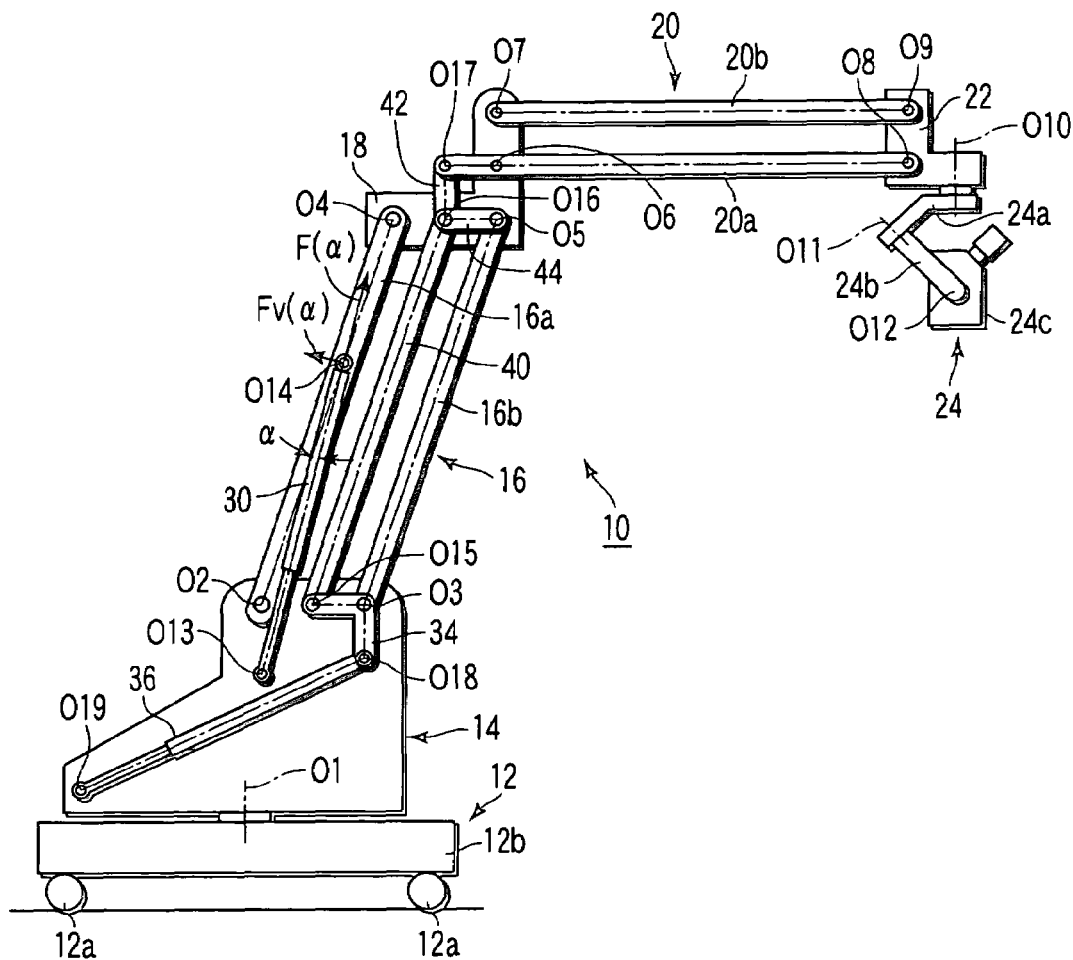
FIG. 2B is a schematic view showing the surgical microscope according to the first embodiment of the present invention in a state where the microscope portion is moved toward a right side in the horizontal direction in the page space.

Next, from the initial state, as shown in FIG. 2B, the microscope portion 24 is moved toward the right side with respect to the state shown in FIG. 1A. The surgical microscope 10 is balanced like the case where the microscope portion 24 is moved toward the left side from the initial state as shown in FIG. 2A.

It is to be noted that, in the initial state where the first vertical link 16a is arranged in the vertical direction shown in FIG. 1A, the moment around the second rotation axis O2 generated by a weight of the microscope portion 24, or the like becomes zero. Furthermore, the moment around the second rotation axis O2 generated by the first compression spring 30 also becomes zero.

Therefore, the microscope portion 24 can be moved to an arbitrary position in the horizontal direction with a light force by revolving the horizontal movement arm portion 16 around the first horizontal rotation axis (the second and third rotation axes O2 and O3).

A description will now be given as to an example where the microscope portion 24 is moved in the vertical direction (the up-and-down direction in FIGS. 3A, 3B and 4) with reference to FIGS. 3A, 3B and 4. As shown in FIG. 3A, from the initial state, the microscope portion 24 is moved up with respect to the state shown in FIG. 1A.

When the microscope portion 24 is moved up, the end joint portion 22 is moved up in accordance with this upward movement. At this time, the other end portions of the first and second horizontal links 20a and 20b are moved up together with the end joint portion 22, and the first and second horizontal links 20a and 20b are respectively revolved around the sixth and seventh rotation axes O6 and O7 with respect to the joint portion 18. At this time, one end portion of the first horizontal link 20a (a left end part in FIG. 3A) is moved down along the vertical direction with the sixth rotation axis O6 at the center.

As a result, the second coupling link 42 whose upper end portion is pivoted at one end portion of the first horizontal link 20a is moved down along the vertical direction. When the second coupling link 42 is moved down in the vertical direction, the first coupling link 40 whose upper end portion is pivoted at the lower end portion of the second coupling link 42 is moved down in the vertical direction. When the first coupling link 40 is moved down in the vertical direction, the end portion of the arm 34a of the link member 34 which is pivoted at the lower end portion of the first coupling link 40 is also moved down in the vertical direction. As a result, the link member 34 is revolved around the third rotation axis O3 with respect to the base bottom portion 14.

When the link member 34 is revolved around the third rotation axis O3, the second compression spring 36 whose one end portion is pivoted at the end portion of the arm 34b of the link member 34 is also revolved around the 19th rotation axis O19 of the other end portion of the second compression spring 36 with respect to the base bottom portion 14. As a result, the second compression spring 36 is expanded, and an angle $\beta$ formed between the central axis of the second compression spring 36 and the a straight line perpendicular to the third rotation axis O3 and the 18th rotation axis O18 of the link member 34 is changed.

Therefore, a reactive force $F(\beta)$ which is a function of the angle $\beta$ is generated in the second compression spring 36 along the central axis direction. A consideration will now be given as to this reactive force $F(\beta)$ by dividing it into a component in a straight line direction perpendicular to the third rotation axis O3 and the 18th rotation axis O18 of the link member 34 and a component force $Fv(\beta)$ which is a component perpendicular to this straight line direction and the horizontal direction. A magnitude of this component force $Fv(\beta)$ is determined based on a magnitude of the reactive force $F(\beta)$ of the second compression spring 36 and an angle β formed between the central axis of the second compression spring 36 and the straight line perpendicular to the third rotation axis O3 and the 18th rotation axis O18 of the link member 34.

A moment around the third rotation axis O3 generated by the second compression spring 36 is obtained by multiplying a distance between the third rotation axis O3 and the 18th rotation axis O18 on which the component force Fv(β) acts by the component force Fv(β). This moment is changed when the component force Fv(β) varies with a change in the angle β.

On the other hand, a moment around the third rotation axis O3 is generated in the link member 34 by weights of the microscope portion 24, the end joint portion 22, the vertical movement arm portion 20 and the first to third coupling links 40, 42 and 44, or the like. This moment is also a function of the angle β.

Here, the moment around the third rotation axis O3 generated by the second compression spring 36 functions to offset the moment around the third rotation axis O3 generated by a weight of the microscope portion 24, or the like. Moreover, the spring strength of the second compression spring 36 and the arrangement of the first to third coupling links 40, 42 and 44, the link member 34 and the second compression spring 36 are selected in such a manner that the two moments are balanced with respect to the substantially whole change in the angle β.

Therefore, even if the microscope portion 24 is moved up along the vertical direction (the upper direction in FIGS. 1A and 3A) to be revolved around the sixth and seventh rotation axes O6 and O7, the surgical microscope 10 is balanced by the rotation moment generated by the second compression spring 36. Therefore, in case of moving up the microscope portion 24 in the vertical direction (the upper direction in FIGS. 1A and 3A), the microscope portion 24 can be moved with a light force.

Next, from the initial state, as shown in FIG. 3B, the microscope portion 24 is moved down with respect to the state shown in FIG. 1A. The surgical microscope 10 can be balanced like the example where the microscope portion 24 is moved up from the initial state as shown in FIG. 3A.

For example, when the microscope portion 24 is continuously moved from the state shown in FIG. 3A to the state depicted in FIG. 3B, the moment around the third rotation axis O3 generated by a weight of the microscope portion 24, or the like is offset by the moment around the third rotation axis O3 generated by the second compression spring 36. That is, the angle β formed between the central axis of the second compression spring 36 and the straight line direction perpendicular to the third rotation axis O3 and the 18th rotation axis O18 of the link member 34 is changed, the component force Fv(β) of the reactive force F(β) of the second compression spring 36 is changed, and the moment generated by the second compression spring 36 is changed to offset the rotation moment around the third rotation axis O3 produced by weights of the microscope portion 24, the end joint portion 22, the vertical movement arm portion 20 and the first to third coupling links 20, 42 and 44, or the like.

Meanwhile, as shown in FIG. 3B, when a revolving range of the vertical movement arm portion 20 is set to be relatively large, the angle β formed between the straight line perpendicular to the third rotation axis O3 and the 18th rotation axis O18 of the link member 34 and the central axis of the second compression spring 36 becomes small in the vicinity of a lower end portion of the revolving range, and the component force Fv(β) is reduced. In this case, the component force Fv(β) of the reactive force F(β) of the second compression spring 36 becomes insufficient, and it is difficult to offset the moment around the third rotation axis O3 generated by a weight of the microscope portion 24, or the like. In order to compensate such insufficiency of the moment by the second elastic force generation mechanism as the first balance mechanism, a reactive force obtained by the third compression spring 56 of the second balance mechanism is utilized.

Figure 4:
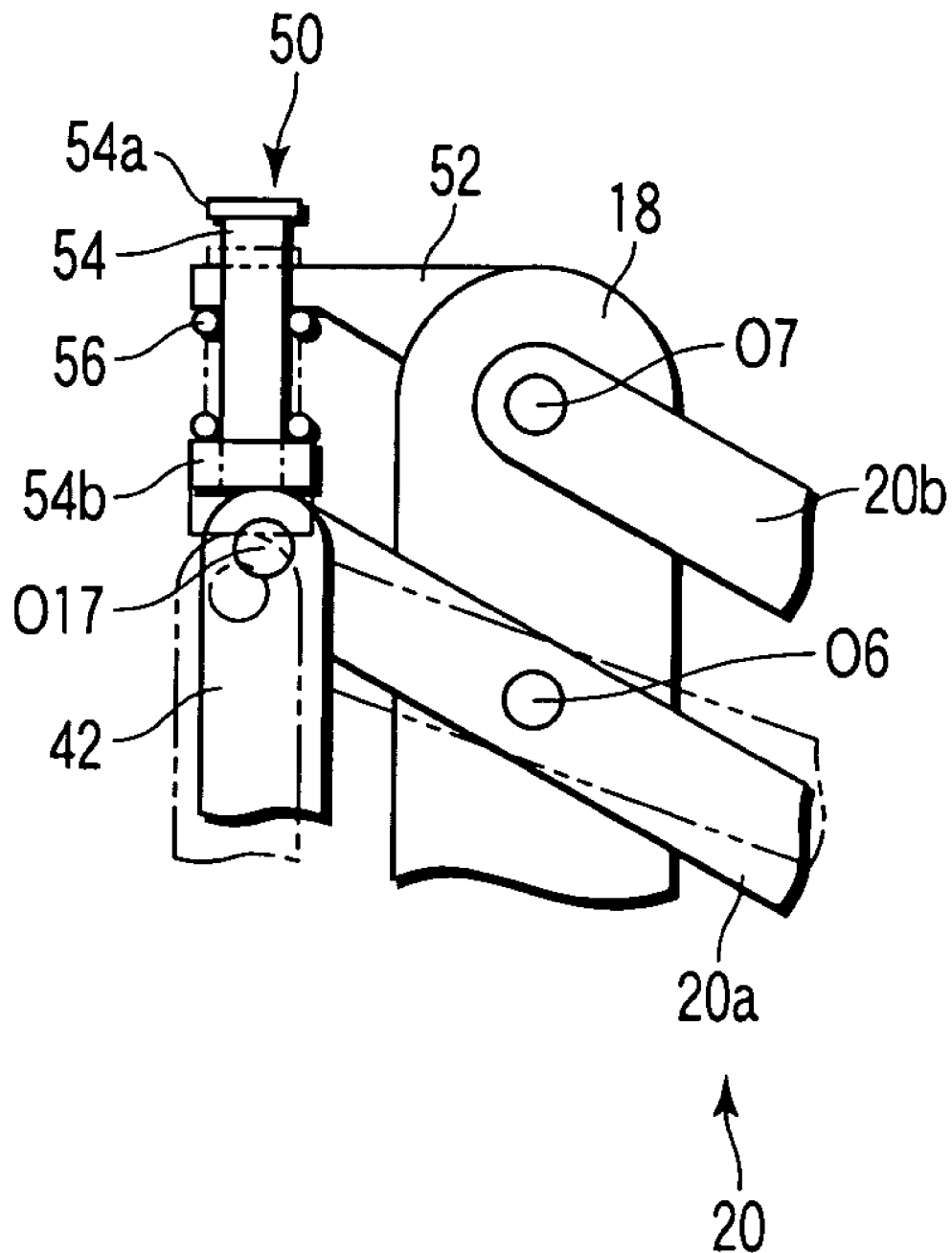
FIG. 4 is a schematic view showing the auxiliary balance mechanism and a second coupling link of the surgical microscope according to the first embodiment of the present invention in a state where the microscope portion is moved toward the lower side in is the vertical direction in the page space whereby the second coupling link is brought into contact with the auxiliary balance mechanism.

As shown in FIGS. 3 and 4, when the microscope portion 24 is moved toward the lower side and the first horizontal link 20a is revolved around the sixth rotation axis O6 with respect to the joint portion 18, the upper end portion of the second coupling link 42 comes into contact with the second flange portion 54b of the shaft portion 54 of the auxiliary balance mechanism 50 as indicated by a chain double-dashed line in FIG. 4. When the microscope portion 24 is further moved toward the lower side and the first horizontal link 20a is further revolved, the second coupling link 42 pushes up the second flange portion 54b and is moved up while compressing the third compression spring 56. Therefore, the reactive force of the third compression spring 56 functions with respect to the link member 34 by the second flange portion 54b, the second coupling link 42 and the first coupling link 40, thereby compensating insufficiency of the moment by the second compression spring 36.

Therefore, even if the microscope portion 24 is moved down in the vertical direction (the lower direction in FIGS. 1A and 3A) to be revolved around the sixth and seventh rotation axes O6 and O7, the surgical microscope 10 is balanced by the rotation moment generated by the second and third compression springs 36 and 56. Accordingly, in case of moving down the microscope portion 24 in the vertical direction (the lower direction in FIGS. 1A and 3A), the microscope portion 24 can be moved with a light force.

Therefore, the microscope portion 24 can be moved to an arbitrary position in the vertical direction with a light force by a revolving movement of the vertical movement arm portion 20 around the second horizontal rotation axis (the sixth and seventh rotation axes O6 and O7).

The observation direction of the binocular tube 24c can be three-dimensionally arbitrarily moved and inclined by the movement of the microscope portion 24 in the horizontal direction by the horizontal movement arm portion 16, the movement of the microscope portion 24 in the vertical direction by the vertical movement arm portion 20 and the rotation of the binocular tube 24c of the microscope portion 24 around the 10th to 12th rotation axes O10, O11 and O12. An operator arbitrarily moves and inclines the binocular tube 24 to observe a desired part of a patient.

Therefore, the surgical microscope 10 having the above-described structure demonstrates the following effects.

In case of moving the microscope portion 24 in the horizontal direction, the horizontal movement arm portion 16 is revolved around the first horizontal rotation axis (the second and third rotation axes O2 and O3) with respect to the base bottom portion 14. At this time, the rotation moment generated around the second rotation axis O2 by weights of the microscope portion 24, the end joint portion 22, the vertical movement arm portion 20, the joint portion 18 and the horizontal movement arm portion 16, or the like is offset by the first elastic force generation mechanism connected between the horizontal movement arm portion 16 and the base bottom portion 14.

Further, in case of moving the microscope portion 24 in the vertical direction, the vertical movement arm portion 20 is revolved around the second horizontal rotation axis (the sixth and seventh rotation axes O6 and O7) with respect to the joint portion 18. At this time, the rotation moment generated around the third rotation axis O3 by weights of the microscope portion 24, the end joint portion 22, the vertical movement arm portion 20, the joint portion 18 and the first to third coupling links 40, 42 and 44, or the like is offset by the second elastic force generation mechanism connected between the vertical movement arm portion 20 and the base bottom portion 14.

As described above, the microscope portion 24 can be moved with a light force, and the first and second elastic force generation mechanisms are not directly arranged in the vertical movement arm portion 20, thereby realizing a reduction in size and weight of the surgical microscope 10. Therefore, the operability of the surgical microscope 10 is improved.

Furthermore, in case of moving the microscope portion 24 in the vertical direction, the rotation moment generated around the third rotation axis O3 by a weight of the microscope portion 24, or the like is offset by the second elastic force generation mechanism which is connected between the vertical movement arm portion 20 and the base bottom portion 14 and also serves as the first balance mechanism. Moreover, in case of greatly moving down the microscope portion 24, the imbalance of the rotation moment generated around the third rotation axis O3 by a weight of the microscope portion 24, or the like and the rotation moment produced around the third rotation axis O3 by the second elastic force generation mechanism is corrected by the reactive force of the third compression spring 56 of the auxiliary balance mechanism 50. Therefore, even in case of moving the microscope portion 24 in a wide range along the vertical direction, the microscope portion 24 can be operated with a light force, thus improving the operability of the surgical microscope 10.

It is to be noted that the moment around the second horizontal rotation axis (the sixth and seventh rotation axes O6 and O7) of the vertical movement arm portion 20 is transmitted to the link member 34 by using the first to third coupling links 40, 42 and 44 in this embodiment, but the same effect can be obtained by using a flexible transmission member such as a wire or belt in place of the coupling links 40, 42 and 44.

FIGS. 5A to 8 show a second embodiment according to the present invention. Like reference numerals denote structures having the same functions as those in the first embodiment, thereby eliminating their explanation. Here, a description will be given as to a surgical microscope 10 in an initial state depicted in FIG. 5 in which a later-described horizontal movement arm portion 62 is extended in the vertical direction and a vertical movement arm portion 66 is extended in the horizontal direction.

Figure 5A:
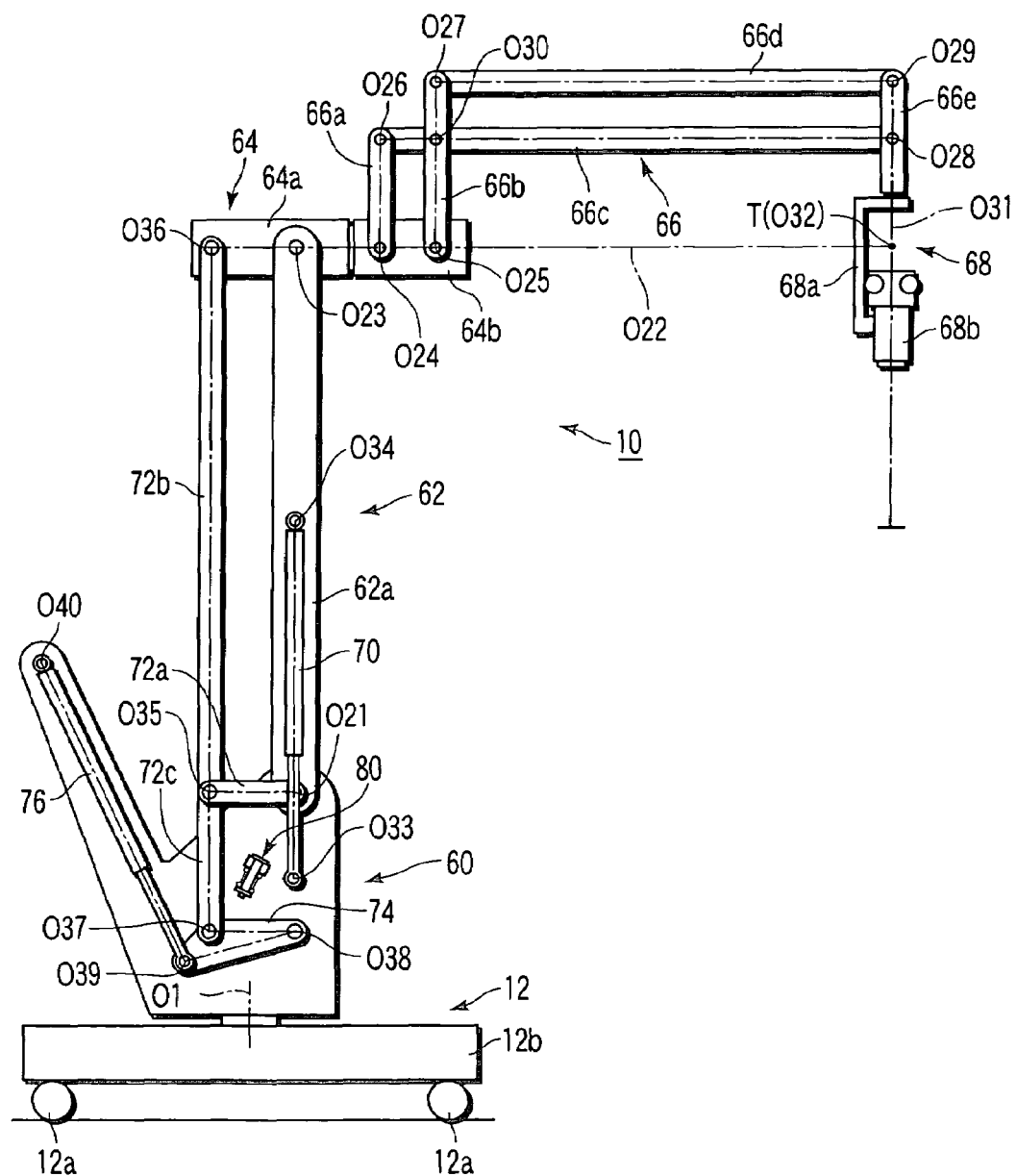
FIG. 5A is a side view showing an outline structure of a surgical microscope according to a second embodiment of the present invention.

As shown in FIG. 5A, the surgical microscope 10 according to this embodiment has a base 12, a base bottom portion 60, a horizontal movement arm portion 62, an arm support portion 64 (corresponding to the joint portion 18 (see FIG. 1A) according to the first embodiment), a vertical movement arm portion 66 and a microscope portion 68 like the first embodiment.

A lower end portion of a vertical link 62a of the horizontal movement arm portion 62 is pivoted on an upper part of the base bottom portion 60. Additionally, the vertical link 62s can revolve with respect to the base bottom portion 60 around a 21st rotation axis O21 as a first horizontal rotation axis extending in a substantially horizontal direction through the lower end portion of the vertical link 62a. The vertical link 62a has a rod-like shape, and is extended in the vertical direction in the initial state.

That is, the horizontal movement arm portion 62 can revolve around the first horizontal rotation axis arranged in the base bottom portion 60.

An upper end portion of the vertical link 62a is connected with the arm support portion 64. Here, the arm support portion 64 has cylindrical first and second connection blocks 64a and 64b coupled with each other along a central axis direction. The upper end portion of the vertical link 62a is pivoted at an end portion of the first connection block 64a on the second connection block 64b side. Further, the arm support portion 64 can revolve with respect to the vertical link 62a around a 23rd rotation axis O23 as a second horizontal rotation axis extending in the substantially horizontal direction through the upper end portion of the vertical link 62a.

The second connection block 64b can rotate around a central axis thereof with respect to the first connection block 64. Here, a 22nd rotation axis O22 is substantially perpendicular to a first rotation axis O1 and the 21st rotation axis O21.

Lower end portions of first and second movable links 66a and 66b of the vertical movement arm portion 66 are connected with the second connection block 64b. The lower end portion of the first movable link 66a is pivoted at an end portion of the second connection block 64b on the first connection block 64a side, and the lower end portion of the second movable link 66b is pivoted at an end portion on an opposite side. Furthermore, the first movable link 66a can revolve with respect to the second connection block 64b around a 24th rotation axis O24 extending in the substantially horizontal direction through the lower end portion of the first movable link 66a. Furthermore, the second movable link 66b can revolve with respect to the second connection block 64b around a 25th rotation axis O25 extending in the substantially horizontal direction through the lower end portion of the second movable link 66b.

The first and second movable links 66a and 66b have a rod-like shape, and are extended in parallel with each other along the vertical direction in the initial state. Moreover, the second movable link 66b is longer than the first movable link 66a.

On end portion (a left end part in FIG. 5A) of a third movable link 66c is pivoted at an upper end portion of the first movable link 66a. Additionally, the third movable link 66c can revolve with respect to the first movable link 66a around a 26th rotation axis O26 extending in the substantially horizontal direction through one end portion of the third movable link 66c. Further, one end portion (a left end part in FIG. 5A) of a fourth movable link 66d is pivoted at an upper end portion of the second movable link 66b. Furthermore, the fourth movable link 66d can revolve with respect to the second movable link 66b around a 27th rotation axis O27 extending in the substantially horizontal direction through one end portion of the fourth movable link 66d.

The third and fourth movable links 66c and 66d have a rod-like shape, and are extended parallel to each other along the same horizontal direction (a right direction in FIG. 5A) in the initial state. Moreover, the other end portions (a right end part in FIG. 5A) of the third and fourth movable links 66c and 66d are arranged at substantially the same positions with respect to the horizontal direction in the initial state.

It is to be noted that the third movable links 66c is pivoted on the second movable link 66b at its crossing portion with respect to the second movable link 66b. Additionally, the third movable link 66c can revolve with respect to the second movable link 66b around a 30th rotation axis O30 extending in the substantially horizontal direction through the crossing portion with respect to the second movable link 66b.

An upper end portion of a fifth movable link 66e is pivoted at the other end portion of the fourth movable link 66d. Further, the fifth movable link 66e can revolve with respect to the fourth movable link 66d around a 29th rotation axis O29 extending in the substantially horizontal direction through the other end portion of the fifth movable link 66e. Furthermore, the other end portion of the third movable link 66e is pivoted at a central part of the fifth movable link 66e. Moreover, the fifth movable link 66e can revolve with respect to the third movable link 66c around a 28th rotation axis O28 extending in the substantially horizontal direction through the central part of the fifth movable link 66e.

Here, the 24th, 25th, 30th and 26th rotation axes O24, O25, O30 and O26 are arranged at apex portions of a parallelogram within a vertical plane. Additionally, a distance between the 29th rotation axis O29 and the 28th rotation axis O28 of the fifth movable link 66e is substantially equal to a distance between the 27th rotation axis O27 and the 30th rotation axis O30 of the second movable link 66b. Therefore, the 27th, 30th, 28th and 29th rotation axes O27, O30, O28 and O29 are arranged at apex portions of a parallelogram within a vertical plane. Therefore, the first, second and fifth movable links 66a, 66b and 66e stay parallel to each other and the third and fourth movable links 66c and 66d also stay parallel to each other in an operation of the surgical microscope 10.

An upper end portion of a first arm 68a of the microscope portion 68 is pivoted at the lower end portion of the fifth movable link 66e. Further, the first arm 68a can rotate with respect to the fifth movable link 66e around a 31st rotation axis O31 extending in the substantially vertical direction through the upper end portion of the first arm 68a. A binocular tube 68b is arranged at a lower end portion of the first arm 68a. A central axis of the binocular tube 68b substantially matches with the 31st rotation axis O31.

That is, the binocular tube 68b rotates around the 31st rotation axis O31 by rotation of the first arm 68a around the 31st rotation axis O31 with respect to the fifth movable link 66e. Furthermore, the binocular tube 38b is revolved around the 22nd rotation axis O22 by rotation of the arm support portion 64 around the 22nd rotation axis O22 of the second connection block 64b with respect to the first connection block 64a. Moreover, the binocular tube 68b is revolved around a 32nd rotation axis O32 perpendicular to both the 22nd rotation axis O22 and the 31st rotation axis O31 through an intersecting point T of both the rotation axes by operations of the first to fifth movable links 66a, . . . , 66e of the vertical movement arm portion 66. The binocular tube 68b of the microscope portion 68 is inclined by the revolving movements around these 22nd, 31st and 32nd rotation axes O22, O31 and O32.

It is to be noted that a weight is distributed in the surgical microscope 10 in such a manner that rotation moments around the 22nd rotation axis O22, the 31st rotation axis O31 and the 32nd rotation axis O32 always become zero. Therefore, the binocular tube 68b can be inclined in a state where the balance of the surgical microscope 10 is redressed.

Accordingly, the microscope portion 68 can move in the substantially horizontal direction (the substantially left-and-right direction in FIG. 1A) by the revolving movement of the horizontal movement arm portion 62 around the first horizontal rotation axis (the 21st rotation axis O21), and can move in the substantially vertical direction (the substantially up-and-down direction in FIG. 1A) by the revolving movement of the vertical movement arm portion 66 around the second horizontal rotation axis (the 23rd rotation axis O23) of the vertical movement arm portion 66. Additionally, the binocular tube 68b of the microscope portion 68 can be inclined by the revolving movements around the 22nd, 31st and 32nd rotation axes O22, O31 and O32.

The surgical microscope 10 according to this embodiment has a first elastic force generation mechanism, a second elastic force generation mechanism (also serving as the first balance mechanism) and an auxiliary balance mechanism 80 as a second balance mechanism.

Giving a detailed description, as shown in FIG. 5A, the first elastic force generation mechanism has a first gas spring 70 as a first elastic member connected between the base bottom portion 60 and the horizontal movement arm portion 62. This first gas spring 70 is elongated and can elastically expand/contract along a central axis direction. A lower end portion of the first gas spring 70 is pivoted on the base bottom portion 60. Further, the first gas spring 70 can revolve with respect to the base bottom portion 60 around a 33rd rotation axis O33 extending in the substantially horizontal direction through the lower end portion of the first gas spring 70. A lower end portion of the first gas spring 70 is a fixed-side supporting point whose position does not change with respect to the base bottom portion 60.

On the other hand, an upper end portion of the first gas spring 70 is pivoted at an appropriate position between both end portions (the lower end portion and the upper end portion) of the vertical link 62a. Furthermore, the first gas spring 70 can revolve with respect to the vertical link 62a around a 34th rotation axis O34 extending in the substantially horizontal direction through the upper end portion of the first gas spring 70. That is, the upper end portion of the first gas spring 70 is a moving-side supporting point whose position changes with respect to the base bottom portion 60 with the 33rd rotation axis O33 at the center.

It is to be noted that the first gas spring 70 is substantially parallel with the vertical link 62a and extended in the substantially vertical direction in the initial state.

The second elastic force generation mechanism has a first coupling link 72a. One end portion (a right end part in FIG. 5A) of this first coupling link 72a is pivoted on the base bottom portion 60 at substantially the same position as the lower end portion of the vertical link 62a. Moreover, the first coupling link 72a can revolve with respect to the base bottom portion 60 around the 21st rotation axis O21 extending in the substantially horizontal direction through one end portion of the first coupling link 72a.

A lower end portion of the second coupling link 72b is pivoted at the other end portion (the left end part in FIG. 5A) of the first coupling link 72a. Additionally, the second coupling link 72b can revolve with respect to the first coupling link 72a around a 35th rotation axis O35 extending in the substantially horizontal direction through the lower end portion of the second coupling link 72b. In the initial state, the second coupling link 72b is extended parallel to the vertical link 62a along the substantially vertical direction.

An upper end portion of the second coupling link 72b is pivoted at the end portion of the first connection block 64a of the arm support portion 64 on the opposite side of the second connection block 64b. Further, the first connection block 64a can revolve with respect to the second coupling link 72b around a 36th rotation axis O36 extending in the substantially horizontal direction through the end portion of the first connection block 64a on the opposite side of the second connection block 64b.

Furthermore, an upper end portion of a third coupling link 72c is pivoted at the other end portion (the left end part in FIG. 5A) of the first coupling link 72a. Moreover, the third coupling link 72c can revolve with respect to the first coupling link 72a around the 35th rotation axis O35 extending in the substantially horizontal direction through the upper end portion of the third coupling link 72c. In the initial state, the third coupling link 72c is extended in the vertical direction to elongate the second coupling link 72b.

The 21st, 23rd, 36th and 35th rotation axes O21, O23, O36 and O35 are arranged at apex portions of a parallelogram in a vertical plane. Additionally, the vertical link 62a and the second coupling link 72b are held parallel in an operation of the surgical microscope 10.

A link member 74 is connected with a lower end portion of the third coupling link 72c. This link member 74 has a triangular shape, and a first apex portion thereof is pivoted at the lower end portion of the third coupling link 72c. Further, the link member 74 can revolve with respect to the third coupling link 72c around a 37th rotation axis O37 extending in the substantially horizontal direction through the first apex portion.

A second apex portion of the link member 74 is pivoted on the base bottom portion 60 below the lower end portion of the vertical link 62a along the substantially vertical direction. Further, the link member 74 can revolve with respect to the base bottom portion 60 around a 38th rotation axis O38 extending in the substantially horizontal direction through the second apex portion. A straight line perpendicular to the 37th rotation axis O37 and the 38th rotation axis O38 of the link member 74 and a straight line perpendicular to the 35th rotation axis O35 and the 21st rotation axis O21 of the first coupling link 72a are held substantially parallel to each other.

A lower end portion of a second gas spring 76 as a second elastic member (also serving as a first balance member) is pivoted at a third apex portion of the link member 74. Furthermore, the second gas spring 76 can revolve with respect to the link member 74 around a 39th rotation axis O39 extending in the substantially horizontal direction through a lower end portion of the second gas spring 76.

Moreover, an upper end portion of the second gas spring 76 is pivoted at an upper part of the base bottom portion 60. Additionally, the second gas spring 76 can revolve with respect to the base bottom portion 60 around a 40th rotation axis O40 extending in the substantially horizontal direction through the upper end portion of the second gas spring 76. It is to be noted that the second gas spring 76 is arranged in an accommodation portion having a protruding shape. A moving handle which is held and operated by an operator when moving the surgical microscope 10 by casters 12a is arranged on the outer side of this accommodation portion.

Figure 5B:
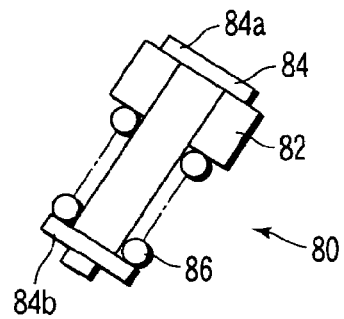
FIG. 5B is an enlarged view showing an auxiliary balance mechanism of the surgical microscope according to the second embodiment of the present invention.

An auxiliary balance mechanism 80 is arranged on the base bottom portion 60. As shown in FIGS. 5A and 5B, this auxiliary balance mechanism 80 has an annular spring base 82 fixed on the base bottom portion 60. A shaft portion 84 is inserted in an inner cavity of this spring base 82 in such a manner that it can slide along a central axis direction of the spring base 82. A central axis direction of the shaft portion 84 is substantially equal to the central axis direction of the spring base 82. First and second flange portions 84a and 84b are respectively arranged at both end portions of the shaft portion 84. The spring base 82 is arranged between the first flange portion 84a and the second flange portion 84b. Additionally, a compression spring 86 as a second balance member is compressed and arranged between the second flange portion 84b and the spring base 82, and the first flange portion 84a is brought into contact with and supported on the spring base 82 by a reactive force of the compression spring 86.

The auxiliary balance mechanism 80 is arranged above the link member 74, and the second flange portion 84b faces the link member 74. A central axis of the shaft portion 84 of the auxiliary balance mechanism 80 is arranged within a substantially vertical plane, and forms a predetermined angle with the first rotation axis O1 extending in the vertical direction.

A function of the surgical microscope 10 having the above-mentioned structure according to this embodiment will now be described. First, a description will be given as to an example in which the microscope portion 68 is moved in the horizontal direction (a left-and-right direction in FIGS. 5A, 6A and 6B) with reference to FIGS. 5A, 6A and 6B. It is to be noted that the illustration of the auxiliary balance mechanism 80 is eliminated in FIGS. 6A and 6B for the convenience's sake.

FIG. 5A shows an initial state of the surgical microscope 10 according to this embodiment. The base 12 is fixed on a floor by operating stoppers of the casters 12a. The base bottom portion 60 can rotate around the rotation axis O1 with respect to the base 12.

In the initial state, the vertical link 62a is arranged in the vertical direction, and the first gas spring 70 is arranged parallel to the vertical link 62a along the vertical direction. Further, the first coupling link 72a is arranged to be perpendicular to the vertical link 62a, and the second and third coupling links 72b and 72c are arranged parallel to the vertical link 62a along the vertical direction.

The first, second and fifth movable links 66a, 66b and 66e are arranged in the vertical direction, and the third and fourth movable links 66c and 66d are arranged in the horizontal direction.

Figure 6A:
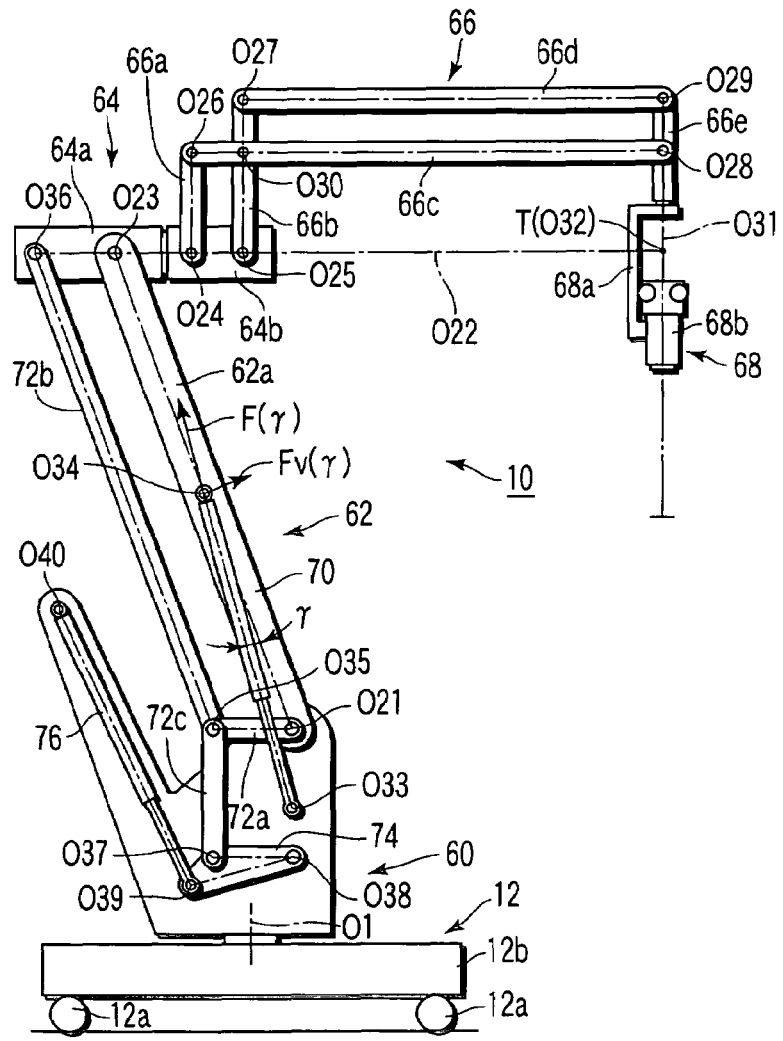
FIG. 6A is a schematic view showing the surgical microscope according to the second embodiment of the present invention in a state where a microscope portion is moved toward a left side in a horizontal direction in a page space.

From this initial state, as shown in FIG. 6A, the microscope portion 68 is moved toward the left side with respect to the state shown in FIG. 5A. The vertical movement arm portion 66 is moved toward the left side in FIG. 6A while maintaining a shape in the initial state. The second connection block 64b on which the lower end portions of the first and second movable links 66a and 66b are pivoted is also moved toward the left side in FIG. 6A. At this time, since the vertical movement arm portion 66 maintains the shape in the initial state, the arm support portion 64 is not inclined around the second horizontal rotation axis (the 23rd rotation axis O23). That is, the entire arm support portion 64 is moved toward the left side in FIG. 6A while maintaining the horizontal state.

When the entire arm support portion 64 is moved toward the left side in FIG. 6A, the vertical link 62a whose upper end portion is pivoted on the arm support portion 64 is revolved with respect to the base bottom portion 60 around the 21st rotation axis of the lower end portion of the vertical link 62a. Furthermore, the second coupling link 72b whose upper end portion is pivoted on the arm support portion 64 is also revolved with respect to the first coupling link 72a around the 35th rotation axis O35 of the lower end portion of the third coupling link 72c. Since the 21st, 23rd, 36th and 35th rotation axes O21, O23, O36 and O35 are arranged at apex portions of a parallelogram within a vertical plane, the vertical link 62a and the second coupling link 72b are revolved while maintaining a parallel state.

When the vertical link 62a is revolved with respect to the base bottom portion 60 around the 21st rotation axis O21 at the lower end portion, the first gas spring 70 whose upper end portion is pivoted on the vertical link 62a is also revolved with respect to the base bottom portion 60 around the 33rd rotation axis O33 of the lower end portion of the first gas spring 70. At this time, since the 34th rotation axis O34 of the upper end portion of the first gas spring 70 is arranged between the 23rd rotation axis O23 and the 21st rotation axis O21 of the upper and lower end portions of the vertical link 62a and the 33rd rotation axis O33 of the lower end portion of the first gas spring 70 is arranged below the 21st rotation axis O21 along the vertical direction, the first gas spring 70 is compressed, and the central axis of the vertical link 62a and the central axis of the first gas spring 70 form an angle γ.

Therefore, a reactive force F(γ) which is a function of the angle γ is generated in the first gas spring 70 along the central axis direction. A consideration will now be given as to this reactive force F(γ) by dividing it into a component in the central axis direction of the vertical link 62a and a component force Fv(γ) which is a component perpendicular to the central axis direction and the horizontal direction. A magnitude of this component force Fv(γ) is determined based on a magnitude of the reactive force F(γ) of the first gas spring 70 and the angle γ formed between the vertical link 62a and the first gas spring 70.

A moment around the 21st rotation axis O21 generated by the first gas spring 70 can be obtained by multiplying a distance between the 21st rotation axis O21 and the 34th rotation axis O34 on which the component force Fv(γ) acts by the magnitude of the component force Fv(γ). This moment is changed when the component force Fv(γ) varies with a change in the angle γ.

On the other hand, a moment around the 21st rotation axis O21 is generated in the vertical link 62a by weights of the microscope portion 68, the vertical movement arm portion 66, the arm support portion 64 and the horizontal movement arm portion 62, or the like. This moment is also a function of the angle γ.

Here, the moment around the 21st rotation axis O21 generated by the first gas spring 70 functions to offset the moment around the 21st rotation axis O21 produced by a weight of the microscope portion 68, or the like. Moreover, the spring strength of the first gas spring 70 and the arrangement of the first gas spring 70 and the first vertical link 62 are selected in such a manner that the two moments are balanced in accordance with the substantially whole change in the angle γ.

Therefore, even if the microscope portion 68 is moved in the horizontal direction (the left direction in FIGS. 5A and 6A) to be revolved around the 21st rotation axis O21, the balance of the surgical microscope 10 is redressed by the rotation moment generated by the first gas spring 70. Accordingly, in case of moving the microscope portion 68 in the horizontal direction (the left direction in FIGS. 5A and 6A), the microscope portion 68 can be moved with a light force.

Figure 6B:
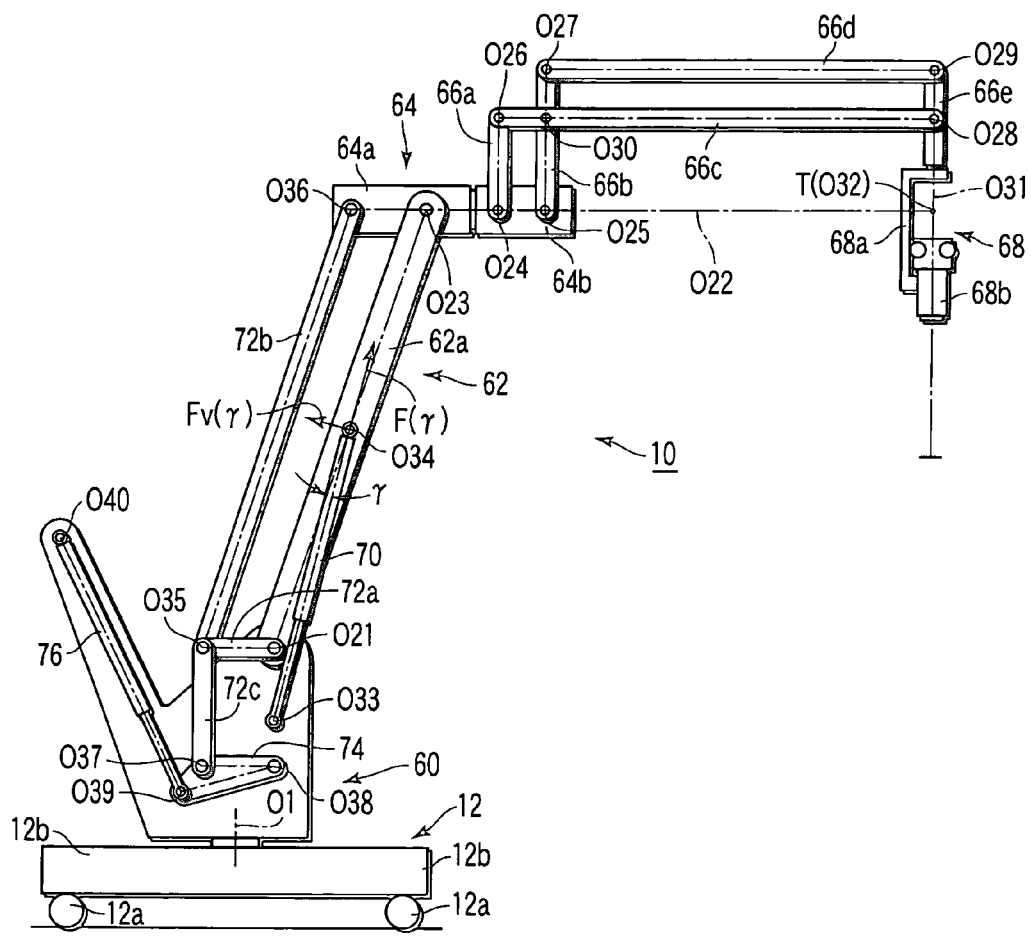
FIG. 6B is a schematic view showing the surgical microscope according to the second embodiment of the present invention in a state where the microscope portion is moved toward a right side in the horizontal direction in the page space.

Next, from the initial state, as shown in FIG. 6B, the microscope portion 68 is moved to the right side with respect to the state depicted in FIG. 5A. The surgical microscope 10 is balanced like the example in which the microscope portion 68 is moved to the left side from the initial state as shown in FIG. 6A.

It is to be noted that, in the initial state where the vertical link 62a is arranged in the vertical direction shown in FIG. 5A, the moment around the 21st rotation axis O21 produced by a weight of the microscope portion 68, or the like becomes zero. Furthermore, the moment around the 21st rotation axis O21 generated by the first gas spring 70 also becomes zero.

Therefore, the microscope portion 68 can be moved to an arbitrary position in the horizontal direction with a light force by the revolving movement of the horizontal movement arm portion 62 around the first horizontal rotation axis (the 21st rotation axis O21).

Figure 7A:
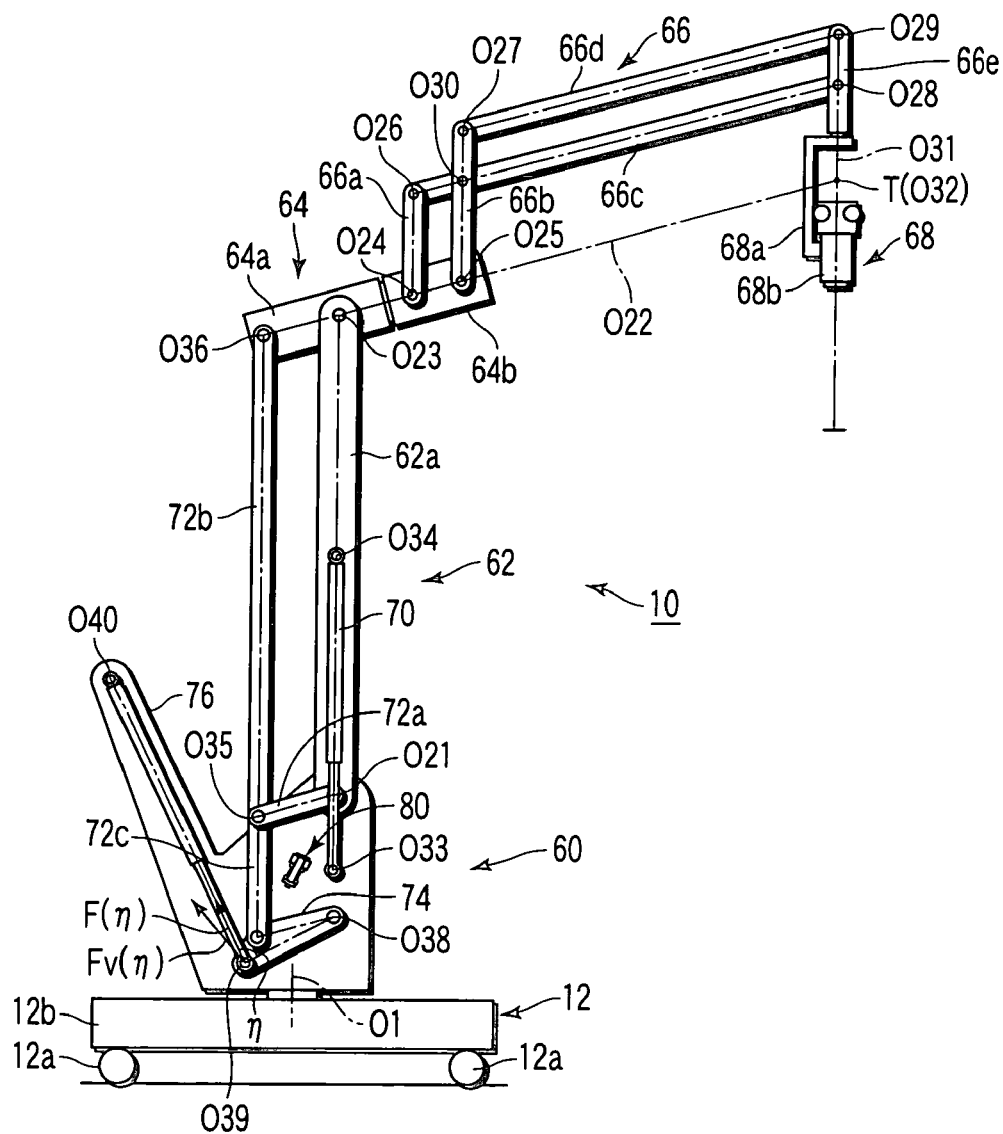
FIG. 7A is a schematic view showing the surgical microscope according to the second embodiment of the present invention in a state where the microscope portion is moved toward an upper side in a vertical direction in the page space.

A description will now be given as to an example in which the microscope portion 68 is moved in the vertical direction (an up-and-down direction in FIGS. 7A, 7B and 8) with reference to FIGS. 7A, 7B and 8. The microscope portion 68 is moved up with respect to the state depicted in FIG. 5A from the initial state as shown in FIG. 7A.

When the microscope portion 68 is moved up, the fifth movable link 66e follows up this movement to be moved up. The third and fourth movable links 66c and 66d each having one end portion pivoted on the fifth movable link 66e are revolved around the 26th and 27th rotation axes O26 and O27 on the other end sides of the third and fourth movable links 66c and 66d. At this time, the first and second movable links 66a and 66b on which the other end portions of the third and fourth movable links 66c and 66d are pivoted are moved up along the vertical direction. It is to be noted that the third and fourth movable links 66c and 66d are configured to maintain a parallel state, and hence a moving distance of the first movable link 66a toward the upper side along the vertical direction is smaller than a moving distance of the second movable link 66b toward the upper side along the vertical direction.

As a result, the arm support portion 64 is revolved around the 23rd rotation axis O23 with respect to the vertical link 62a. Moreover, the second coupling link 72b whose upper end portion is pivoted on the arm support portion 64 is moved down in the vertical direction. As a result, the first coupling link 72a whose one end portion is pivoted at the lower end portion of the second coupling link 72a is revolved around the 21st rotation axis O21 of the other end portion of the first coupling link 72a, and the third coupling link 72c whose upper end portion is pivoted at the lower end portion of the second coupling link 72b is moved down along the vertical direction. The link member 74 whose first apex is pivoted at the lower end portion of the third coupling link 72c is revolved around the 38th rotation axis O38 of the second apex with respect to the base bottom portion 60.

When the link member 74 is revolved around the 38th rotation axis O38, the second gas spring 76 whose one end portion is pivoted at the third apex of the link member 74 is also revolved around the 40th rotation axis O40 of the other end portion of the second gas spring 76 with respect to the base bottom portion 60. As a result, the second gas spring 76 is expanded, and an angle η formed between the central axis of the second gas spring 76 and a straight line perpendicular to the 38th rotation axis O38 and the 39th rotation axis O39 of the link member 74 is changed.

Therefore, a reactive force F(η) which is a function of the angle η is generated in the second gas spring 76 along the central axis direction. A consideration will now be given as the this reactive force F(η) by dividing it into a component in a straight line direction perpendicular to the 38th rotation axis O38 and the 39th rotation axis O39 of the link member 74 and a component force Fv(η) which is a component perpendicular to this straight line direction and the horizontal direction. A magnitude of this component force Fv(η) is determined based on a magnitude of the reactive force F(η) of the second gas spring 76 and the angle η formed between the central axis of the second gas spring 76 and the straight line perpendicular to the 38th rotation axis O38 and the 39th rotation axis O39 of the link member 74.

A moment around the 38th rotation axis O38 generated by the second gas spring 76 is obtained by multiplying a distance between the 38th rotation axis O38 and the 39th rotation axis O39 on which the component force Fv(η) acts by the magnitude of the component force Fv(η). This moment is changed when the component force Fv(η) varies with a change in the angle η.

On the other hand, a moment around the 38th rotation axis O38 is produced in the link member 74 by weights of the microscope portion 68, the vertical movement arm portion 66 and the first to third coupling links 72a, 72b and 72c, or the like. This moment is also a function of the angle η.

Here, the moment around the 38th rotation axis O38 generated by the second gas spring 76 functions to offset the moment around the 38 rotation axis O38 produced by a weight of the microscope portion 68, or the like. Additionally, the spring strength of the second gas spring 76 and the arrangement of the first to third coupling links 72a, 72b and 72c, the link member 74 and the second gas spring 76 are selected in such a manner that the two moments are balanced in accordance with the substantially whole change in the angle η.

Therefore, even if the microscope portion 68 is moved up in the vertical direction (the upper direction in FIGS. 5A and 7A) to be revolved around the 23rd rotation axis O23, the balance of the surgical microscope 10 is redressed by the rotation moment generated by the second gas spring 76. Therefore, in case of moving up the microscope portion 68 in the vertical direction (the upper direction in FIGS. 5A and 7A), the microscope portion 68 can be moved with a light force.

Figure 7B:
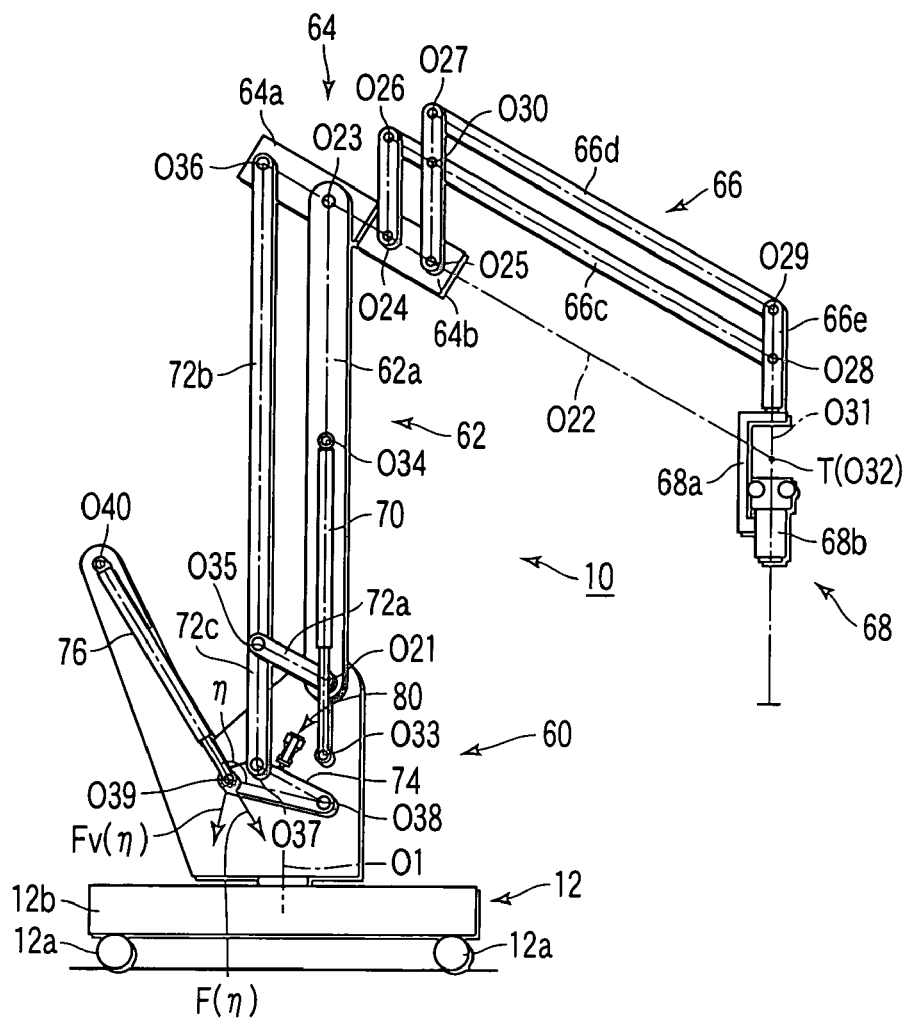
FIG. 7B is a schematic view showing the surgical microscope according to the second embodiment of the present invention in a state where the microscope portion is moved toward a lower side in the vertical direction in the page space.

Next, from the initial state, as shown in FIG. 7B, the microscope portion 68 is moved down with respect to the state depicted in FIG. 5A. The balance of the surgical microscope 10 is redressed like the example of moving up the microscope portion 68 from the initial state as shown in FIG. 7A.

For example, when the microscope portion 68 is continuously moved from the state depicted in FIG. 7A to the state shown in FIG. 7B, the moment around the 38th rotation axis O38 generated by a weight of the microscope portion 68, or the like is offset by the moment around the 38th rotation axis O38 produced by the second gas spring 76. That is, the angle η formed between the central axis of the second gas spring 76 and the straight line perpendicular to the 38th rotation axis O38 and the 39th rotation axis O39 of the link member is changed, the component force Fv(η) of the reactive force F(η) of the second gas spring 76 is changed, and the moment generated by the second gas spring 76 is changed to offset the rotation moment around the 38th rotation axis O38 produced by weights of the microscope portion 68, the vertical movement arm portion 66 and the first to third coupling links 72a, 72b and 72c, or the like.

Meanwhile, as shown in FIG. 7B, in case of setting a revolving range of the vertical movement arm portion 66 to be relatively large, the angle η formed between the central axis of the second gas spring 76 and the straight line perpendicular to the 38th rotation axis O38 and the 39th rotation axis O39 of the link member 74 becomes small in the vicinity of a lower end portion of the revolving range, and the component force Fv(η) is reduced. In this case, the component force Fv(η) of the reactive force F(η) of the second gas spring 76 becomes insufficient, and it is difficult to offset the moment around the 38th rotation axis O38 generated by weights of the microscope portion 68, the vertical movement arm portion 66 and the first to third coupling links 72a, 72b and 72c, or the like. In order to compensate such insufficiency of the moment due to the second elastic force generation mechanism as the first balance mechanism, the reactive force generated by the compression spring 86 of the auxiliary balance mechanism 80 is utilized.

Figure 8:
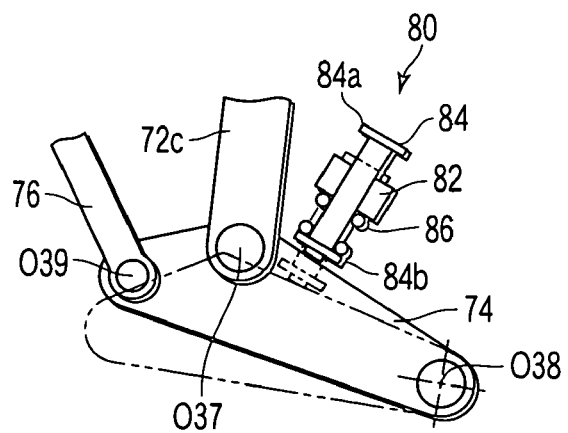
FIG. 8 is a schematic view showing the auxiliary balance mechanism and a link member of the surgical microscope according to the second embodiment of the present invention in a state where the microscope portion is moved toward the lower side in the vertical direction whereby the link member is brought into contact with the auxiliary balance mechanism.

As shown in FIGS. 7B and 8, when the microscope portion 68 is moved down to revolve the link member 74 upward around the 38th rotation axis O38, one upper surface of the link member 74 comes into contact with the second flange portion 84b of the shaft portion 84 of the auxiliary balance mechanism 80 as indicated by a chain double-dashed line in FIG. 8. When the microscope portion 68 is further moved down to revolve the link member 74, the link member 74 pushes up the second flange portion 84b of the shaft portion 84 along the axial direction of the shaft portion 84 (an obliquely upper right direction in FIG. 8) and is revolved while compressing the compression spring 86. Therefore, a reactive force of the compression spring 86 acts on the link member 74 through the second flange portion 84b, thereby correcting insufficiency of a moment produced by the second gas spring 76.

Accordingly, even if the microscope portion 68 is moved down in the vertical direction (the lower direction in FIGS. 5A and 7B) to be revolved around the 23rd rotation axis O23, the balance of the surgical microscope 10 is redressed by a rotation moment generated by the second gas spring 76 and the compression spring 86. Therefore, in case of moving down the microscope portion 68 in the vertical direction (the lower direction in FIGS. 5A and 7B), the microscope portion 68 can be moved with a light force.

Thus, the microscope portion 68 can be moved to an arbitrary position in the vertical direction with a light force by a revolving movement of the vertical movement arm portion 66 around the second horizontal rotation axis (the 23rd rotation axis O23).

The observation direction of the binocular tube 68b can be three-dimensionally arbitrarily moved and inclined by the horizontal movement of the microscope portion 68 by the horizontal movement arm portion 62, the vertical movement of the microscope portion 68 by the vertical movement arm portion 66 and the revolving movement of the binocular tube 68b of the microscope portion 68 around the 22nd, 31st and 32nd rotation axes O22, O31 and O32. An operator arbitrarily moves and inclines the binocular tube 68b to observe a desired part of a patient.

Therefore, the surgical microscope 10 having the above-described structure demonstrates the following effects in addition to those of the first embodiment. The vertical movement arm portion 66, the arm support portion 64 and the first arm 68a constitute an inclination mechanism which inclines the binocular tube 68b of the microscope portion 68. Therefore, as there is no need of arranging a large inclination mechanism in the vicinity of the microscope portion 68, a larger working space for an observer can be assured, the structure of the surgical microscope 10 can be simplified and the surgical microscope 10 can be reduced in size and weight.

Furthermore, the second coupling link 72b which couples the vertical movement arm portion 66 with the link member 74 also serves as a parallelogram link mechanism of the horizontal movement arm portion 62. Moreover, the accommodating portion of the second gas spring 76 also functions as a moving handle which moves the surgical microscope 10 on a floor or the like in a state where the stoppers of the casters 12a are released. Additionally, the auxiliary balance mechanism 80 as the second balance mechanism is built in the base bottom portion 60. Therefore, a larger working space for an observer can be assured, the structure of the surgical microscope 10 can be simplified, and the surgical microscope 10 can be reduced in size and weight.

Figure 9A:
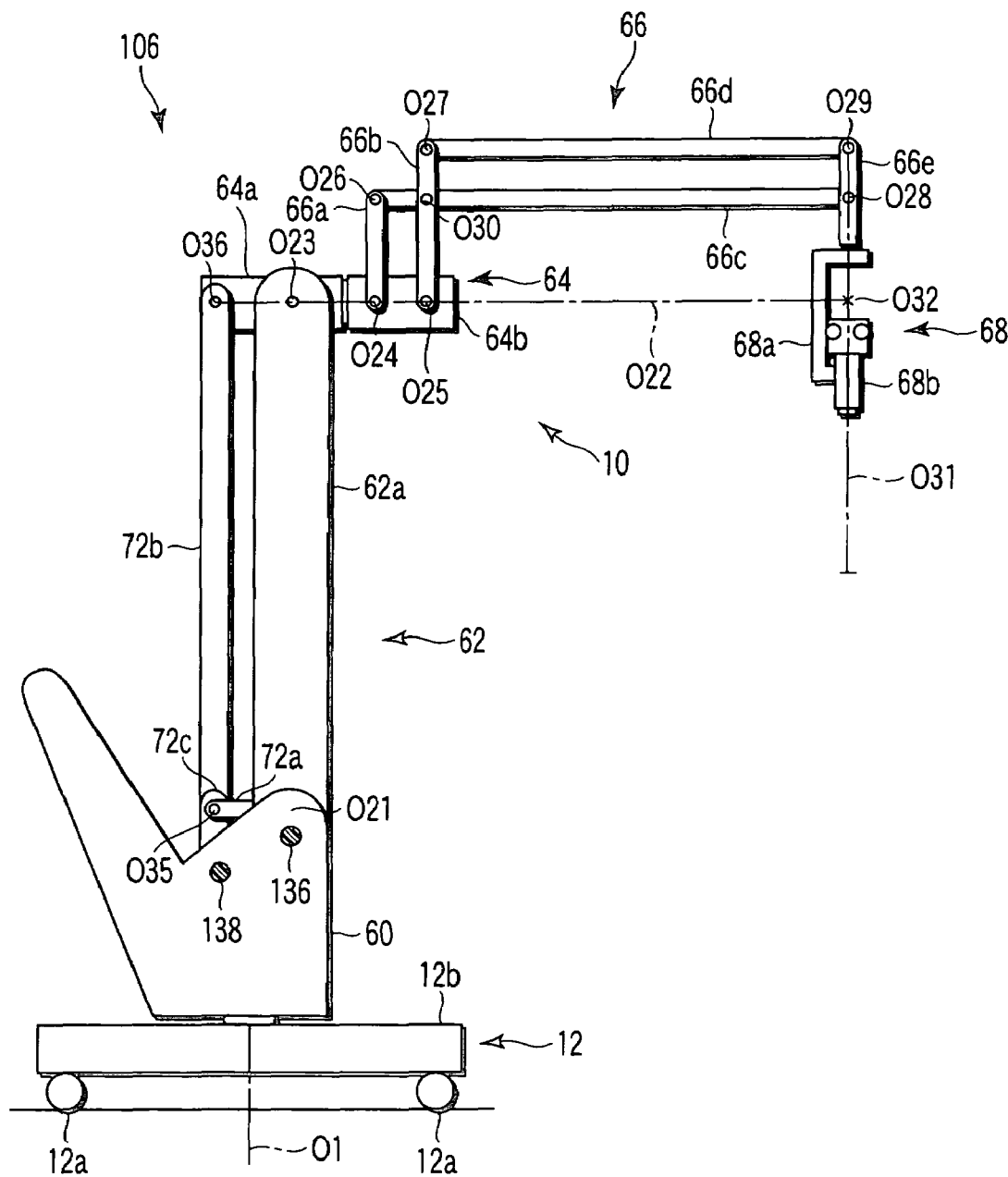
FIG. 9A is a side view showing a surgical microscope according to a third embodiment of the present invention.
Figure 9B:
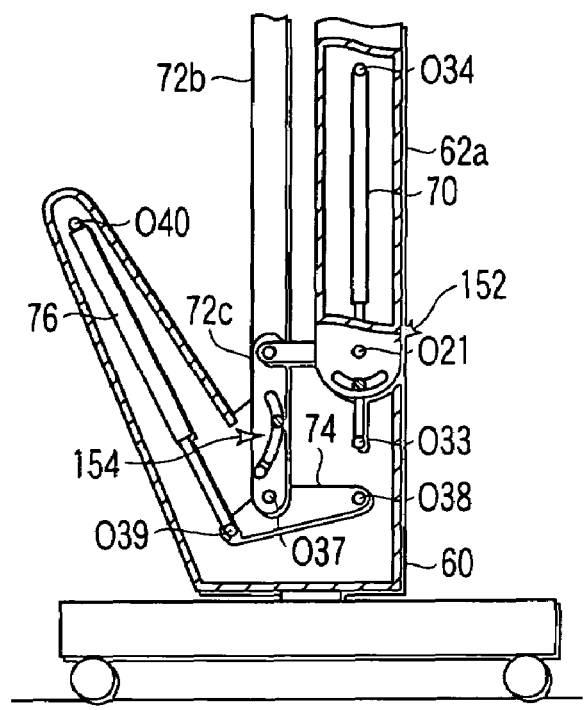
FIG. 9B is a cross-sectional view showing a lower portion of the surgical microscope according to the third embodiment of the present invention.

A third embodiment according to the present invention will now be described with reference to FIGS. 9A to 19. As shown in FIGS. 9A and 9B, in a surgical microscope 10 according to this embodiment, first and second restriction mechanisms 152 and 154 are added to the surgical microscope 10 according to the second embodiment. These first and second restriction mechanisms 152 and 154 restrict an in-use movable range in which a movable portion of the surgical microscope 10 is moved during use of a microscope portion 68 and an in-accommodation movable range which is different from the in-use movable range and in which the movable portion is moved when the microscope portion 68 is accommodated.

It is to be noted that structures other than the first and second restriction mechanisms 152 and 154 are the same as those in the second embodiment, thereby eliminating their explanation. Further, in FIGS. 9A to 19, the illustration of an auxiliary balance mechanism 80 is eliminated for the convenience's sake. A part other than a binocular tube 68b of the surgical microscope 10 will be referred to as a holding portion 106 which holds the binocular tube 68 hereinafter.

As shown in FIGS. 9A and 9B, the first restriction mechanism 152 is arranged between a vertical link 62a and a base bottom portion 60. This first restriction mechanism 152 restricts a movable range of the vertical link 62a with respect to the base bottom portion 60 to restrict a revolving range of a horizontal movement arm portion 62 around a 21st rotation axis O21, thereby limiting a moving range of the binocular tube 68b. A first knob portion 136 of the first restriction mechanism 152 is arranged on an outer side of the base bottom portion 60.

Furthermore, the second restriction mechanism 154 is arranged between a third coupling link 72c and the base bottom portion 60. This second restriction mechanism 154 restricts a movable range of the third coupling link 72c with respect to the base bottom portion 60 to restrict a revolving range of a vertical movement arm portion 66 around a 23rd rotation axis O23, thereby limiting a moving range of the binocular tube 68b. A second knob portion 138 of the second restriction mechanism 154 is arranged on an outer side of the base bottom portion 60.

Figure 10A:
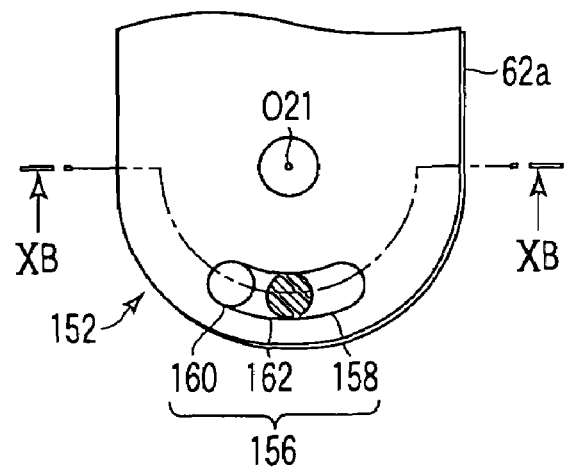
FIG. 10A is a cross-sectional view showing a first restriction mechanism of the surgical microscope according to the third embodiment of the present invention.

As shown in FIG. 10A, the first restriction mechanism 152 has a guide groove 156 formed at a lower end portion of the vertical link 62a. This guide groove 156 is extended in a circumferential direction of the 21st rotation axis O21. An elongated groove-like moving groove portion 158 is arranged on this guide groove 156 side closer to the binocular tube 68b (see FIG. 9A), a substantially circular fixing groove portion 160 is arranged on an opposite side, and a gourd-like curved restriction groove portion 162 is arranged between the moving groove portion 158 and the fixing groove portion 160. A width of the moving groove portion 158 and a diameter of the fixing groove portion 160 are slightly larger than a diameter of a large-diameter portion 168 of a shaft portion 166 in the first knob portion 136, and a minimum width of the restriction groove portion 162 is slightly smaller than the diameter of the large-diameter portion 168.

As shown in FIG. 10B, a pedestal 164 is arranged on an outer wall of the base bottom portion 60. The first knob portion 136 is attached on this pedestal 164. This first knob portion 136 can rotate around the central axis of the pedestal 164 vertical to the outer wall of the base bottom portion 60 at the center, and is protrusible/retractable in the axial direction. The shaft portion 166 is arranged at the central part of the first knob portion 136 in the central axis direction. This shaft portion 166 is fixed in the first knob portion 136 by a screw. The shaft portion 166 is inserted into a through hole formed in the pedestal 164 and the base bottom portion 60.

The large-diameter portion 168 is arranged at a distal part of the shaft portion 166. An elastic member, e.g., a spring 170 is compressed and arranged between this large-diameter portion 168 and a flange portion of the pedestal 164. This spring 170 inwardly presses the first knob portion 136 along the axial direction with respect to the pedestal 164. A stopper pin 172 is arranged in the first knob portion 136. The shaft portion 166 protrudes toward the inside of the base bottom portion 60 through the through hole of the pedestal 164 and the base bottom portion 60, and the large-diameter portion 168 is inserted in the moving groove portion 158.

Here, a depth of the moving groove portion 158 is substantially equal to a depth of the restriction groove portion 162, and a depth of the fixing groove portion 160 is larger than depths of these groove portions.

As shown in FIG. 10C, a lock hole 174 is formed in the pedestal 164. This lock hole 174 is formed of a vertical groove portion extending in the axial direction of the shaft portion 166 and a lateral groove portion 166 extending in a circumferential direction of the shaft portion from a base end part of this vertical groove portion. Widths of these vertical groove portion and lateral groove portion are slightly larger than a diameter of the stopper pin 172 (see FIG. 10B).

As shown in FIG. 10D, the second restriction mechanism 154 has substantially the same structure as the first restriction mechanism 152 depicted in FIGS. 10A to 10C. That is, as shown in FIG. 10D, the second restriction mechanism 154 is formed at a lower portion of a third coupling link 72c and has a guide groove 176 gently curved and extending in a longitudinal direction of the third coupling link 72c. An elongated groove-like moving groove portion 178 is arranged on an upper side of this guide groove 176, a substantially circular fixing groove portion 180 is arranged at a lower portion, and a restriction groove portion 182 is arranged between the moving groove portion 178 and the fixing groove portion 180. A width of the moving groove portion 178 and a diameter of the fixing groove portion 180 are slightly larger than a diameter of a large-diameter portion 190 of a shaft portion 188 in the second knob portion 138 depicted in FIG. 10E. Moreover, as shown in FIG. 10D, the restriction groove portion 182 does not have a constricted shape, and has a width which is substantially equal to the width of the moving groove portion 178 and the diameter of the fixing groove portion 180.

Figure 10E:
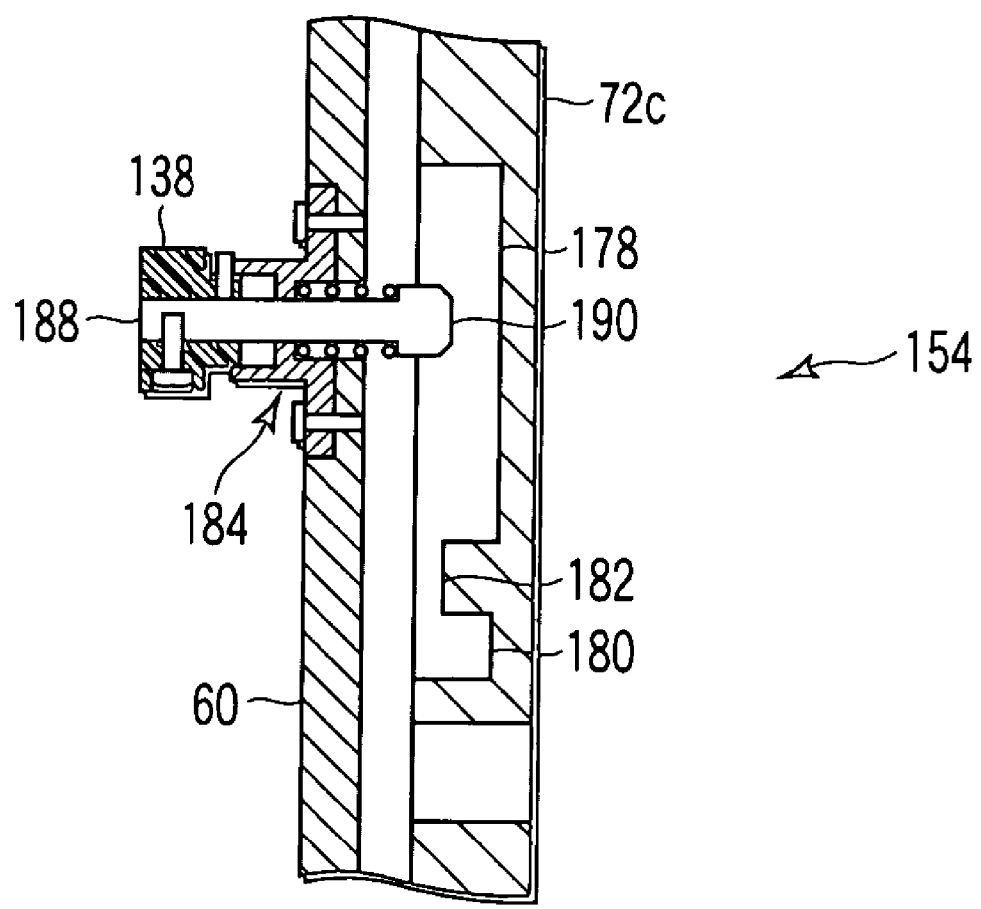
FIG. 10E is a cross-sectional view showing the second restriction mechanism of the surgical microscope according to the third embodiment of the present invention taken along a line XE-XE in FIG. 10D.

As shown in FIG. 10E, a depth of the moving groove portion 178 is substantially equal to a depth of the fixing groove portion 180, and a depth of the restriction groove portion 182 is smaller than depths of these groove portions. Additionally, the second restriction mechanism 154, the second knob portion 138 and a pedestal 184 which are the same as those in the first restriction mechanism 152 depicted in FIGS. 10A to 10C. Further, the second knob portion 138 has the shaft portion 188, and the shaft portion 188 has the large-diameter portion 190.

Figure 11A:
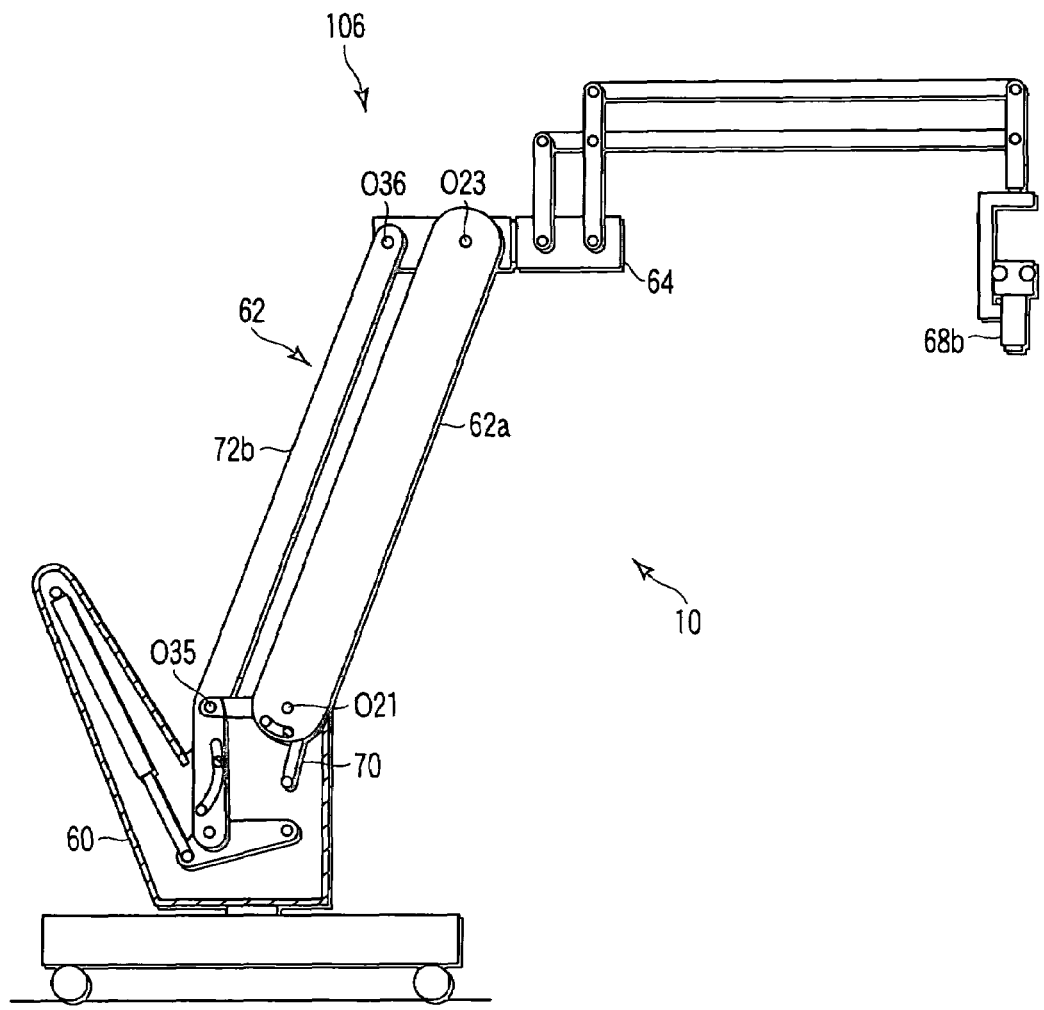
FIG. 11A is a cross-sectional view showing the surgical microscope according to the third embodiment of the present invention in a state where a microscope body is set at an in-use forward movement limit.
Figure 11B:
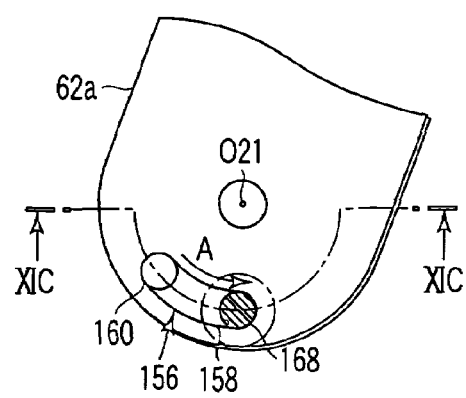
FIG. 11B is a cross-sectional view showing the first restriction mechanism of the surgical microscope according to the third embodiment of the present invention in a state where the microscope body is set at the in-use forward movement limit.
Figure 11C:
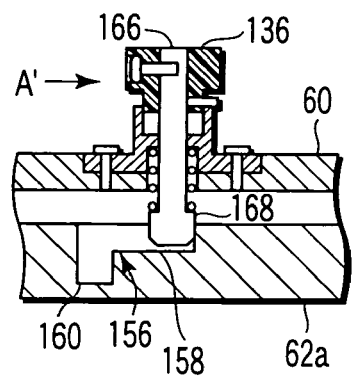
FIG. 11C is a cross-sectional view showing the first restriction mechanism of the surgical microscope according to the third embodiment of the present invention in a state where the microscope body is set at the in-use forward movement limit taken along a line XIC-XIC in FIG. 11B.

A function of the surgical microscope 10 having the above-mentioned structure according to this embodiment will now be described. As shown in FIG. 11A, when the binocular tube 68 is moved forward, the binocular tube 68b is pulled toward the front side. During the forward movement of the binocular tube 68b, as indicated by arrows A and A' in FIGS. 11B and 11C, the large-diameter portion 168 of the shaft portion 166 in the first knob portion 136 is relatively moved in a direction opposite to the fixing groove portion 160 in the moving groove portion 158 of the guide groove 156 of the vertical link 62a. Furthermore, when the large-diameter portion 168 comes into contact with an end wall of the moving groove portion 158, a revolving movement of the vertical link 62a around the 21st rotation axis O21 is restricted. In this manner, the forward movement of the binocular tube 68b is restricted. This state is an in-use forward movement limit during use of the binocular tube 68b.

Figure 12A:
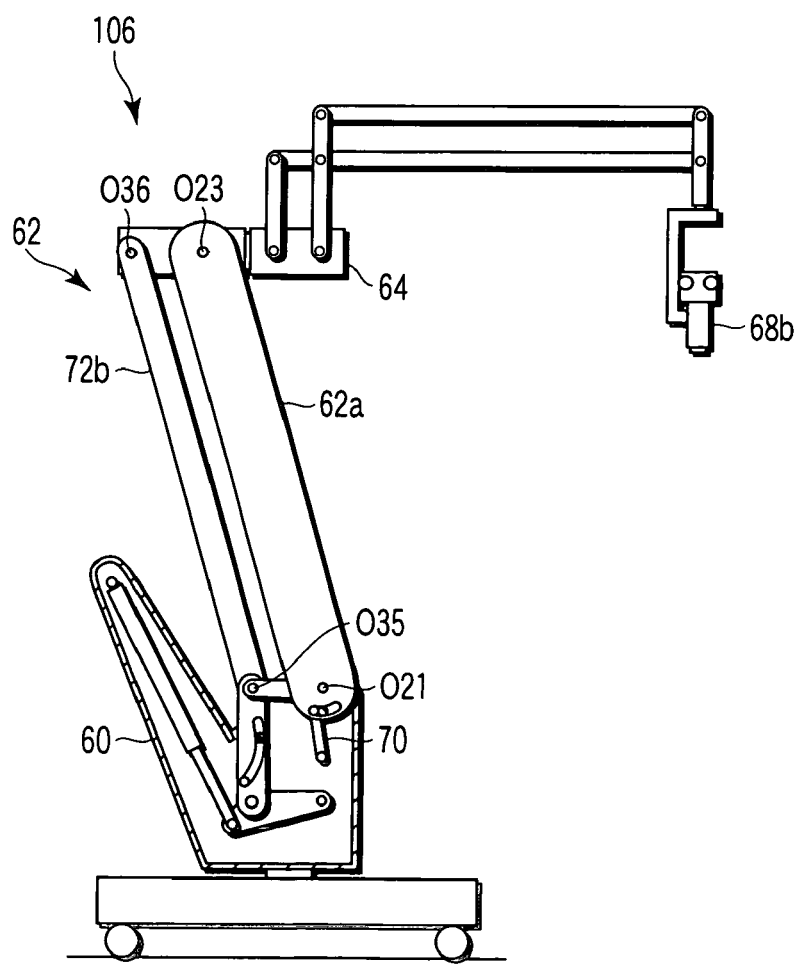
FIG. 12A is a cross-sectional view showing the surgical microscope according to the third embodiment of the present invention in a state where the microscope body is set at an in-use backward movement limit.
Figure 12B:
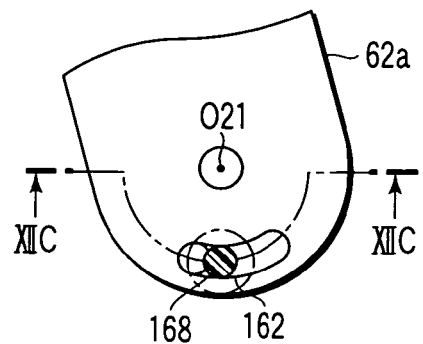
FIG. 12B is a cross-sectional view showing the first restriction mechanism of the surgical microscope according to the third embodiment of the present invention in a state where the microscope body is set at the in-use backward movement limit.
Figure 12C:
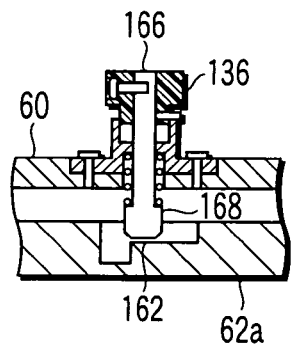
FIG. 12C is a cross-sectional view showing the first restriction mechanism of the surgical microscope according to the third embodiment of the present invention in a state where the microscope body is set at the in-use backward movement limit taken along a line XIIC-XIIC in FIG. 12B.

As shown in FIG. 12A, in case of moving the binocular tube 68b backward, a function which is opposite to that of the forward movement of the binocular tube 68b occurs. As depicted in FIGS. 12B and 12C, when the large-diameter portion 168 comes into contact with the constricted shape of the restriction groove 162, a revolving movement of the vertical link 62a around the 21st rotation axis O21 is restricted. This state is an in-use backward movement limit during use of the binocular tube 68b.

Here, an in-use movable range of the vertical link 62a with respect to the base bottom portion 60 is defined by a state in which the large-diameter portion 168 is in contact with the end wall of the moving groove portion 158 and a state in which the large-diameter portion 168 is in contact with the constricted shape of the restriction groove portion 162. Furthermore, the in-use forward movement limit and the in-use backward movement limit of the binocular tube 68b define an in-use forward/backward movement range of the binocular tube 68b.

Figure 15A:
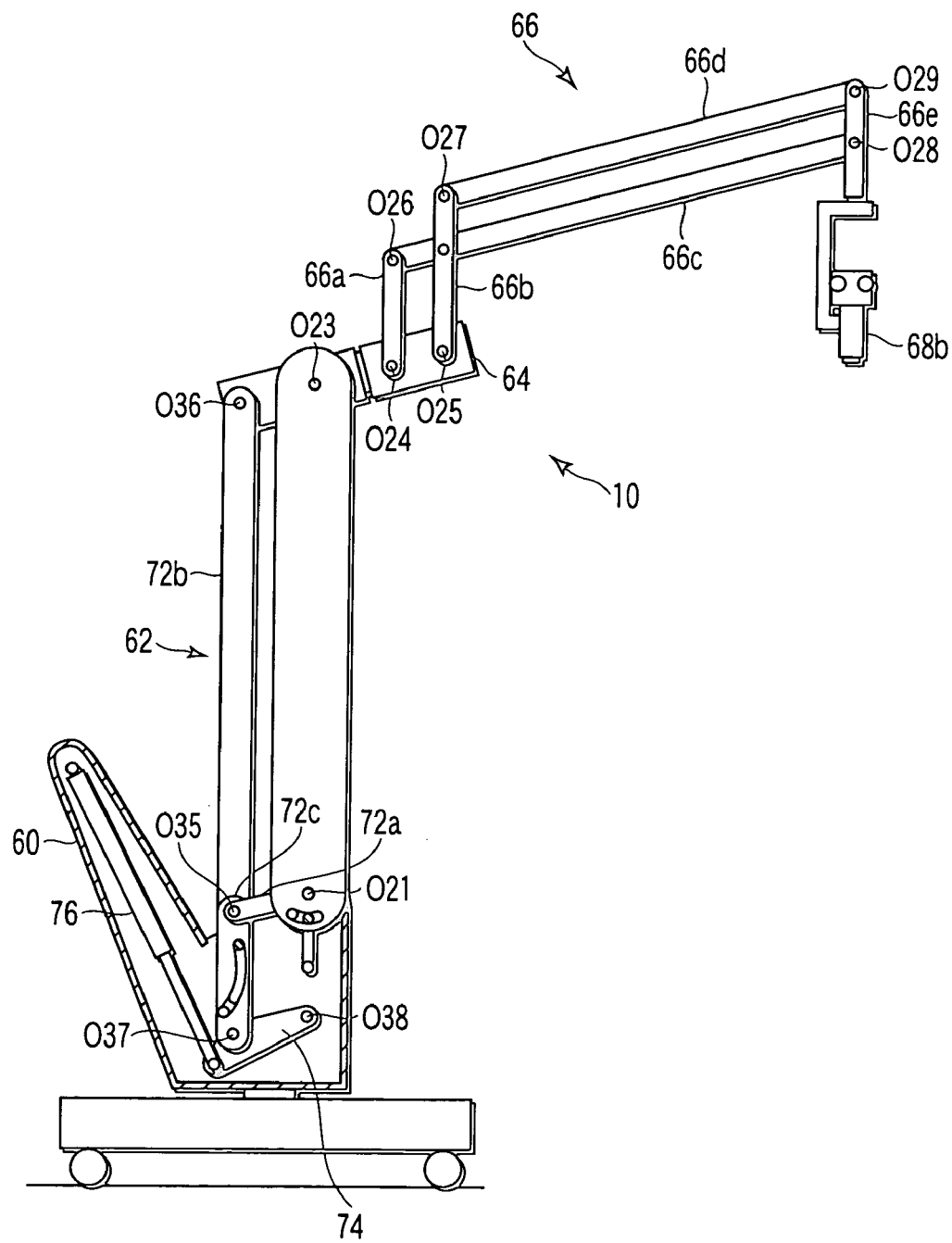
FIG. 15A is a cross-sectional view showing the surgical microscope according to the third embodiment of the present invention in a state where the microscope body is set at an in-use upward movement limit.
Figure 15B:
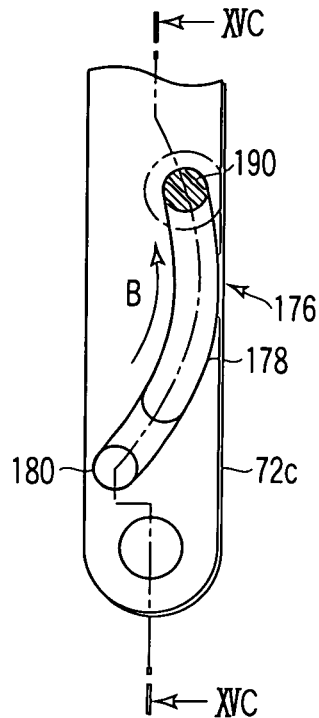
FIG. 15B is a cross-sectional view showing a second restriction mechanism of the surgical microscope according to the third embodiment of the present invention in a state where the microscope body is set at the in-use upward movement limit.
Figure 15C:
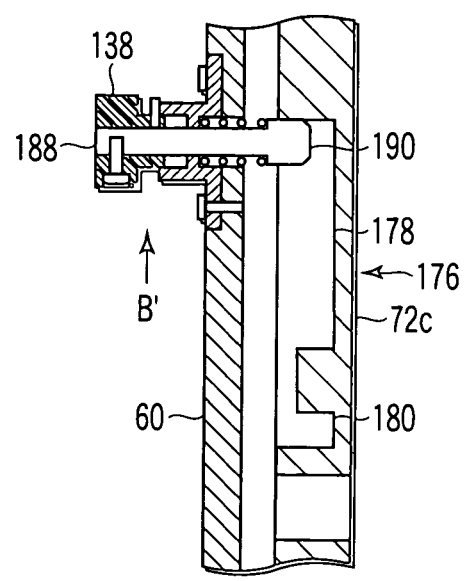
FIG. 15C is a cross-sectional view showing the second restriction mechanism of the surgical microscope according to the third embodiment of the present invention in a state where the microscope body is set at the in-use upward movement limit taken along a line XVC-XVC in FIG. 15B.

As shown in FIG. 15A, in case of moving up the binocular tube 68b, the binocular tube 68b is pushed toward a right above position. During the upward movement of the binocular tube 68b, as indicated by arrows B and B' in FIGS. 15B and 15C, the large-diameter portion 190 of the shaft portion 188 of the second knob portion 138 is relatively moved in a direction opposite to the fixed grove portion 180 in the moving groove portion 178 of the guide groove 176 of the third coupling link 72c. When the large-diameter portion 190 comes into contact with an upper end wall of the moving groove portion 178, the downward movements of the second and third coupling links 72b and 72c are restricted, thereby limiting a revolving movement of an arm support portion 64. In this manner, the upward movement of the binocular tube 68b is restricted. This state is an in-use upward movement limit during use of the binocular tube 68b.

Figure 16B:
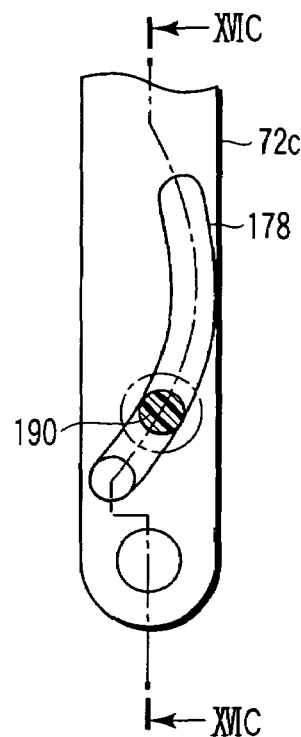
FIG. 16B is a cross-sectional view showing the second restriction mechanism of the surgical microscope according to the third embodiment of the present invention in a state where the microscope body is set at the in-use downward movement limit.
Figure 16C:
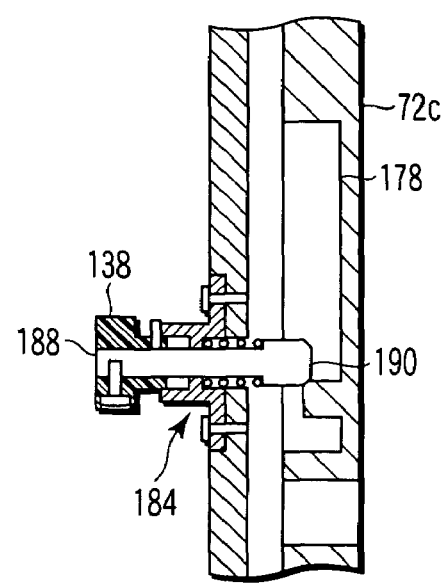
FIG. 16C is a cross-sectional view showing the second restriction mechanism of the surgical microscope according to the third embodiment of the present invention in a state where the microscope body is set at the in-use downward movement limit taken along a line XVIC-XVIC in FIG. 16B.

As shown in FIG. 16A, in case of moving down the binocular tube 68b, a function which is opposite to that of the upward movement of the binocular tube 68b occurs. As depicted in FIGS. 16B and 16C, when the large-diameter portion 190 comes into contact with a lower end wall of the moving groove portion 178, upward movements of the second and third coupling links 72b and 72c are restricted, thereby limiting a revolving movement of the arm support portion 64. This state is an in-use downward movement limit during use of the binocular tube 68b.

Here, an in-use movable range of the third coupling link 72c with respect to the base bottom portion 60 is defined by a state in which the large-diameter portion 190 is in contact with the upper end wall of the moving groove portion 178 and a state in which the large-diameter portion 190 is in contact with the lower end wall of the same. Moreover, the in-use upward movement limit and the in-use downward movement limit of the binocular tube 68b define an in-use upward/downward movement range of the binocular tube 68b.

Although the above has separately described the movement of the binocular tube 68 in the front-and-back direction and the movement of the same in the up-and-down direction in order to simplify the explanation, these movements can be combined. Combining the in-use upward/downward movement range of the binocular tube 68b with the in-use frontward/backward movement range of the same define the in-use movement range of the binocular tube 68b.

After use of the surgical microscope 10, the following accommodating operation is carried out when accommodating the surgical microscope 10. An accommodating operation based on a backward movement of a microscope body and an accommodating operation based on a downward movement of the microscope body will be separately described below in order to simplify the explanation.

Figure 13A:
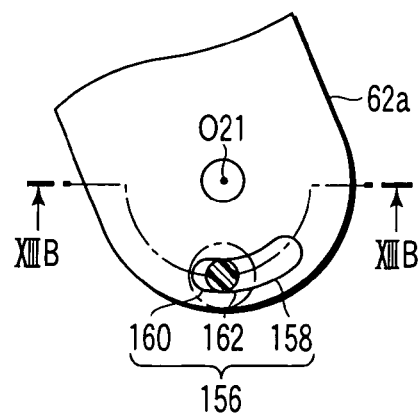
FIG. 13A is a cross-sectional view showing the first restriction mechanism of the surgical microscope according to the third embodiment of the present invention in a state where the microscope body is set between the in-use backward movement limit and an in-accommodation backward movement limit.
Figure 13B:
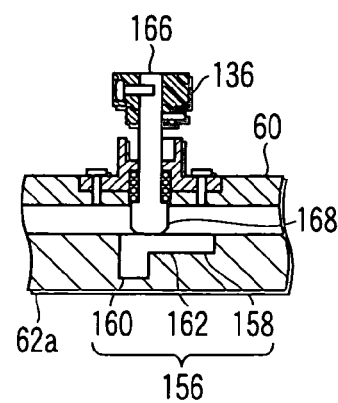
FIG. 13B is a cross-sectional view showing the first restriction mechanism of the surgical microscope according to the third embodiment of the present invention in a state where the microscope body is set between the in-use backward movement limit and the in-accommodation backward movement limit taken along a line XIIIB-XIIIB in FIG. 13A.

In the accommodating operation based on the backward movement of the binocular tube 68b, the binocular tube 68b is set to such an in-use backward movement limit as shown in FIGS. 12A, 12B and 12C. Additionally, the first knob portion 136 is outwardly moved along the axial direction to pull out the large-diameter portion 168 of the shaft portion 166 from the restriction groove portion 162. In this state, the binocular tube 68b is moved rearward to revolve the upper end part of the vertical link 62a backward around the 21st rotation axis O21, and the large-diameter portion 168 is relatively moved along the guide groove 156 from the moving groove portion 158 to the fixing groove portion 160 to cut across the restriction groove portion 162 as shown in FIGS. 13A and 13B.

Figure 14A:
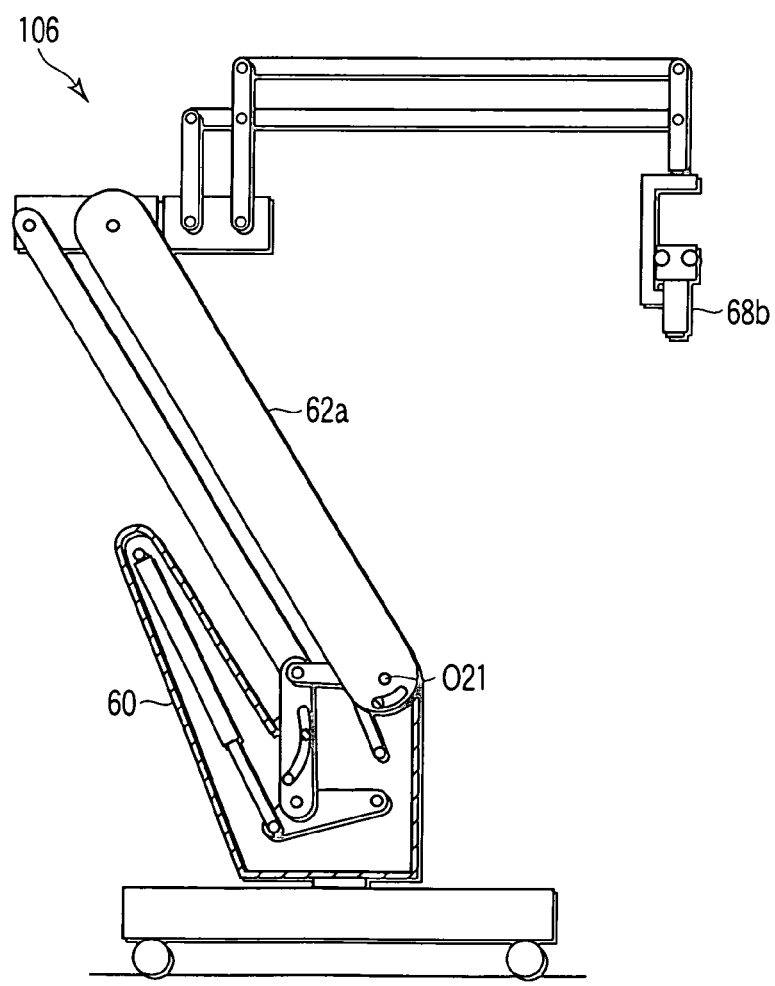
FIG. 14A is a cross-sectional view showing the surgical microscope according to the third embodiment of the present invention in a state where the microscope body is set at the in-accommodation backward movement limit.
Figure 14B:
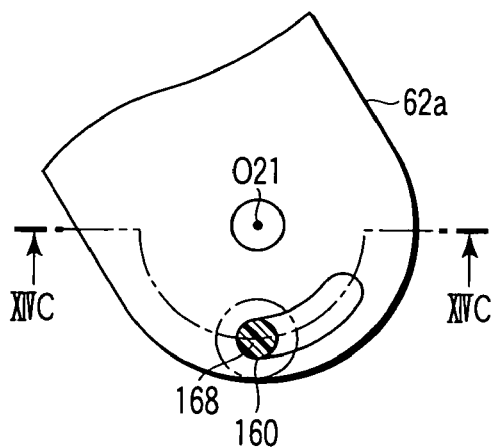
FIG. 14B is a cross-sectional view showing the first restriction mechanism of the surgical microscope according to the third embodiment of the present invention in a state where the microscope body is set at the in-accommodation backward movement limit.
Figure 14C:
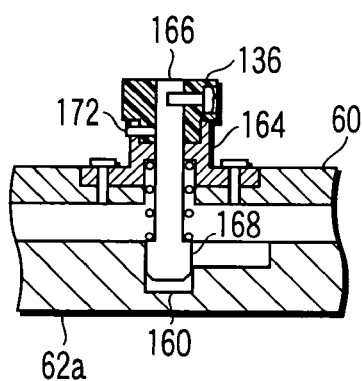
FIG. 14C is a cross-sectional view showing the first restriction mechanism of the surgical microscope according to the third embodiment of the present invention in a state where the microscope body is set at the in-accommodation backward movement limit taken along a line XIVC-XIVC in FIG. 14B.
Figure 14D:
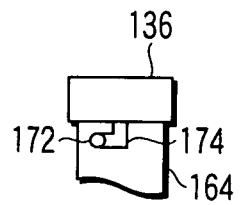
FIG. 14D is a side view showing a first knob portion and a pedestal of the first restriction mechanism of the surgical microscope according to the third embodiment of the present invention in a state where the microscope body is set at the in-accommodation backward movement limit.

Further, as shown in FIG. 14A, the binocular tube 68b is moved rearward to revolve the upper end part of the vertical link 62a backward around the 21st rotation axis O21, and the large-diameter portion 168 is aligned in the fixing groove portion 160 as depicted in FIG. 14B. Then, the first knob portion 136 is rotated with respect to the pedestal 164 to align the stopper pin 172 in the vertical groove of the lock hole 174, and the first knob portion 136 is inwardly pressed in the pedestal 164 along the axial direction so that the stopper pin 172 is inwardly slid in the vertical groove along the axial direction. At this time, as shown in FIG. 14C, the large-diameter portion 168 is fitted into the fixing groove portion 160. Further, the first knob portion 136 is rotated with respect to the pedestal 164 so that the stopper pin 172 is slid in the lateral groove along the circumferential direction, and the first knob portion 136 is locked with respect to the pedestal 136 as shown in FIG. 14D. In this manner, the base bottom portion 60 and the vertical link 62a are locked. This state is an in-accommodation backward movement limit when the binocular tube 68b is accommodated.

Here, an in-accommodation movable range of the vertical link 62a with respect to the base bottom portion 60 is defined by a state in which the large-diameter portion 168 is in contact with the constricted shape of the restriction groove portion 162 and a state in which the large-diameter portion 168 is fitted in the fixing groove portion 160. Furthermore, the in-use backward movement limit and the in-accommodation movement limit of the binocular tube 68b define an in-accommodation frontward/backward movement range of the binocular tube 68b.

Figure 17A:
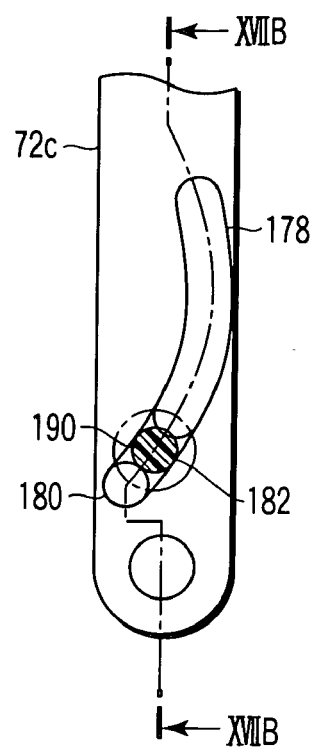
FIG. 17A is a cross-sectional view showing the second restriction mechanism of the surgical microscope according to the third embodiment of the present invention in a state where the microscope body is set between the in-use downward movement limit and an in-accommodation downward movement limit.
Figure 17B:
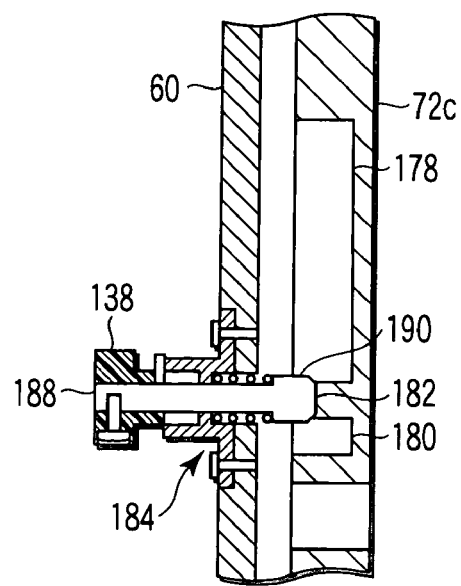
FIG. 17B is a cross-sectional view showing the second restriction mechanism of the surgical microscope according to the third embodiment of the present invention in a state where the microscope body is set between the in-use downward movement limit and the in-accommodation downward movement limit taken along a line XVIIB-XVIIB in FIG. 17A.

In the accommodating operation based on the downward movement of the binocular tube 68b, the holding portion 106 is set to such an in-use downward movement limit as shown in FIGS. 16A, 16B and 16C. Moreover, the second knob portion 138 is outwardly moved with respect to the pedestal 184 along the axial direction, and the large-diameter portion 190 of the shaft portion 188 is outwardly pulled out along the axial direction in such a manner that the large-diameter portion 190 is not brought into contact with the end wall of the moving groove portion 178. In this state, the binocular tube 68b is moved down to move up the second and third coupling links 72b and 72c, and the large-diameter portion 190 is relatively moved from the moving groove portion 178 to the fixing groove portion 180 through the restriction groove portion 182 as shown in FIGS. 17A and 17B.

Figure 18A:
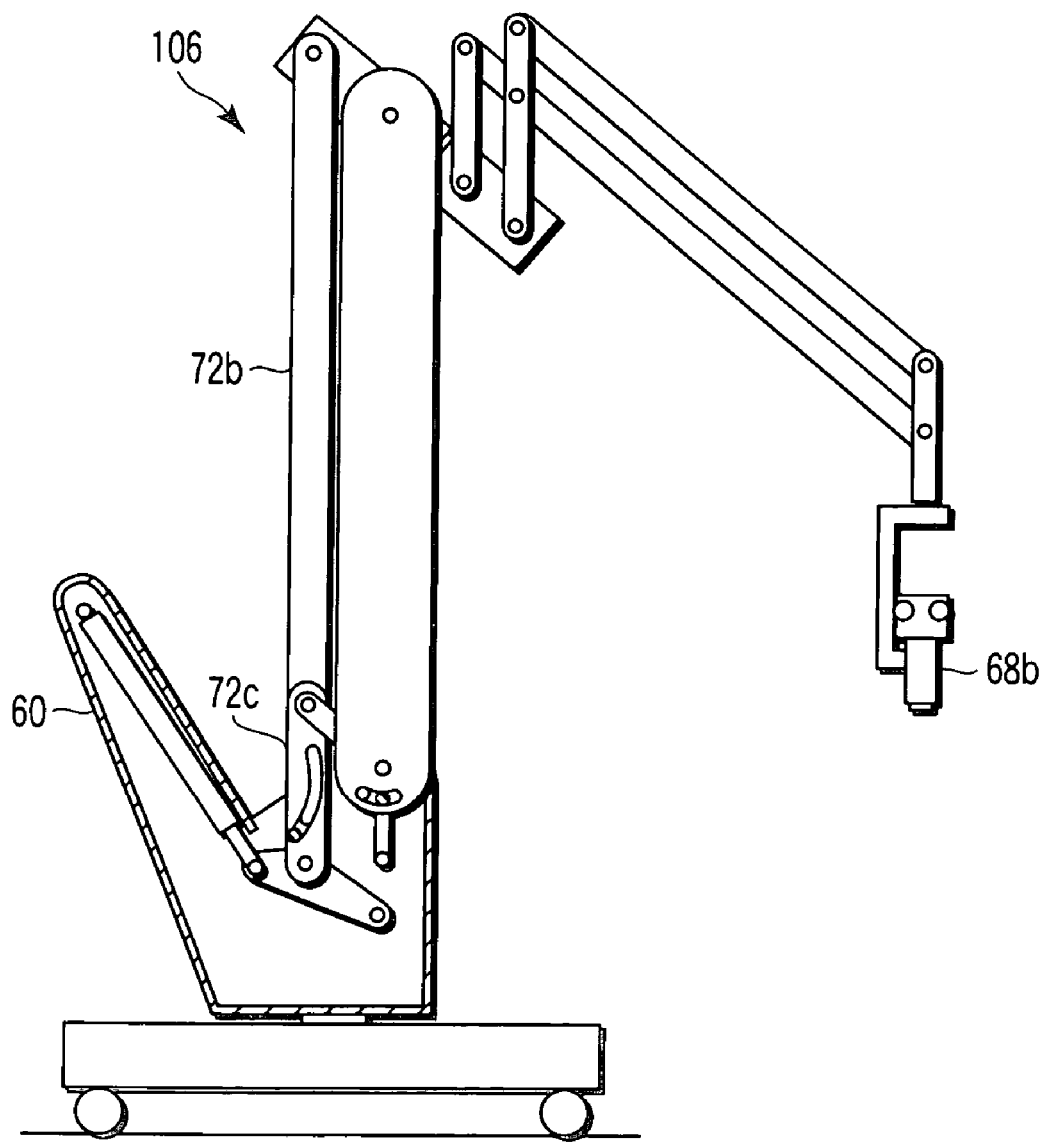
FIG. 18A is a cross-sectional view showing the surgical microscope according to the third embodiment of the present invention in a state where the microscope body is set at the in-accommodation downward movement limit.
Figure 18B:
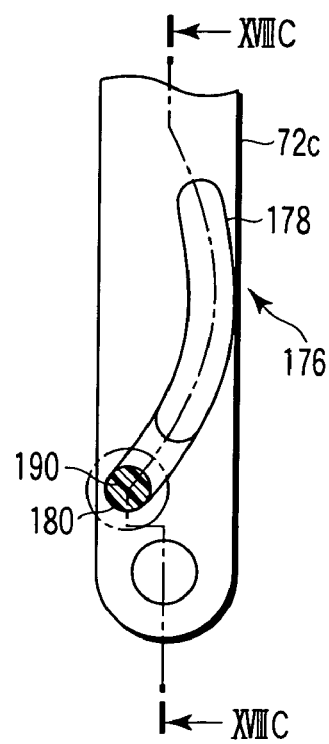
FIG. 18B is a cross-sectional view showing the second restriction mechanism of the surgical microscope according to the third embodiment of the present invention in a state where the microscope body is set at the in-accommodation downward movement limit.
Figure 18C:
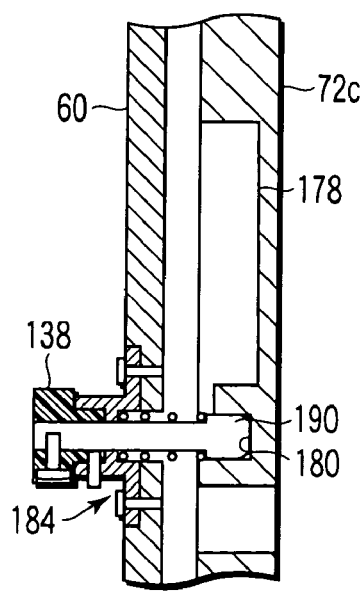
FIG. 18C is a cross-sectional view showing the second restriction mechanism of the surgical microscope according to the third embodiment of the present invention in a state where the microscope body is set at the in-accommodation downward movement limit taken along a line XVIIIC-XVIIIC in FIG. 18B.

Additionally, the binocular tube 68b is moved down to move up the second and third coupling links 72b and 72c as shown in FIG. 18A, and the large-diameter portion 190 is brought into contact with the end wall of the guide groove 176 to be aligned in the fixing groove portion 180 as depicted in FIG. 18B. Thereafter, like the example of the first restriction mechanism 152, as shown in FIG. 18C, the large-diameter portion 190 is fitted into the fixing groove portion 180, the second knob portion 138 is locked with respect to the pedestal 184, and the base bottom portion 60 and the third coupling link 72c are locked. This state is an in-accommodation downward movement limit when the binocular tube 68b is accommodated.

Here, an in-accommodation movable range of the third coupling link 72c with respect to the base bottom portion 60 is defined by a state in which the large-diameter portion 190 is in contact with the lower end part of the moving groove portion 178 and a state in which the large-diameter portion 190 is fitted in the fixing groove portion 180. Further, an in-use downward movement limit and an in-accommodation downward movement limit of the binocular tube 68b define an in-accommodation upward/downward movement range of the binocular tube 68b.

In the actual accommodating operation, the accommodating operation based on the backward movement of the binocular tube 68b is combined with the accommodating operation based on the downward movement of the binocular tube 68b. Combining the in-accommodation upward/downward movement range of the binocular tube 68b with the in-accommodation frontward/backward movement range of the same define the in-accommodation movement range of the binocular tube 68b.

Figure 19:
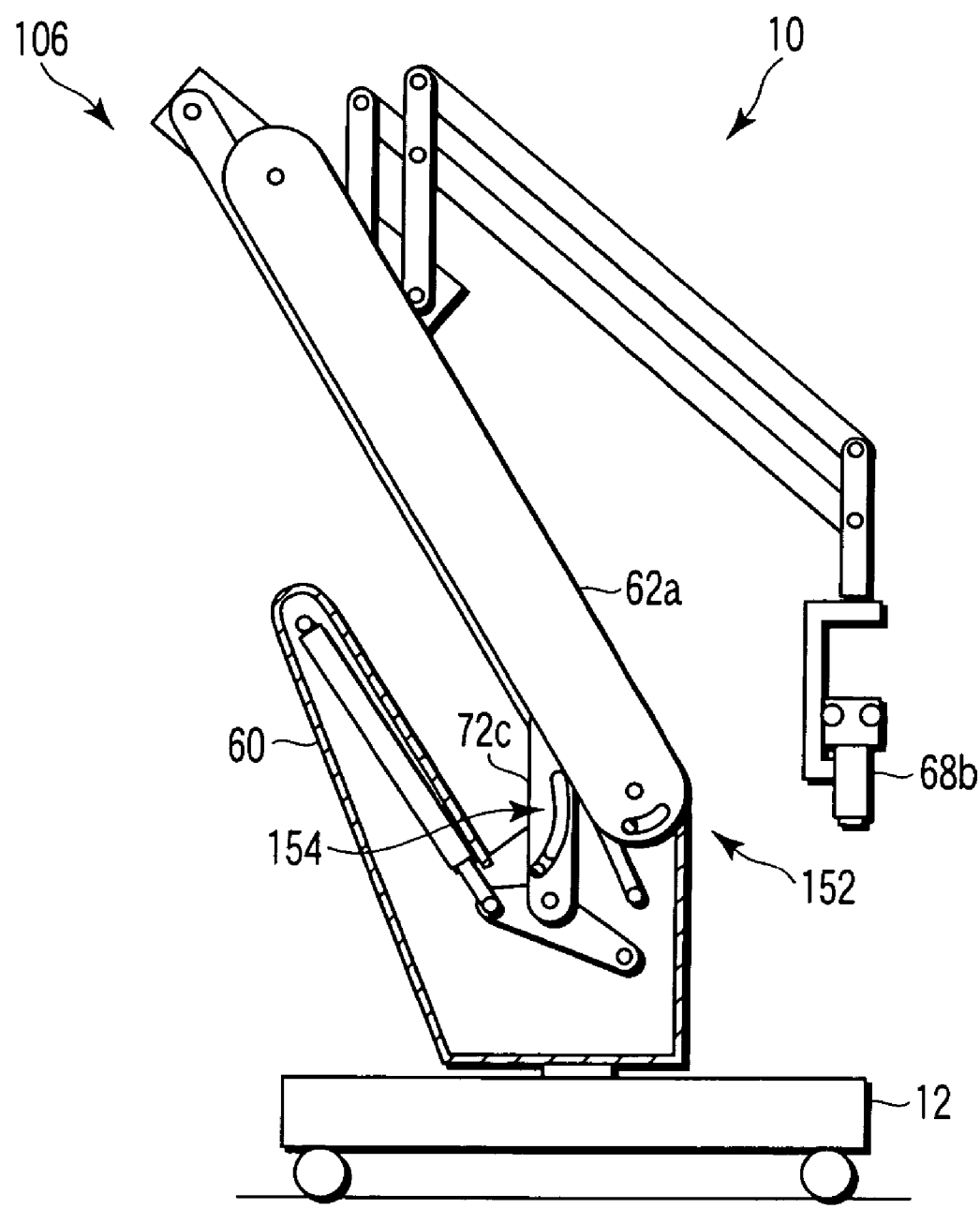
FIG. 19 is a cross-sectional view showing the surgical microscope according to the third embodiment of the present invention in an accommodation state.

The binocular tube 68b is moved in the in-accommodation movement range to shift the holding portion 106 to such an accommodation state as shown in FIG. 19. In this accommodation state, compact folding of the plurality of links in the holding portion 106 is allowed, the binocular tube 68b is arranged at a sufficiently low position above the base 12, and a height of the holding portion 106 is an appropriate height. Furthermore, when the vertical link 62a and the third coupling link 72c are fixed with respect to the base bottom portion 60, the holding portion 106 is held in the accommodation state. That is, the first and second restriction mechanisms 152 and 154 also serve as a fixing mechanism which holds the holding portion 106 in the accommodation state.

Thus, the device having the above-described structure demonstrates the following effects. When using the microscope body, the first and second restriction mechanisms 152 and 154 restrict a relative movable range of the vertical link 62a and the base bottom portion 60 and a relative movable range of the third coupling link 72c and the base bottom portion 60 within the in-use movable range, thereby moving and holding the binocular tube 68b within the in-use movement range. Moreover, when accommodating the binocular tube 68b, the first and second restriction mechanisms 152 and 154 restrict a relative movable range of the vertical link 62a and the base bottom portion 60 and a relative movable range of the third coupling link 72c and the base bottom portion 60 within the in-accommodation movable range different from the in-use movable range, whereby the binocular tube 68b is moved within the in-accommodation movable range which is partly different from the in-use movable range so that the holding portion 106 is shifted to the accommodation state where compact-folding of the holding portion 106 is allowed.

That is, a dedicated connecting portion which allows compact folding of the holding portion 106 is not provided, thereby avoiding a reduction in operability of the holding portion 106 due to an increase in size or weight of the holding portion 106. Therefore, the binocular tube 68b can be readily and accurately moved by using the holding portion 106 when using the binocular tube 68b, and compact folding of the holding portion 106 is allowed when accommodating the binocular tube 68b.

It is to be noted that a shape of the guide groove 156 or 176 can be any shape as long as the restriction groove portion 162 or 182 separates the moving groove portion 158 or 178 in which the large-diameter portion 168 or 190 is moved when using the binocular tube 68b from the fixing groove portion 160 or 180 in which the large-diameter portion 168 or 190 is moved when accommodating the binocular tube 68b. Moreover, the moving groove portion 158 or 178 may have any shape as long as it does not obstruct a movement of the large-diameter portion 168 or 190. This is also applied to the following embodiments.

The restriction mechanism used in the third embodiment can be applied to apparatuses other than the surgical microscope according to the present invention. Reference embodiments of the surgical microscope having the restriction mechanism will now be described.

A surgical microscope according to a first reference embodiment will now be described with reference to FIGS. 20 to 27. Like reference numerals denote the same structures as those in the third embodiment, thereby eliminating their explanation. A base bottom portion 198 of a surgical microscope 110 according to this reference embodiment has a substantially-inverted-L shape. That is, the base bottom portion 198 has a main body portion 198a extending in a horizontal direction, and an upright portion 198b extends from one side end part of an upper surface of this main body portion 198a (a right end portion in FIG. 20) along a vertical direction. A notch portion 202 which is obliquely notched is formed at the other side end part of the upper part of the main body portion 198a. On the other hand, a knob portion 200 having the same structure as the third embodiment is arranged on the upright portion 198b.

Figure 22A:
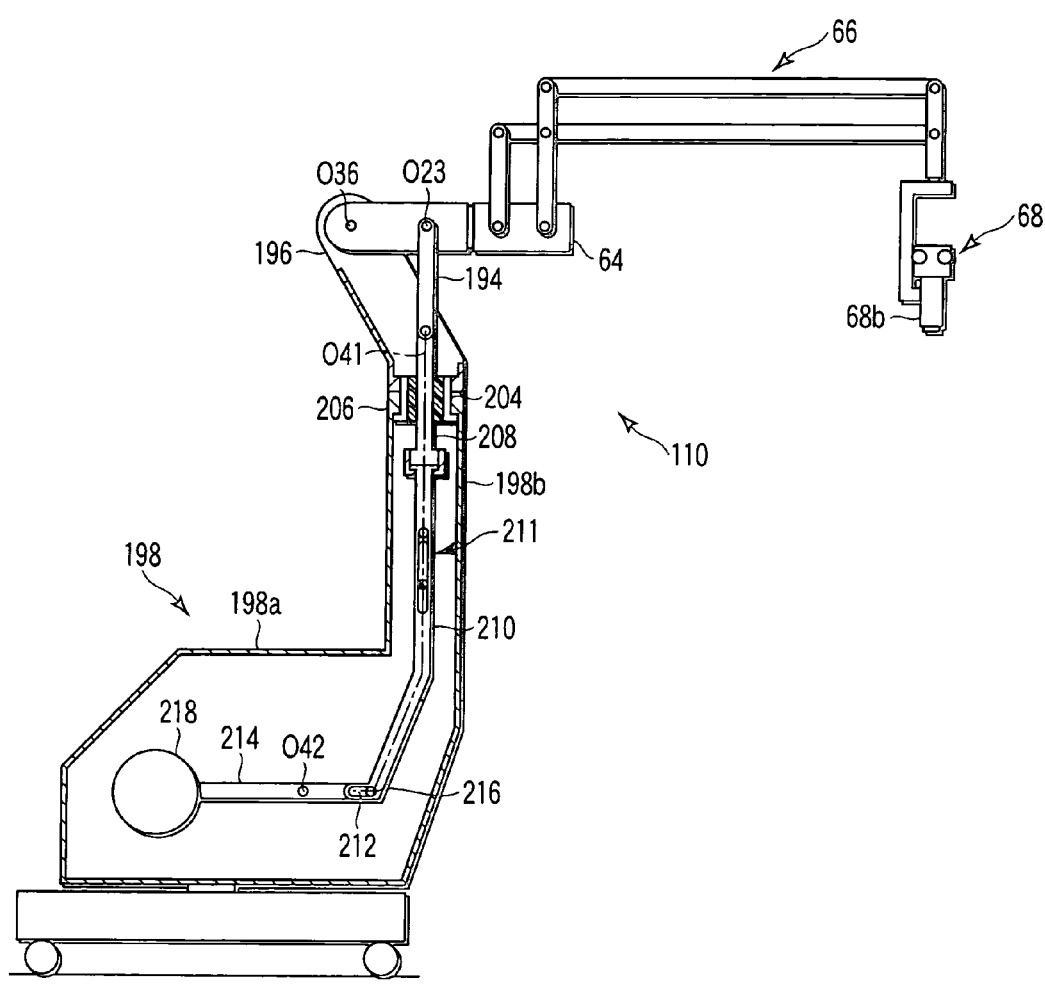
FIG. 22A is a cross-sectional view showing the surgical microscope according to the first reference embodiment of the present invention.

A support member 196 is connected with a top part of the base bottom portion 198. This support member 196 extends from a base end part toward an leading end part upward along the vertical direction and a direction apart from a microscope portion 68 (a left upper direction in FIG. 20). The support member 196 can freely rotate around a 41st rotation axis O41 with respect to the base bottom portion 198, the 41st rotation axis O41 extending in the vertical direction through the center of the top part of the base bottom portion 198. That is, as shown in FIG. 22A, a flange cylindrical portion 204 protruding downward along the vertical direction is arranged below the support member 196. On the other hand, a flange portion 206 is arranged at the top part of the base bottom portion 198. When the flange cylindrical portion 204 of the support member 196 is fitted in the flange portion 206 of the base bottom portion 198, the support member 196 is connected with respect to the base bottom portion 198 to be rotatable around the 41st rotation axis O41.

Figure 20:
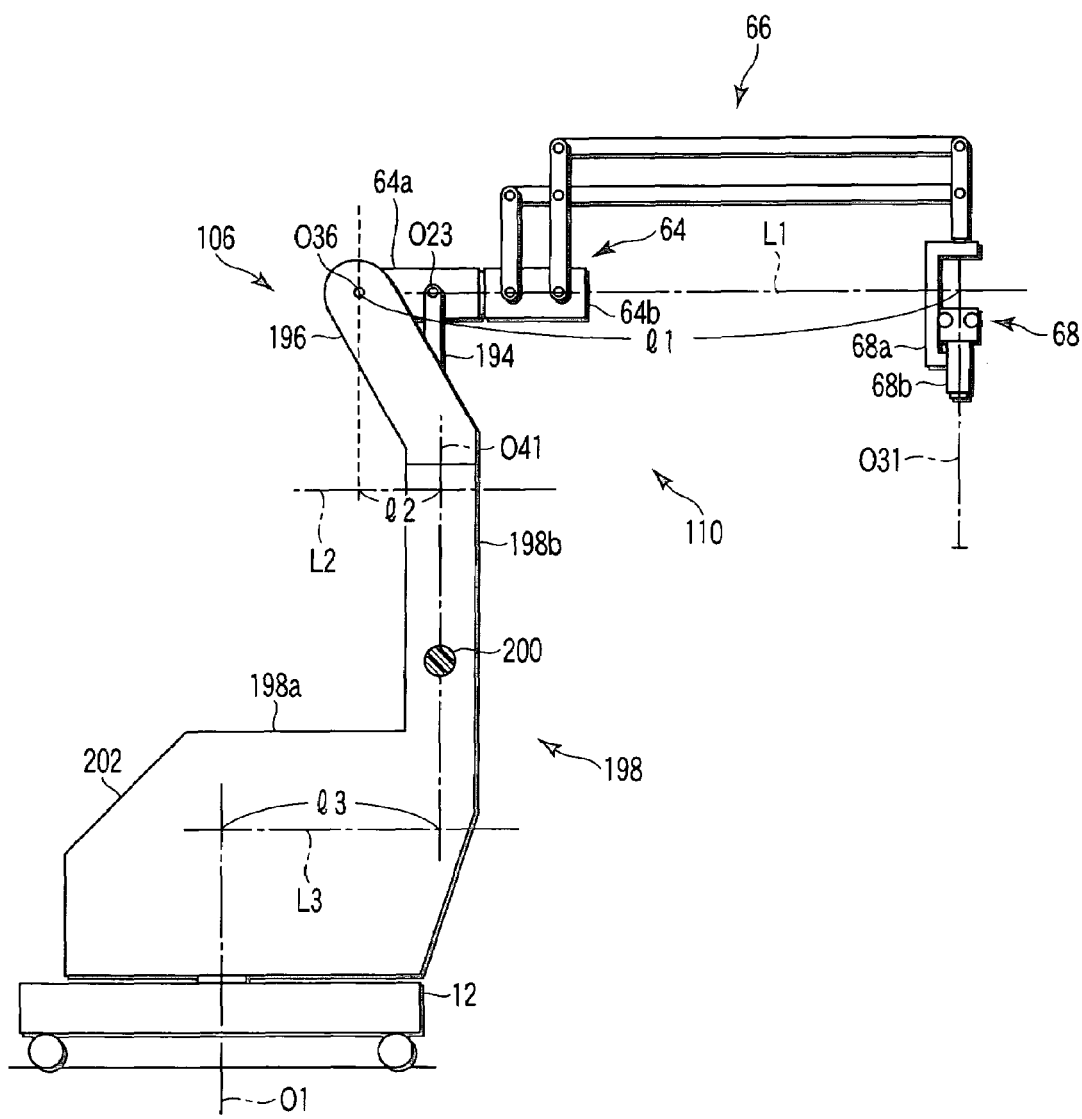
FIG. 20 is a side view showing a surgical microscope according to a first reference embodiment of the present invention in a state where a microscope body is set at an in-use forward movement limit.

As shown in FIG. 20, the end part of the support member 196 is pivoted at a position of the 36th rotation axis O36 of a first connection block 64a of an arm support portion 64. Additionally, the arm support portion 64 can revolve around the 36th rotation axis O36 with respect to the support member 196.

A vertical movement arm portion 66 having the same structure as the third embodiment is connected with the arm support portion 64. Furthermore, a microscope portion 68 having the same structure as the third embodiment is connected with the vertical movement arm portion 66.

Furthermore, an upper end part of a first connection link 194 is pivoted at a position of a 23rd rotation axis O23 of the first connection block 64a of the arm support portion 64. As shown in FIG. 22A, the first connection link 194 extends in the support member 196 along the vertical direction. A lower end part of the first connection link 194 is pivoted on an upper end part of a second connection link 208. The second connection link 208 is inserted into a guide hole extended in the flange portion 206 of the support member 196 along the vertical direction. The second connection link 208 can slide in the guide hole along the vertical direction.

A lower end part of the second connection link 208 is connected with an upper end part of a third connection link 210 like the connection between the top part of the base bottom portion 198 and the lower end part of the support member 196. That is, the second connection link 208 can freely rotate around its own central axis (the 41st rotation axis O41) with respect to the third connection link 210.

An upper part of the third connection link 210 extends downwardly in the upright portion 198b of the base bottom portion 198 along the vertical direction, and an intermediate part of the third connection link 210 extends downwardly in the main body portion 198a along the vertical direction as well as a direction apart from the binocular tube 68b. Additionally, a lower part of the third connection link 210 extends in a horizontal direction as well as a direction apart from the binocular tube 68b. A link hole 212 extending in a longitudinal direction of the lower part is formed in this lower part.

One end part of a fourth connection link 214 is connected with the lower part of the third connection link 210 in such a manner that it can slide along the central axis direction of the lower part of the third connection link 210. That is, a link shaft 216 is provided to protrude from one end part of the fourth connection link 214 in a direction vertical to the central axis direction of the fourth connection link 214, and this link shaft 215 is slidably inserted into the link hole 212 of the third connection link 210.

A central part of the fourth connection link 214 is pivoted on the base bottom portion 198. Further, the fourth connection link 214 can revolve around a 42nd rotation axis O42 with respect to the base bottom portion 198, the 42nd rotation axis O42 extending in a substantially horizontal direction through the central part of the fourth connection link 214. A counterbalance 218 which offsets a rotation moment around a 23rd rotation axis O23 generated by weights of the microscope portion 68 and the vertical movement arm portion 66, or the like is arranged at the other end part of the fourth connection link 214.

Figure 22B:
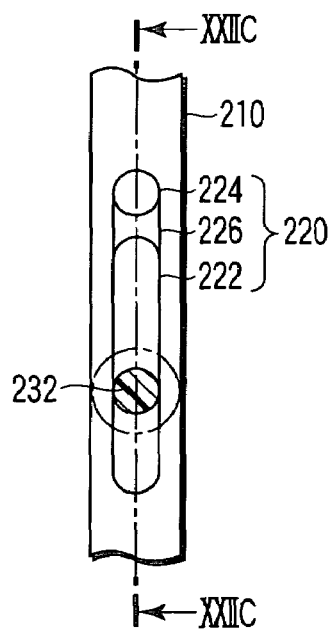
FIG. 22B is a cross-sectional view showing a restriction mechanism of the surgical microscope according to the first reference embodiment of the present invention.

The same restriction mechanism 211 as the second restriction mechanism 154 according to the third embodiment (see FIGS. 10D and 10E) is arranged with respect to the base bottom portion 198 and the third connection link 210. That is, as shown in FIG. 22B, a guide groove 220 extending in the longitudinal direction of the third connection link 210 is formed in the third connection link 210. An elongated groove-like moving groove portion 222 is arranged on a lower side of this guide groove 220, a substantially circular fixing groove portion 224 is arranged at an upper part, and a restriction groove portion 226 is arranged between the moving groove portion 222 and the fixing groove portion 224. A width of the moving groove portion 222 and a diameter of the fixing groove portion 224 are slightly larger than a diameter of the large-diameter portion 232 of the shaft portion 230 of the knob portion 200 depicted in FIG. 22C. Moreover, as shown in FIG. 22B, the restriction groove portion 226 has a width which is substantially equal to the width of the moving groove portion 222 and the diameter of the fixing groove portion 224.

Figure 22C:
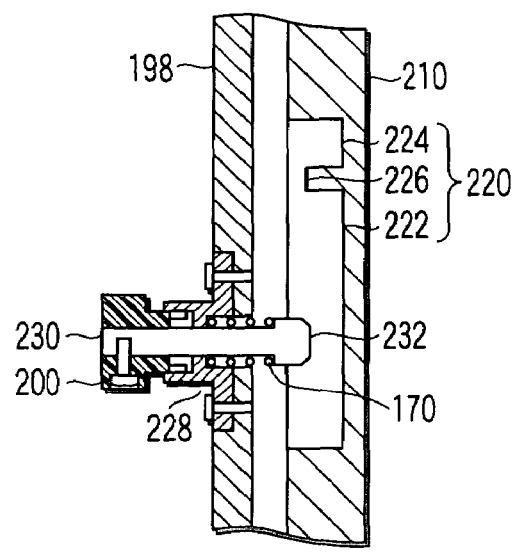
FIG. 22C is a cross-sectional view showing the restriction mechanism of the surgical microscope according to the first reference embodiment of the present invention taken along a line XXIIC-XXIIC in FIG. 22B.

Additionally, as shown in FIG. 22C, the knob portion 200 and the pedestal 228 are arranged on the base bottom portion 198. The knob portion 200 has the shaft portion 230 and the large-diameter portion 232. A spring 170 is stretched and arranged between the pedestal 228 and the large-diameter portion 232. In this embodiment, a stopper pin is not arranged in the knob portion 200, and a lock hole is not arranged in the pedestal 228. Alternatively, the knob portion 200 is attached on the pedestal 228 to be protrusible/retractable along the axial direction by screwing a male screw formed on the knob portion into a female screw formed in the pedestal 228.

Referring to FIG. 20, an axis vertically extending with respect to the 31st rotation axis O31 as the central axis of the binocular tube 68b and the 36th rotation axis O36 of the end part of the support member 196 will be referred to as a first axis L1. Further, a distance between the 31st rotation axis O31 and the 36th rotation axis O36 will be referred to as l1. Furthermore, an axis vertically extending with respect to the 36th rotation axis O36 and the 41st rotation axis O41 as the rotation central axis of the support member 196 will be referred to as a second axis L2. Moreover, a distance between the 36th rotation axis O36 and the 41st rotation axis O41 will be referred to as l2. Additionally, an axis vertically extending with respect to the 41st rotation axis O41 and the first rotation axis O1 as the rotation central axis of the base bottom portion 198 will be referred to as a third axis L3. Further, a distance between the 41st rotation axis O41 and the first rotation axis O1 will be referred to as l3.

A function of the surgical microscope 110 having the above-described structure according to this embodiment will now be described. When using the surgical microscope 110, the binocular tube 68b is manually moved to a desired position suitable for observation as described below.

When moving the binocular tube 68b in a front-and-back direction, the support member 196 is rotated around the 21st rotation axis O21 with respect to the base bottom portion 198, and the base bottom portion 198 is rotated around the first rotation axis O1 with respect to the base 12. In this manner, when an angle formed between the second axis L2 and the third axis L3 is changed, the movement of the binocular tube 68b in the front-and-back direction is realized.

As shown in FIG. 20, a state in which the binocular tube 68b is arranged on the upright portion 198b side of the base bottom portion 198 and the second axis L2 and the third axis L3 are arranged in parallel is a forward movement limit of the binocular tube 68b. At this time, a distance between the 31st rotation axis O31 and the first rotation axis O1 is l1+l3−l2.

Figure 21:
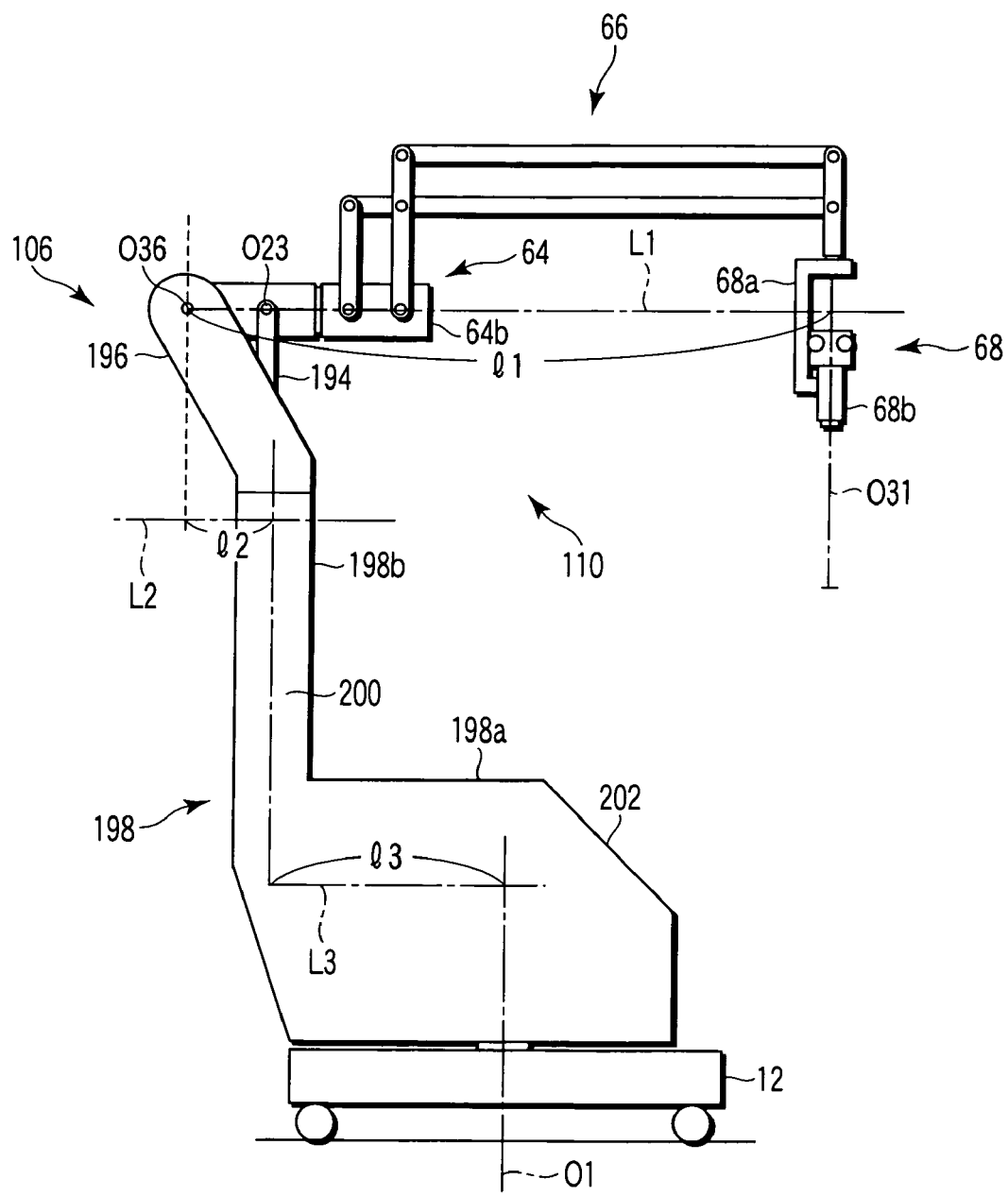
FIG. 21 is a side view showing the surgical microscope according to the first reference embodiment of the present invention in a state where the microscope body is set at an in-use backward movement limit.

It is assumed that an angle formed between the second axis L2 and the third axis L3 in this state is 180°. When the binocular tube 68b is moved rearward, the base bottom portion 198 is rotated 360° with respect to the base 12, the binocular tube 68b is arranged on the side of the base bottom portion 198 opposite to the upright portion 198b as shown in FIG. 21, and the angle formed between the second axis L2 and the third axis L3 is reduced to 0°. This state is an in-use backward movement limit of the binocular tube 68b. The in-use forward movement limit and the in-use backward movement limit of the binocular tube 68b define an in-use frontward/backward movement range of the binocular tube 68b. At this time, a distance between the 31st rotation axis O31 and the first rotation axis O1 becomes l1–l2–l3.

Figure 23A:
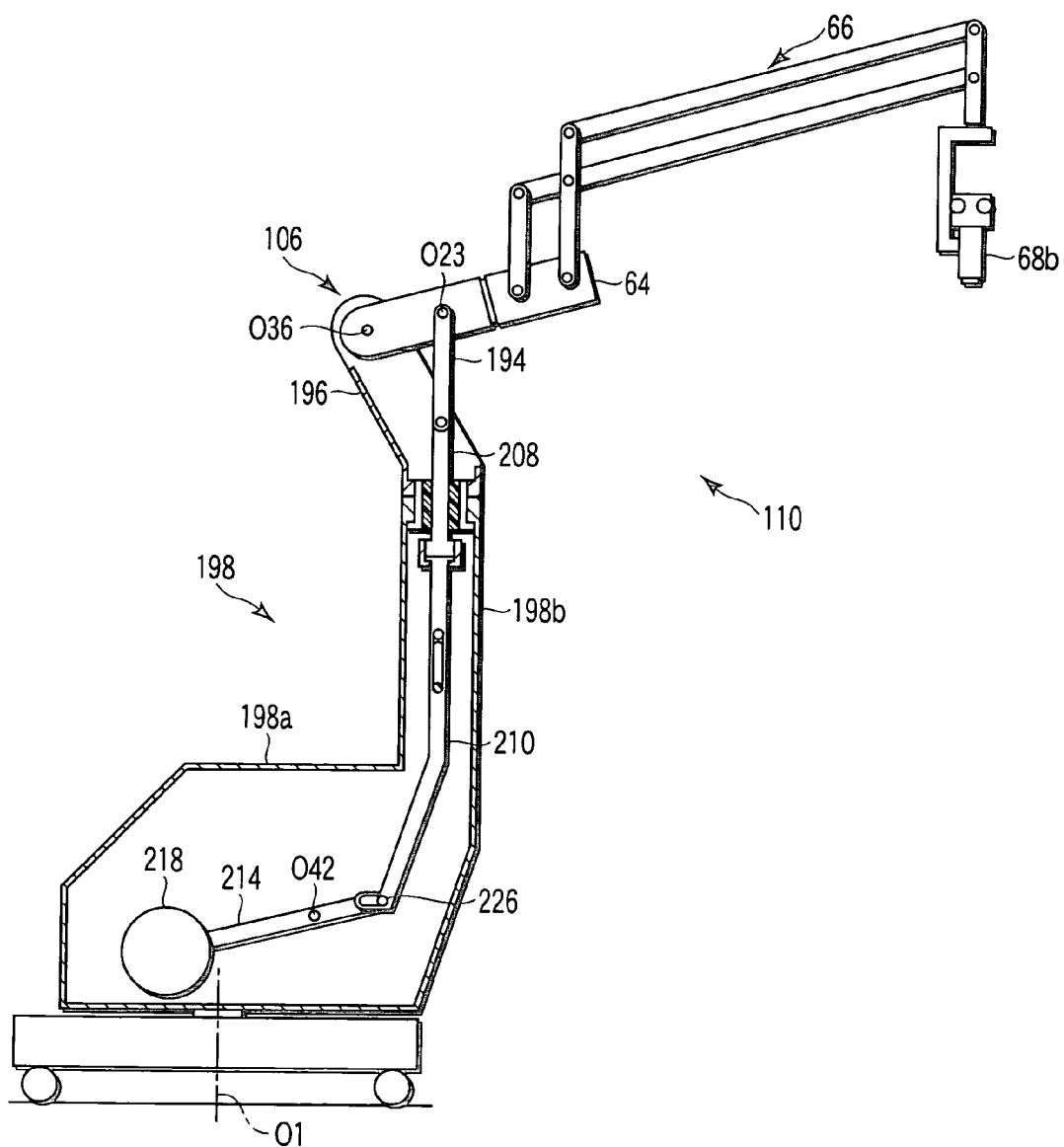
FIG. 23A is a cross-sectional view showing the surgical microscope according to the first reference embodiment of the present invention in a state where the microscope body is set at an in-use upward movement limit.

As shown in FIG. 23A, in case of moving up the binocular tube 68b, the binocular tube 68b is pushed toward a right above position. As a result, the vertical movement arm portion 66 is revolved around the 23rd rotation axis O23 in a counterclockwise direction in the drawing. Further, the first to third connection links 194, 208 and 210 are moved up, and one end part of the fourth connection link 214 is revolved upward around the 42nd rotation axis O42. As a result, the counterbalance 218 at the other end part of the fourth connection link 214 is revolved downward around the 42nd rotation axis O42.

Here, after the binocular tube 68b is moved to a desired upper position, when a hand is released from the binocular tube 68b, a function of the counterbalance 218 offsets a rotation moment around the third rotation axis O3, whereby the binocular tube 68b stands still at this position.

Figure 23B:
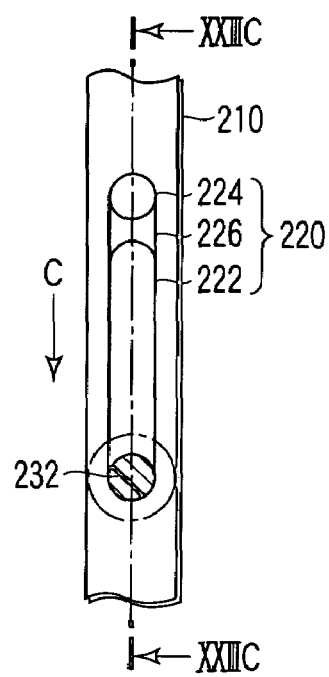
FIG. 23B is a cross-sectional view showing the restriction mechanism of the surgical microscope according to the first reference embodiment of the present invention in a state where the microscope body is set at the in-use upward movement limit.
Figure 23C:
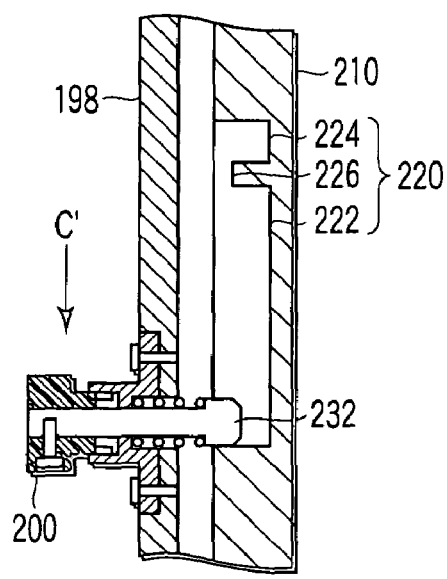
FIG. 23C is a cross-sectional view showing the restriction mechanism of the surgical microscope according to the first reference embodiment of the present invention in FIG. 23B in a state where the microscope body is set at the in-use upward movement limit taken along a line XXIIIC-XXIIIC.

During the upward movement of the binocular tube 68b, as indicated by arrows C and C' in FIGS. 23B and 23C, the large-diameter portion 232 of the knob portion 200 is relatively moved in the moving groove portion 222 of the third connection link 210 in a direction opposite to the fixing groove portion 224. When the large-diameter portion 232 comes into contact with the end wall of the moving groove portion 222, the upward movements of the first to third connection links 194, 208 and 210 are restricted, thereby limiting the revolving movement of the arm support portion 64. In this manner, the upward movement of the binocular tube 68b is restricted. This state is an in-use upward movement limit of the binocular tube 68b.

Figure 24A:
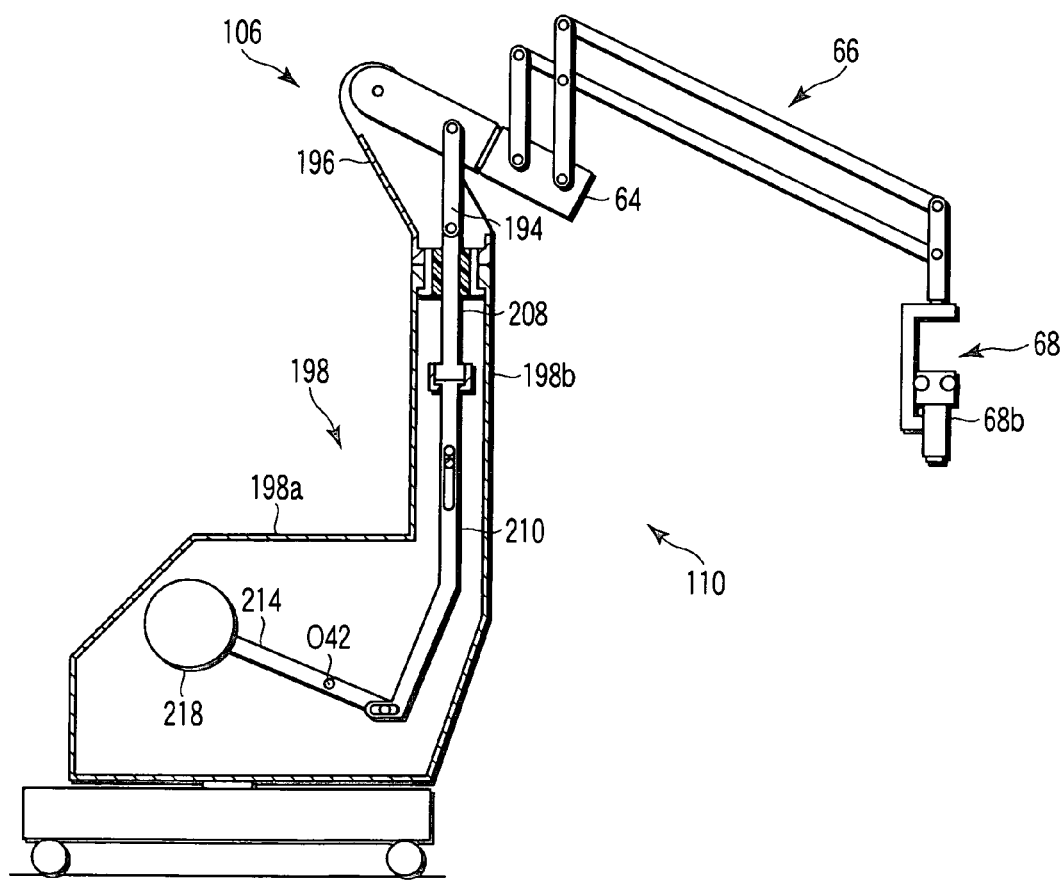
FIG. 24A is a cross-sectional view showing the surgical microscope according to the first reference embodiment of the present invention in a state where the microscope body is set at an in-use downward movement limit.
Figure 24B:
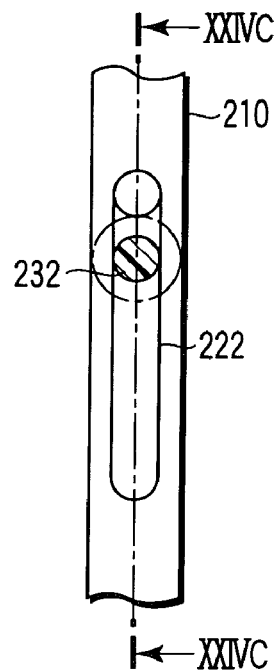
FIG. 24B is a cross-sectional view showing the restriction mechanism of the surgical microscope according to the first reference embodiment of the present invention in a state where the microscope body is set at the in-use downward movement limit.
Figure 24C:
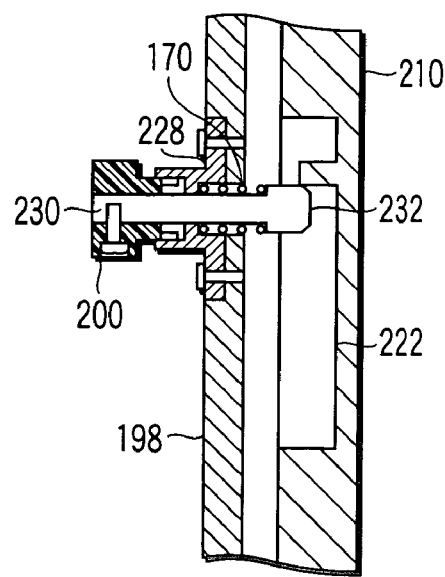
FIG. 24C is a cross-sectional view showing the restriction mechanism of the surgical microscope according to the first reference embodiment of the present invention in a state where the microscope body is set at the in-use downward movement limit taken along a line XXIVC-XXIVC in FIG. 24B.

As shown in FIG. 24A, in case of moving down the binocular tube 68b, a function opposite to that of the upward movement of the microscope body occurs. As shown in FIGS. 24B and 24C, when the large-diameter portion 232 comes into contact with the end wall of the moving groove portion 222, the downward movements of the first to third connection links 194, 208 and 210 are restricted, thereby limiting the revolving movement of the arm support portion 64. This state is an in-use downward movement limit of the binocular tube 68b.

Here, an in-use movable range of the third connection link 210 with respect to the base bottom portion 198 is defined by a state in which the large-diameter portion 232 is in contact with the upper end wall of the moving groove portion 222 and a state in which the large-diameter portion 232 is in contact with the lower end wall of the same. An in-use upward movement limit and an in-use downward movement limit of the binocular tube 68b define an in-use upward/downward movement range of the binocular tube 68b.

Like the third embodiment, the movement in the front-and-back direction and the movement in the up-and-down direction of the binocular tube 68b can be combined with each other. Furthermore, combining an in-use forward/backward movement range of the binocular tube 68b with an in-use upward/downward movement range of the same define an in-use movement range of the binocular tube 68b. Like the third embodiment, the microscope body is moved to a desired position by a rotating operation of the first arm 68a and the second connection block 64b of the arm support portion 64 in addition to the movement of the binocular tube 68b in the front-and-back direction and the up-and-down direction.

After use of the binocular tube 68b, the following accommodating operation is carried out when accommodating the binocular tube 68b. An accommodating operation based on the backward movement of the binocular tube 68b and an accommodating operation based on the downward movement of the binocular tube 68b will be separately described in order to simplify the explanation.

In the accommodating operation based on the backward movement of the binocular tube 68b, the binocular tube 68b is set to an in-use backward movement limit. This state is also an in-accommodation backward movement limit of the binocular tube 68b. That is, an in-accommodation forward/backward movement range of the binocular tube 68b is not provided.

Figure 25A:
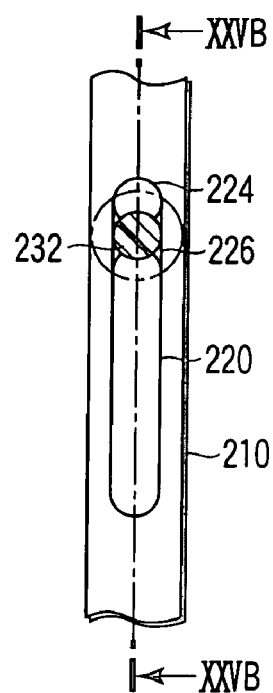
FIG. 25A is a cross-sectional view showing the restriction mechanism of the surgical microscope according to the first reference embodiment of the present invention in a state where the microscope body is set between the in-use downward movement limit and an in-accommodation downward movement limit.
Figure 25B:
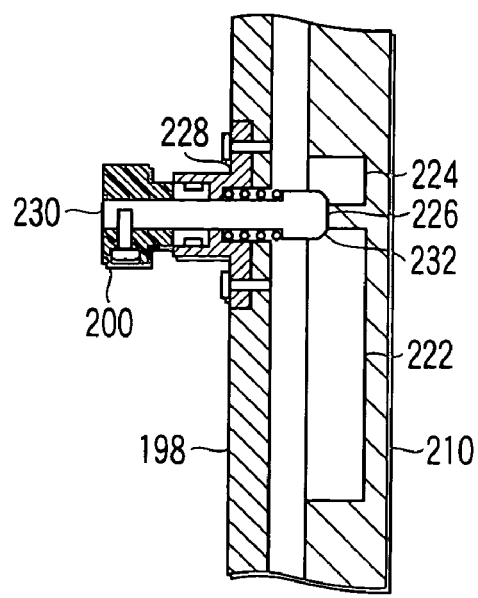
FIG. 25B is a cross-sectional view showing the restriction mechanism of the surgical microscope according to the first reference embodiment of the present invention in a state where the microscope body is set between the in-use downward movement limit and the in-accommodation downward movement limit taken along a line XXVB-XXVB in FIG. 25A.

In the accommodating operation based on the downward movement of the binocular tube 68b, the binocular tube 68b is set to such an in-use downward movement limit as shown in FIGS. 24A, 24B and 24C. Moreover, the knob portion 200 is turned with respect to the pedestal 228 to pull out the male screw from the female screw. As a result, the knob portion 200 is outwardly moved in the axial direction with respect to the pedestal 228 by an impetus of the spring 170. Additionally, the large-diameter portion 232 of the shaft portion 230 is outwardly moved in the axial direction, and contact with respect to the end wall of the moving groove portion 222 is released. In this state, the binocular tube 68b is moved down, the first to third connection links 194, 208 and 210 are moved up, and the large-diameter portion 232 is relatively moved from the moving groove portion 222 to the fixing groove portion 224 by using the restriction groove portion as shown in FIGS. 25A and 25B.

Figure 26A:
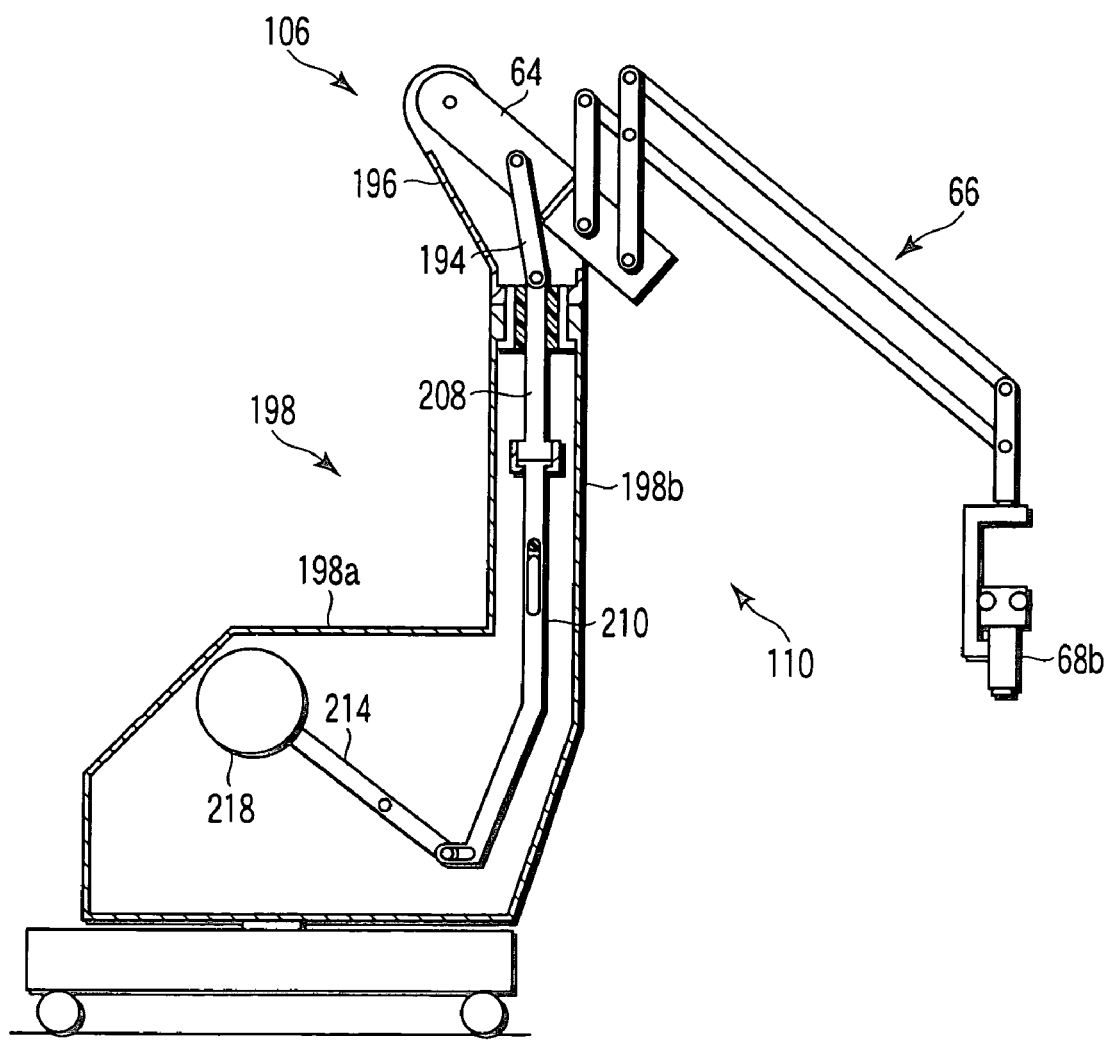
FIG. 26A is a cross-sectional view showing the surgical microscope according to the first reference embodiment of the present invention in a state where the microscope body is set at the in-accommodation downward movement limit.
Figure 26B:
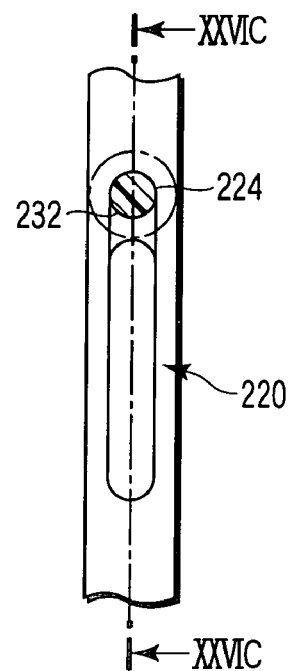
FIG. 26B is a cross-sectional view showing the restriction mechanism of the surgical microscope according to the first reference embodiment of the present invention in a state where the microscope body is set at the in-accommodation downward movement limit.
Figure 26C:
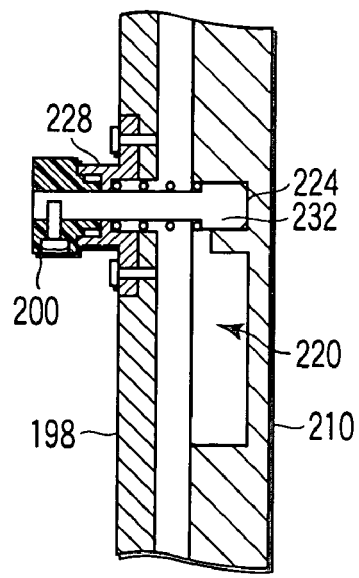
FIG. 26C is a cross-sectional view showing the restriction mechanism of the surgical microscope according to the first reference embodiment of the present invention in a state where the microscope body is set at the in-accommodation downward movement limit taken along a line XXVIC-XXVIC in FIG. 26B.

Further, the binocular tube 68b is moved down to downwardly move the first to third connection links 194, 208 and 210 as shown in FIG. 26A, and the large-diameter portion 232 is brought into contact with the end wall of the guide groove 220 to be aligned in the fixing groove portion 224. Thereafter, the knob portion 200 is turned with respect to the pedestal 228 to be inwardly moved in the axial direction, the large-diameter portion 232 is fitted in the fixing groove portion 224 as shown in FIG. 26C, and the base bottom portion 198 and the third connection link 210 are locked. This state is an in-accommodation downward movement limit of the binocular tube 68b.

Here, an in-accommodation movable range of the third connection link 210 with respect to the base bottom portion 198 is defined by a state in which the large-diameter portion 232 is in contact with the upper end part of the moving groove portion 222 and a state in which the large-diameter portion 232 is fitted in the fixing groove portion 224. Furthermore, an in-use downward movement limit and an in-accommodation movement limit of the binocular tube 68b define an in-accommodation upward/downward movement range of the binocular tube 68b.

Like the third embodiment, in the actual accommodating operation, the accommodating operation based on the backward movement of the binocular tube 68b is combined with the accommodating operation based on the downward movement of the binocular tube 68b. Moreover, the in-accommodation upward/downward movement range of the binocular tube 68b defines an in-accommodation movement range of the binocular tube 68b.

Figure 27:
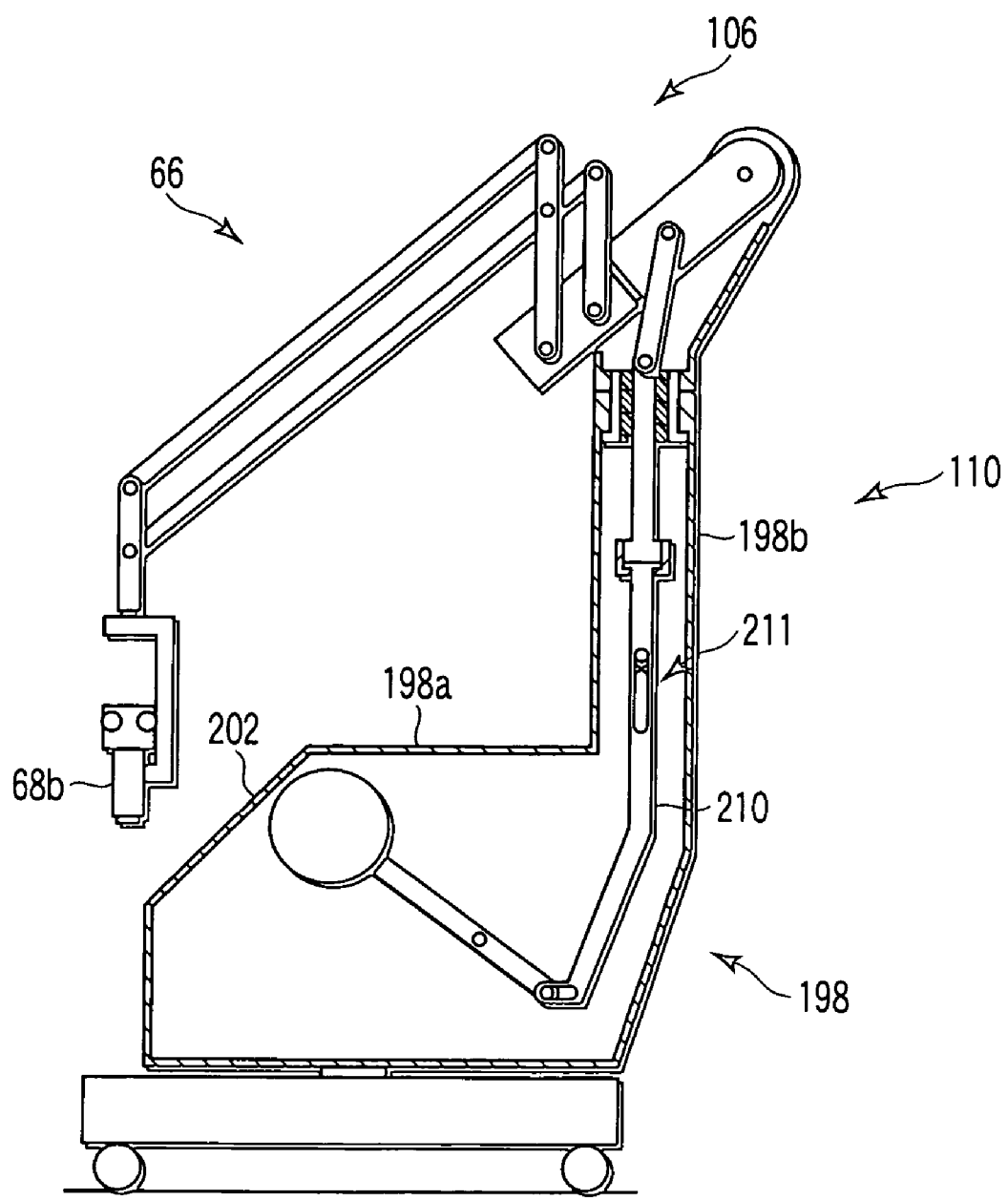
FIG. 27 is a cross-sectional view showing the surgical microscope according to the first reference embodiment of the present invention in an accommodation state.

The binocular tube 68b is moved in the in-accommodation movement range to shift the surgical microscope 10 to such an accommodation state as shown in FIG. 27. In this accommodation state, compact folding of the plurality of links of the holding portion 106 is allowed, the binocular tube 68b is arranged at a sufficiently low position above the notch portion 202, and a height of the holding portion 106 is an appropriate height. Additionally, when the third connection link 210 is fixed with respect to the base bottom portion 198, the surgical microscope 110 is held in the accommodation state. That is, the restriction mechanism 211 according to this embodiment also serves as a fixing mechanism which holds the surgical microscope 110 in the accommodation state.

Thus, the surgical microscope having the above-mentioned structure demonstrates the following effects in addition to those of the third embodiment. The knob portion 200 is arranged at a high position with respect to the base 12. Therefore, an operator can manipulate the knob portion 200 in a comfortable posture.

Further, the knob portion 200 is attached to the pedestal 228 to be protrusible/retractable in the axial direction by screwing the knob portion 200 with respect to the pedestal 228. Furthermore, when accommodating the binocular tube 68b, the knob portion 200 is turned with respect to the pedestal 228 to be inwardly moved in the axial direction, the large-diameter portion 232 is fitted in the fixing groove portion 224, and the based bottom portion 198 and the third connection link 210 are locked, thereby holding the holding portion 106 in the accommodation state. Accordingly, the holding portion 106 is assuredly held in the accommodation state.

Figure 28:
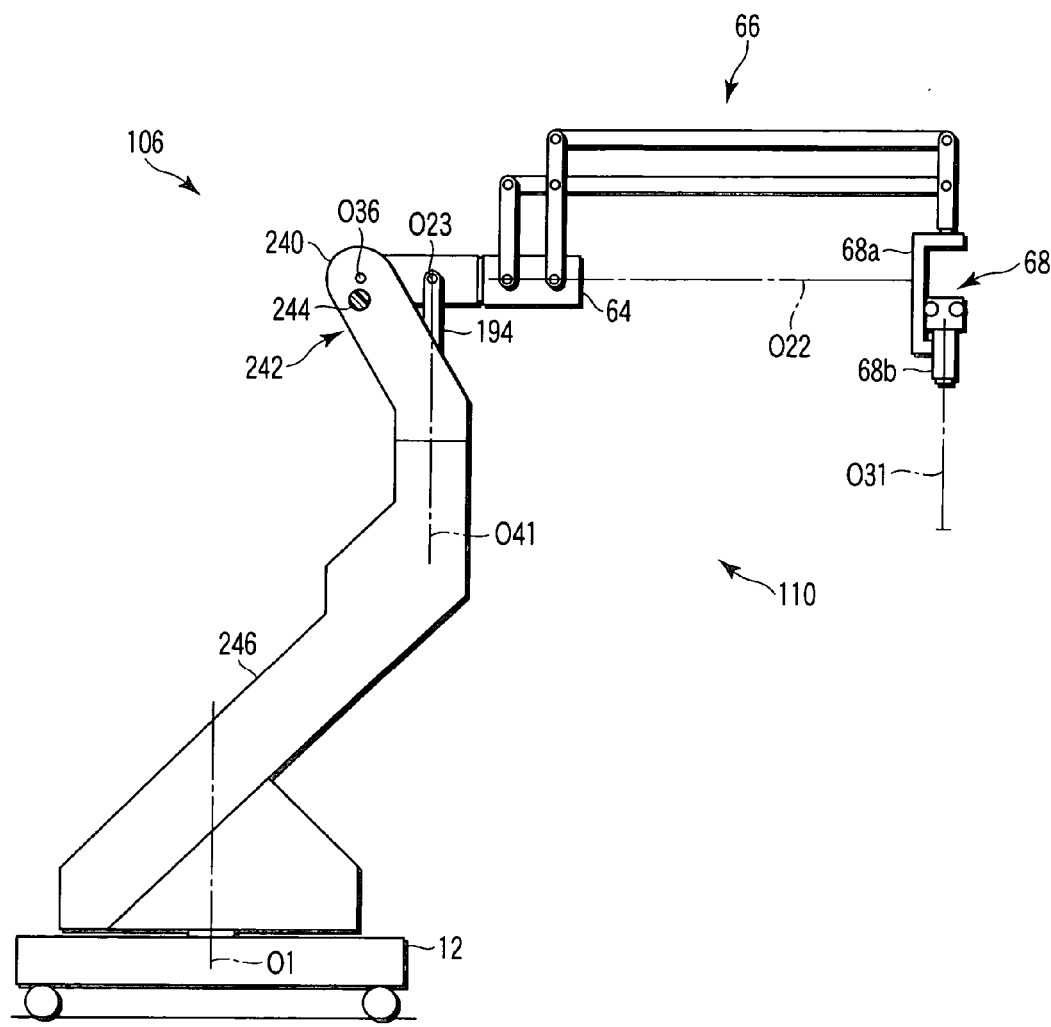
FIG. 28 is a side view showing a surgical microscope according to a second reference embodiment of the present invention.

FIGS. 28 to 34 show a second reference embodiment according to the present invention. Like reference numerals denote structures equal to those in the first reference embodiment, thereby eliminating their explanation. As shown in FIG. 28, a surgical microscope 110 according to this reference embodiment has a microscope portion 68, a vertical movement arm portion 66, an arm support portion 64, a first connection link 194 and a support member 240 which are substantially equal to those in the first reference embodiment. It is to be noted that a knob portion 244 of a later-described restriction mechanism 242 is arranged between the arm support portion 64 and the support member 240. Moreover, a base bottom portion 246 has a shape obliquely inclined in a vertical direction, and the restriction mechanism is not arranged in the base bottom portion 246.

Figure 29A:
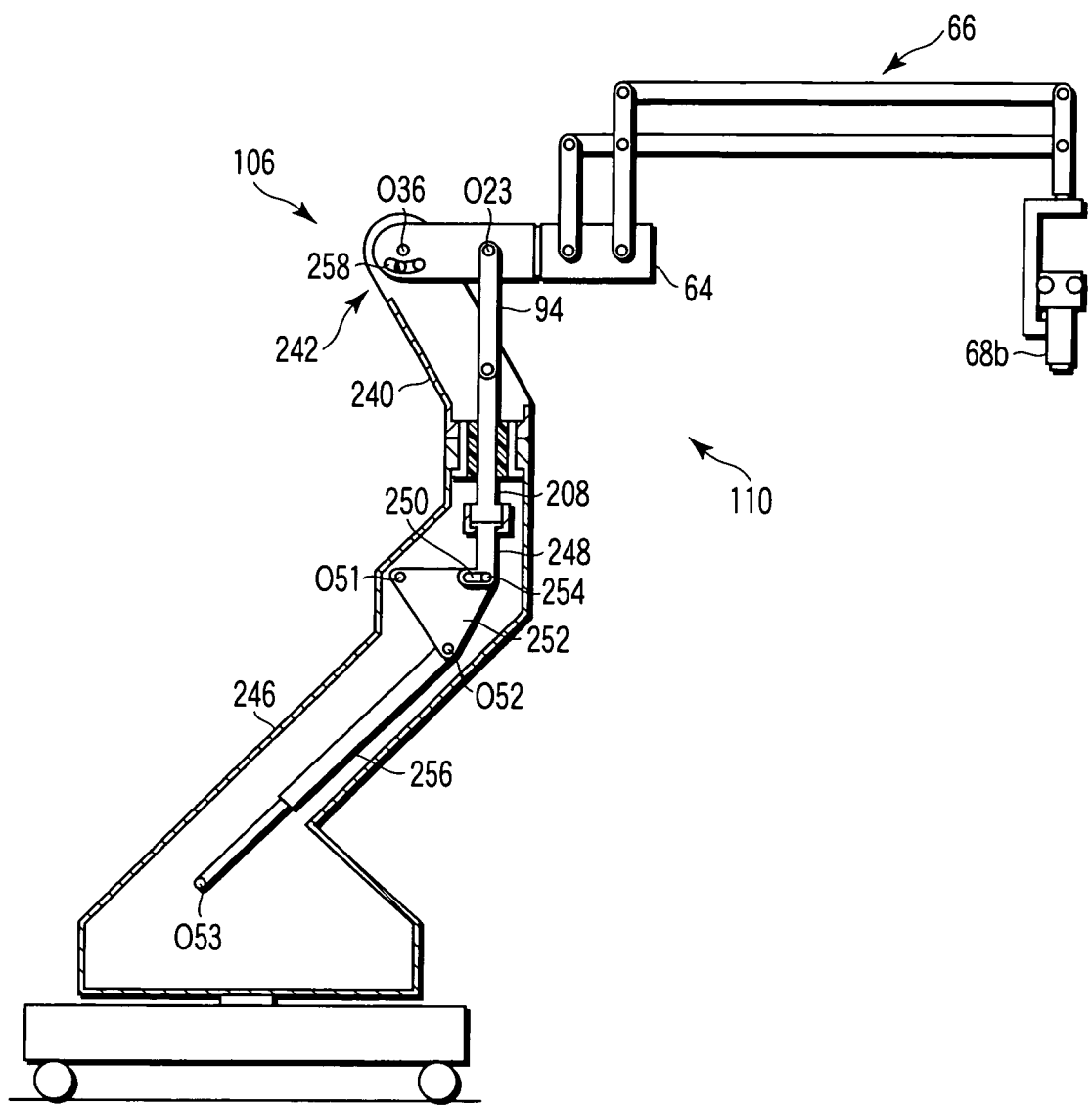
FIG. 29A is a cross-sectional view showing the surgical microscope according to the second reference embodiment of the present invention.
Figure 29B:
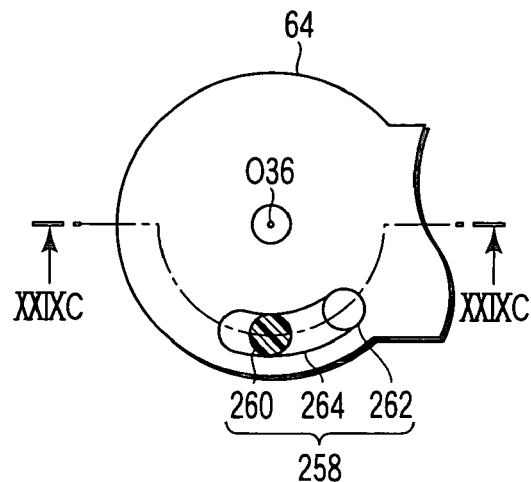
FIG. 29B is a cross-sectional view showing a restriction mechanism of the surgical microscope according to the second reference embodiment of the present invention.
Figure 29C:
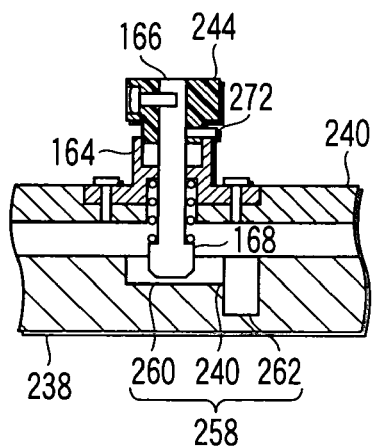
FIG. 29C is a cross-sectional view showing the restriction mechanism of the surgical microscope according to the second reference embodiment of the present invention taken along a line XXIXC-XXIXC in FIG. 29C.
Figure 29D:
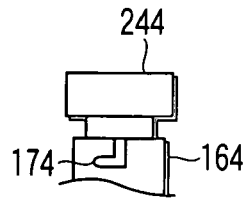
FIG. 29D is a side view showing a knob portion and a pedestal of the restriction mechanism of the surgical microscope according to the second reference embodiment of the present invention.

As shown in FIG. 29A, the surgical microscope 110 according to this embodiment has a second connection link 208 which is equal to that in the first reference embodiment. An upper end part of a third connection link 248 is connected with a lower end part of this second connection link 208 like the first reference embodiment. A lower end part of this third connection link 248 extends in a horizontal direction, and a link hole 250 extending in a longitudinal direction of the lower end part is formed in this lower end part.

A link shaft 254 protruding at a first angular portion of a triangular link 252 is inserted in this link hole 250 to be slidable in a longitudinal direction of the link hole 250. A second angular portion of this triangular link 252 is arranged on a side of the first angular portion, and pivoted on the base bottom portion 246. Moreover, the triangular link 252 can revolve with respect to the base bottom portion 246 around a 51st rotation axis O51 extending in a substantially horizontal direction through the second angular portion.

A third angular portion of the triangle link 252 is arranged below the first and second angular portions. One end part of a gas spring 256 is pivoted at the third angular portion of the triangle link 252. Additionally, the gas spring 256 can revolve with respect to the triangle link 252 around a 52nd rotation axis O52 extending in the substantially horizontal direction through one end part of the gas spring 256. The gas spring 256 is arranged in the base bottom portion 246 along a longitudinal direction of the base bottom portion 246. The other end part of the gas spring 256 is pivoted at a lower part of the base bottom portion 246. Further, the gas spring 256 can revolve with respect to the base bottom portion 246 around a 53rd rotation axis O53 extending in the substantially horizontal direction through the other end part of the gas spring 256.

The restriction mechanism 242 which is the same as the first restriction mechanism 152 (see FIGS. 10A, 10B and 10C) according to the third embodiment is arranged between the arm support portion 64 and the support member 240. A guide groove 258 of the restriction mechanism 242 is formed in a circumferential direction of a 36th rotation axis O36 as shown in FIG. 29. In this guide groove 258, a moving groove portion 260 is arranged on a side apart from the binocular tube 68b (see FIG. 29A), a fixing groove portion 262 is arranged on an opposite side, and a restriction groove portion 264 constricted like a gourd is arranged between the moving groove portion 260 and the fixing groove portion 262. A width of the moving groove portion 260 and a diameter of the fixing groove portion 262 are slightly larger than a diameter of a large-diameter portion 168 of a shaft portion 166 of a knob portion 244, and a minimum width of the restriction groove portion 264 is slightly smaller than the diameter of the large-diameter portion 168.

A function of the surgical microscope 110 having the above-mentioned structure according to this embodiment will now be described. When using the surgical microscope 110, the binocular tube 68b is manually moved to a desired position suitable for observation. A function of moving the binocular tube 68b in the front-and-back direction is the same as the function in the first reference embodiment.

Figure 30A:
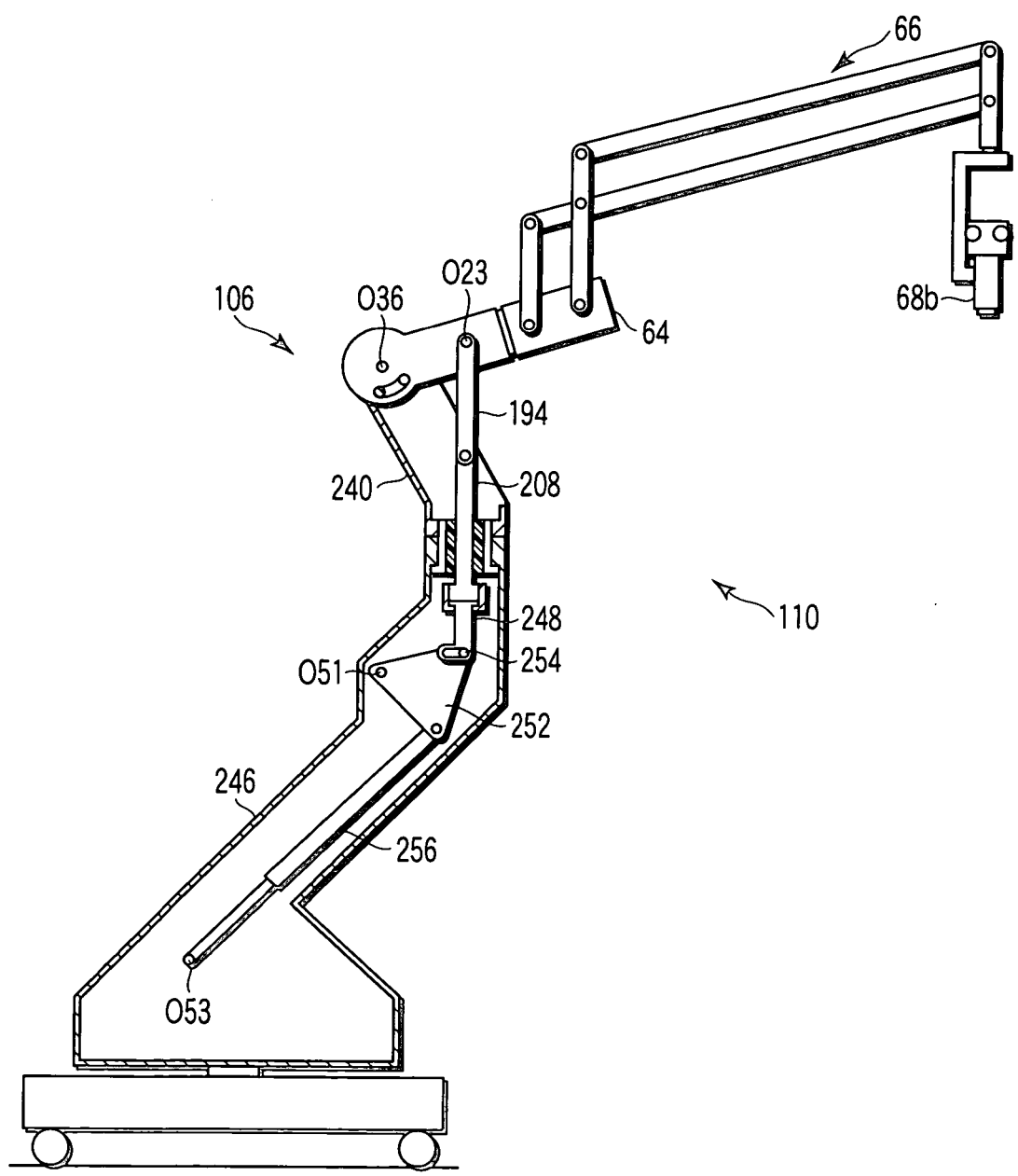
FIG. 30A is a cross-sectional view showing the surgical microscope according to the second reference embodiment of the present invention in a state where a microscope body is set at an in-use upward movement limit.

As shown in FIG. 30A, when moving up the binocular tube 68b, the vertical movement arm portion 66, the arm support portion 64 and the first and second connection links 194 and 208 function like the first reference embodiment. Further, the second connection link 208 drives the third connection link 248 to move up. The third connection link 248 drives the link shaft 254 of the first angular portion of the triangle link 252 to revolve upward around the 51st rotation axis O51.

Here, after the binocular tube 68b is moved to a desired position, when a hand is released from the binocular tube 68b, a function of the gas spring 256 offsets a rotation moment around the 23rd rotation axis O23, whereby the binocular tube 68b stands still at this position.

During the upward movement of the binocular tube 68b, as indicated by arrows D and D' in FIGS. 30B and 30C, the large-diameter portion 168 of the knob portion 244 is relatively moved in the moving groove portion 260 of the arm support portion 64 in a direction opposite to the fixing groove portion 262. As shown in FIG. 30C, when the large-diameter portion 168 is brought into contact with the end wall of the moving groove portion 260, the revolving movement of the arm support portion 64 around the 23rd rotation axis O23 is restricted. In this manner, the upward movement of the binocular tube 68b is limited. This state is an in-use upward movement limit of the binocular tube 68b.

Figure 31A:
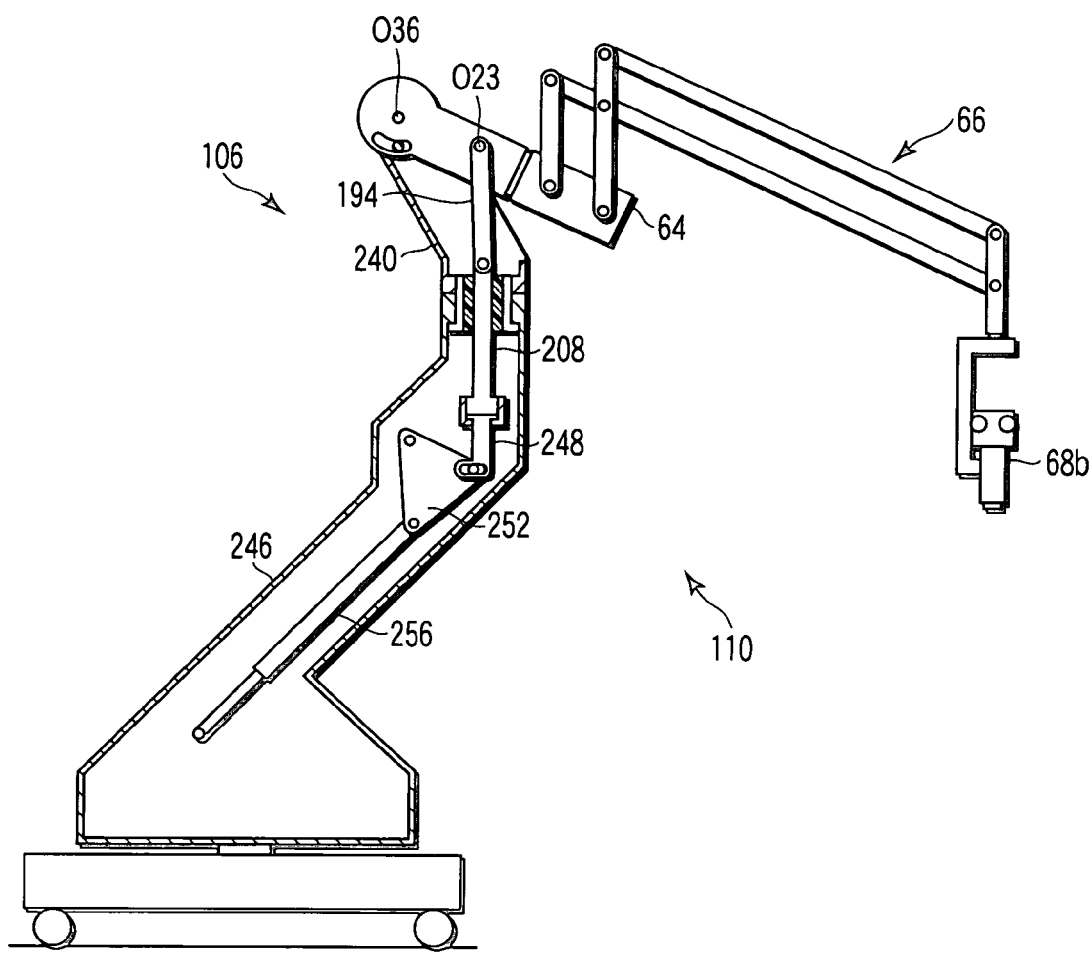
FIG. 31A is a cross-sectional view showing the surgical microscope according to the second reference embodiment of the present invention in a state where the microscope body is set at an in-use downward movement limit.
Figure 31B:
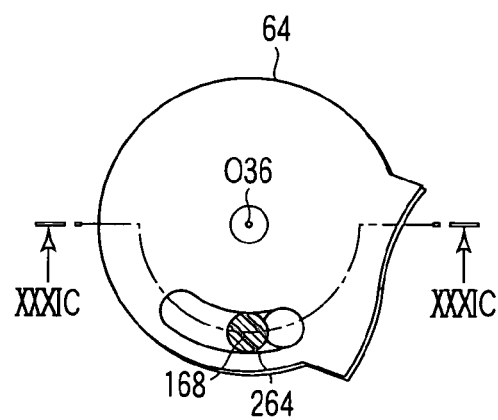
FIG. 31B is a cross-sectional view showing the restriction mechanism of the surgical microscope according to the second reference embodiment of the present invention in a state where the microscope body is set at the in-use downward movement limit.
Figure 31C:
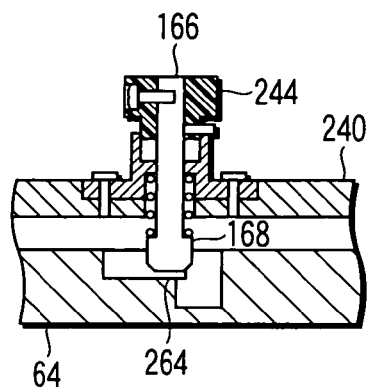
FIG. 31C is a cross-sectional view showing the restriction mechanism of the surgical microscope according to the second reference embodiment of the present invention in a state where the microscope body is set at the in-use downward movement limit taken along a line XXXIC-XXXIC in FIG. 31B.

As shown in FIG. 31A, when moving down the binocular tube 68b, a function which is opposite to that of the upward movement of the microscope body occurs. As shown in FIGS. 31B and 31C, when the large-diameter portion 168 is brought into contact with the constricted shape of the restriction groove portion 264, the revolving movement of the arm support portion 64 around the 23rd rotation axis O23 is restricted. This state is an in-use downward movable range of the binocular tube 68b.

Here, an in-use movable range of the arm support portion 64 with respect to the support member 240 is defined by a state in which the large-diameter portion 168 is in contact with the end wall of the moving groove portion 260 and a state in which the large-diameter portion 168 is in contact with the constricted shape of the restriction groove portion 264. Furthermore, an in-use upward movement limit and an in-use downward movement limit of the binocular tube 68b define an in-use upward/downward movement range of the binocular tube 68b.

Like the first reference embodiment, the forward/backward movement of the binocular tube 68b can be combined with the upward/downward movement of the same. Moreover, combining the in-use forward/backward movement range of the binocular tube 68b with the in-use upward/downward movement range of the same define an in-use movement range of the binocular tube 68b. Like the first reference embodiment, the binocular tube 68b is moved to a desired position by a rotating operation of the first arm 68a and the second connection block 64b of the arm support portion 64 in addition to the forward/backward movement and the upward/downward movement of the binocular tube 68b.

After the binocular tube 68b is used, the following accommodating operation is carried out when accommodating the binocular tube 68b. An accommodating operation based on the backward movement of the binocular tube 68b and an accommodating operation based on the downward movement of the binocular tube 68b will be separately described in order to simplify the explanation. The accommodating operation based on the backward movement of the binocular tube 68b is the same as that in the first reference embodiment.

Figure 32A:
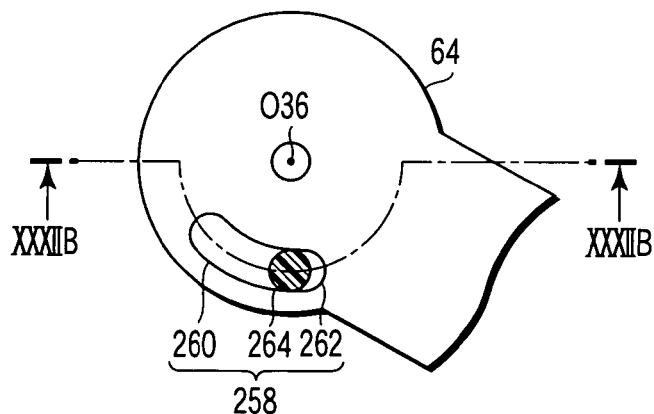
FIG. 32A is a cross-sectional view showing the restriction mechanism of the surgical microscope according to the second reference embodiment of the present invention in a state where the microscope body is set between the in-use downward movement limit and an in-accommodation downward movement limit.
Figure 32B:
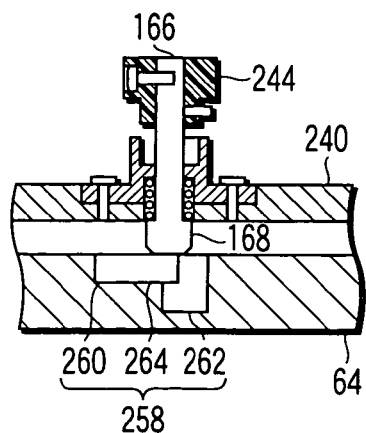
FIG. 32B is a cross-sectional view showing the restriction mechanism of the surgical microscope according to the second reference embodiment of the present invention in a state where the microscope body is set between the in-use downward movement limit and the in-accommodation downward movement limit taken along a line XXIIB-XXIIB in FIG. 32A.

In the accommodating operation based on the downward movement of the binocular tube 68b, the binocular tube 68b is set to such an in-use downward movement limit as shown in FIGS. 31A, 31B and 31C. Additionally, the knob portion 244 is outwardly moved in the axial direction, and the large-diameter portion 168 of the shaft portion 166 is pulled out from the restriction groove portion 264. In this state, the binocular tube 68b is moved down to revolve the arm support portion 64 around the 23rd rotation axis O23, and the large-diameter portion 168 is relatively moved beyond the restriction groove portion 264 from the moving groove portion 260 to the fixing groove portion 262 along the guide groove 258 as shown in FIGS. 32A and 32B.

Figure 33A:
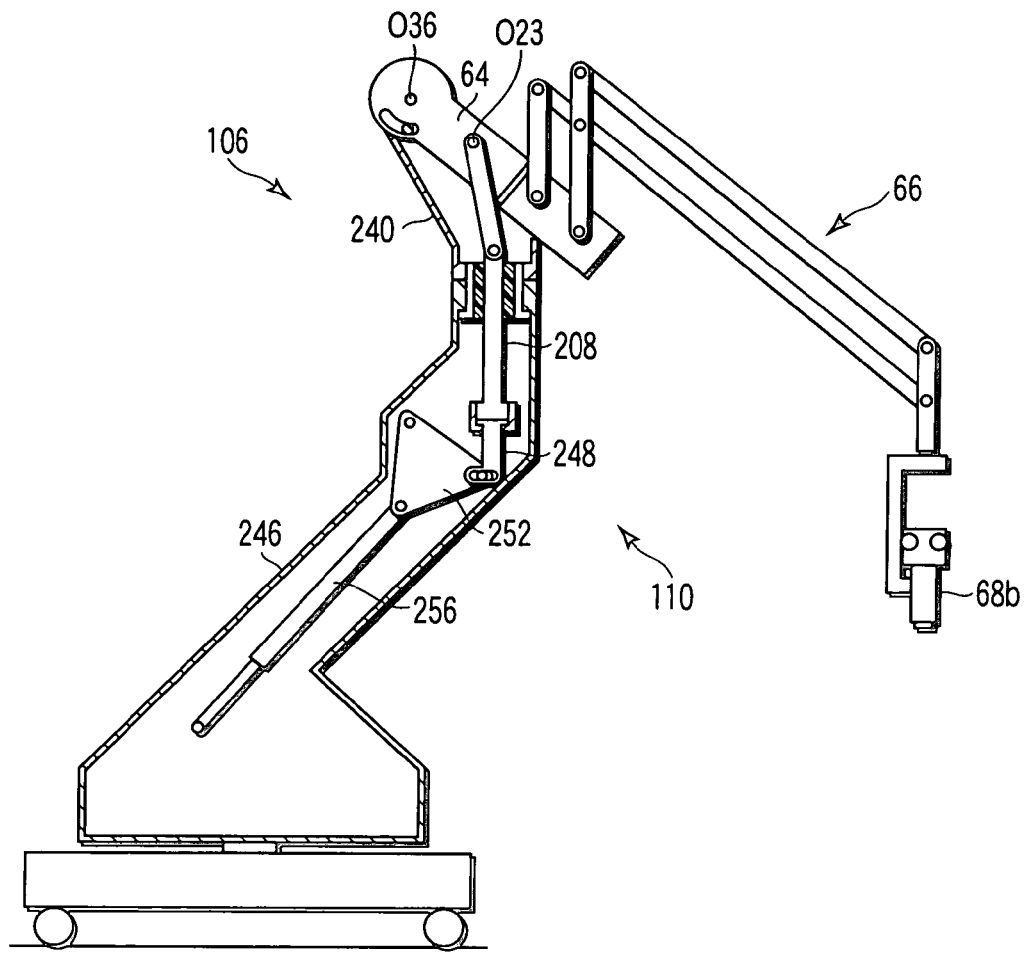
FIG. 33A is a cross-sectional view showing the surgical microscope according to the second reference embodiment of the present invention in a state where the microscope body is set at the in-accommodation downward movement limit.
Figure 33B:
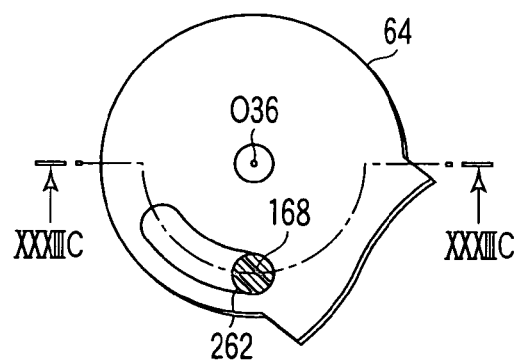
FIG. 33B is a cross-sectional view showing the restriction mechanism of the surgical microscope according to the second reference embodiment of the present invention in a state where the microscope body is set at the in-accommodation downward movement limit.
Figure 33C:
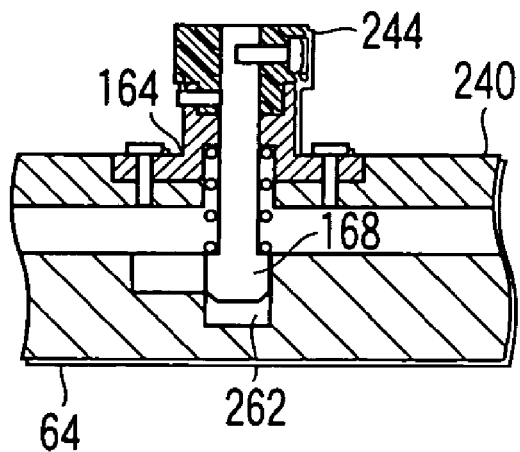
FIG. 33C is a cross-sectional view showing the restriction mechanism of the surgical microscope according to the second reference embodiment of the present invention in a state where the microscope body is set at the in-accommodation downward movement limit taken along a line XXXIIIC-XXXIIIC in FIG. 33B.
Figure 33D:
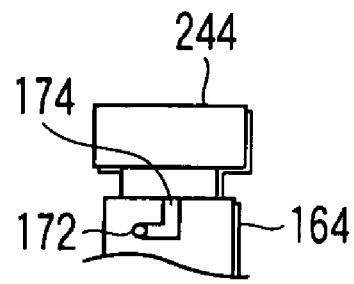
FIG. 33D is a side view showing a knob portion and a pedestal of the restriction mechanism of the surgical microscope according to the second reference embodiment of the present invention in a state where the microscope body is set at the in-accommodation downward movement limit.

Further, the binocular tube 68b is moved down to revolve the arm support portion 64 around the 23rd rotation axis O23 as shown in FIG. 33A, and the large-diameter portion 168 is aligned in the fixing groove portion 262 as shown in FIG. 33B. Then, like the first restriction mechanism 152 according to the third embodiment, the large-diameter portion 168 is fitted in the fixing groove portion 262 to lock the knob portion 244 with respect to the pedestal 164 as shown in FIGS. 33C and 33D. In this manner, the arm support portion 64 and the support member 240 are locked. This state is an in-accommodation downward movement limit of the binocular tube 68b.

Here, an in-accommodation movable range of the arm support portion 64 with respect to the support member 240 is defined by a state in which the large-diameter portion 168 is in contact with the constricted shape of the restriction groove portion 264 and a state in which the large-diameter portion 168 is fitted in the fixing groove portion 262. Furthermore, an in-use downward movement limit and an in-accommodation movement limit of the binocular tube 68b define an in-accommodation upward/downward movement range of the binocular tube 68b.

Like the first reference embodiment, in the actual accommodating operation, the accommodating operation based on the backward movement of the binocular tube 68b is combined with the accommodating operation based on the downward movement of the binocular tube 68b. Moreover, an in-accommodation movement range of the binocular tube 68b is defined by the in-accommodation upward/downward movement range of the binocular tube 68b.

Figure 34:
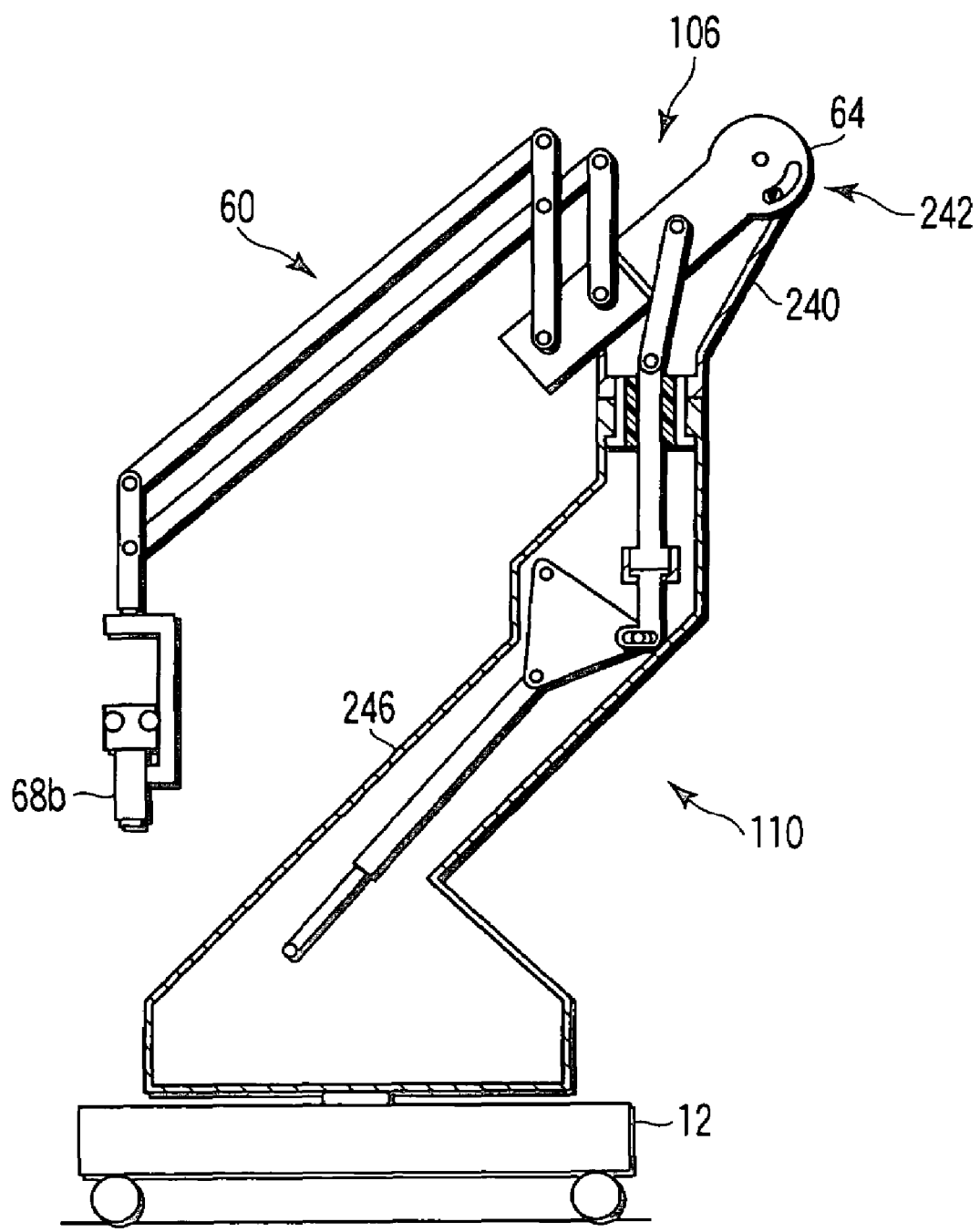
FIG. 34 is a cross-sectional view showing the surgical microscope according to the second reference embodiment of the present invention in an accommodation state.

The binocular tube 68b is moved in the in-accommodation movement range to shift the holding portion 106 to such an accommodation state as shown in FIG. 34. In this accommodation state, compact folding of the plurality of links of the holding portion 106 is allowed, the binocular tube 68b is arranged at a sufficiently low position above an intersecting point of the oblique shape of the base bottom portion 246 and the base 12, and a height of the holding portion 106 is an appropriate height. Additionally, when the arm support portion 64 is fixed with respect to the support member 240, the holding portion 106 is held in the accommodation state. That is, the restriction mechanism 242 according to this embodiment also serves as a fixing mechanism which holds the holding portion 106 in the accommodation state.

Thus, the device having the above-mentioned structure demonstrates the following effects in addition to the effects of the first reference embodiment. Since the base bottom portion 246 has the oblique shape, a sufficient space can be assured between an operator and the base bottom portion 246. Therefore, a sufficient operation space can be secured.

What is claimed is:

1. A surgical microscope comprising:
   a microscope portion including an observation mechanism;
   a base bottom portion in which a first horizontal rotation axis extending in a substantially horizontal direction is arranged;
   a horizontal movement arm portion which is supported by the base bottom portion to be revolvable around the first horizontal rotation axis and in which a second horizontal rotation axis extending in the substantially horizontal direction is arranged and which moves the microscope portion in the substantially horizontal direction;
   a vertical movement arm portion which is supported by the horizontal movement arm portion to be revolvable around the second horizontal rotation axis, supports the microscope portion and moves the microscope portion in a substantially vertical direction;
   a first elastic force generation mechanism which is connected with the base bottom portion and the horizontal movement arm portion, and generates an elastic force which offsets a rotation moment around the first horizontal rotation axis produced when the horizontal movement arm portion revolves around the first horizontal rotation axis; and
   a second elastic force generation mechanism which is connected with the base bottom portion and the vertical movement arm portion, and generates an elastic force which offsets a rotation moment around the second horizontal rotation axis produced when the vertical movement arm portion revolves around the second horizontal rotation axis, wherein the second elastic force generation mechanism includes: a link member revolvably supported by the base bottom portion; a coupling link which couples the vertical movement arm portion with the link member to transmit a moment from the vertical movement arm portion to the link member; and an elongated second elastic member having one end portion connected with the link member and the other end portion connected with the base bottom portion, and the second elastic member is configured to elastically expand/contract in a longitudinal direction thereof when the vertical movement arm portion revolves around the second horizontal rotation axis.

2. The surgical microscope according to claim 1, wherein the first elastic force generation mechanism includes an elongated first elastic member including one end portion connected with the horizontal movement arm portion and the other end portion connected with the base bottom portion, and the first elastic member is configured to elastically expand/contract in a longitudinal direction thereof when the horizontal movement arm portion revolves around the first horizontal rotation axis.

3. The surgical microscope according to claim 1, further comprising an auxiliary balance mechanism which generates a force which corrects the imbalance of a rotation moment of the vertical movement arm portion around the second horizontal rotation axis and a rotation moment around the second horizontal axis produced by an offsetting elastic force of the second elastic force generation mechanism.

4. The surgical microscope according to claim 3, wherein the auxiliary balance mechanism is provided on the base bottom portion and operated when the vertical movement arm portion revolves around the second horizontal rotation axis beyond a revolving range.

5. The surgical microscope according to claim 3, wherein the auxiliary balance mechanism includes a balance member and the balance member is pressed by the coupling link to generate an elastic force when the vertical movement arm portion revolves around the second horizontal rotation axis to move down the microscope portion in a substantially vertical direction.

6. The surgical microscope according to claim 1, further comprising a balance mechanism which generates a force which corrects the imbalance of a rotation moment of the vertical movement arm portion around the second horizontal rotation axis and a rotation moment around the second horizontal rotation axis produced by an offsetting elastic force of the second elastic force generation mechanism, wherein the balance mechanism has a balance member provided to the vertical movement arm portion, and the balance member is pressed by the coupling link to generate an elastic force when the vertical movement arm portion revolves around the second horizontal rotation axis to move down the microscope portion in a substantially vertical direction.

7. The surgical microscope according to claim 1, wherein at least one of the base bottom portion, the horizontal movement arm portion and the vertical movement arm portion has:

at least one movable portion which is moved when moving the microscope portion; and a restriction mechanism which restricts an in-use movable range in which the movable portion is moved when the microscope portion is used and an in-accommodation movable range which is a range different from the in-use movable range and in which the movable portion is moved when the microscope portion is accommodated.

8. The surgical microscope according to claim 7, wherein the restriction mechanism has a fixing mechanism which fixes the movable portion when the microscope portion is accommodated.

9. The surgical microscope according to claim 1, wherein the horizontal movement arm portion is constituted of a parallelogram link.

10. The surgical microscope according to claim 9, wherein the horizontal movement arm portion includes first and second links, and a joint portion at which end portions of the first and second links are respectively connected to be revolvable, and the other end portions of the first and second links are respectively connected with the base bottom portion to be revolvable in such a manner that the first and second links are arranged in parallel.

11. A surgical microscope comprising:

a microscope portion including an observation mechanism;

a base bottom portion in which a first horizontal rotation axis extending in a substantially horizontal direction is arranged;

a horizontal movement arm portion which is supported by the base bottom portion to be revolvable around the first horizontal rotation axis and in which a second horizontal rotation axis extending in the substantially horizontal direction is arranged and which moves the microscope portion in the substantially horizontal direction;

a vertical movement arm portion which is supported by the horizontal movement arm portion to be revolvable around the second horizontal axis, supports the microscope portion and moves the microscope portion in a substantially vertical direction;

a first elastic force generation mechanism which is connected with the base bottom portion and the horizontal movement arm portion, and generates an elastic force which offsets a rotation moment around the first horizontal rotation axis produced when the horizontal movement arm portion revolves around the first horizontal rotation axis; and a second elastic force generation mechanism which is connected with the base bottom portion and the vertical movement arm portion, and generates an elastic force which offsets a rotation moment around the second horizontal rotation axis produced when the vertical movement arm portion revolves around the second horizontal rotation axis, wherein the second elastic force generation mechanism includes: a second elastic member provided on the base bottom portion; and a coupling mechanism which is operated in accordance with the revolving of the vertical movement arm portion around the second horizontal rotation axis to transmit the rotation moment from the vertical movement arm portion to one end portion of the second elastic member, and the other end portion of the second elastic member is connected with the base bottom portion and the second elastic member is configured to elastically expand/contract in a longitudinal direction thereof when the vertical movement arm portion revolves around the second horizontal rotation axis.

12. The surgical microscope according to claim 11, wherein the first elastic force generation mechanism includes an elongated first elastic member including one end portion connected with the horizontal movement arm portion and the other end portion connected with the base bottom portion, and the first elastic member is configured to elastically expand/contract in a longitudinal direction thereof when the horizontal movement arm portion revolves around the fist horizontal rotation axis.

13. The surgical microscope according to claim 11, further comprising an auxiliary balance mechanism which generates a force which corrects the imbalance of a rotation moment of the vertical movement arm portion around the second horizontal rotation axis and a rotation moment around the second horizontal axis produced by an offsetting elastic force of the second elastic force generation mechanism.

14. The surgical microscope according to claim 13, wherein the auxiliary balance mechanism is provided on the base bottom portion and operated when the vertical movement arm portion revolves around the second horizontal rotation axis beyond a revolving range.

15. The surgical microscope according to claim 14, wherein the horizontal movement arm portion includes first and second links, and a joint portion at which end portions of the first and second links are respectively connected to be revolvable, and the other end portions of the first and second links are respectively connected with the base bottom portion to be revolvable in such a manner that the first and second links are arranged in parallel.

16. The surgical microscope according the claim 11, wherein the horizontal movement arm portion is constituted of a parallelogram link.

* * * * *